US008450354B2

(12) United States Patent
Mjalli et al.

(10) Patent No.: US 8,450,354 B2
(45) Date of Patent: May 28, 2013

(54) SUBSTITUTED IMIDAZO[1,2-B]PYRIDAZINE DERIVATIVES, PHARMACEUTICAL COMPOSITIONS, AND METHODS OF USE AS β-SECRETASE INHIBITORS

(75) Inventors: Adnan M. M. Mjalli, Oak Ridge, NC (US); Anitha Hari, High Point, NC (US); Bapu Gaddam, High Point, NC (US); Devi Reddy Gohimukkula, Jamestown, NC (US); Dharma Rao Polisetti, High Point, NC (US); Mohan Rao, Greensboro, NC (US); Raju Bore Gowda, Oak Ridge, NC (US); Robert Carl Andrews, Jamestown, NC (US); Rongyuan Xie, Greensboro, NC (US); Soumya P. Sahoo, Greensboro, NC (US); Tan Ren, Colfax, NC (US); William Kenneth Banner, Greensboro, NC (US)

(73) Assignee: High Point Pharmaceuticals, LLC, High Point, NC (US)

( * ) Notice: Subject to any disclaimer, the term of this patent is extended or adjusted under 35 U.S.C. 154(b) by 0 days.

(21) Appl. No.: 13/052,544

(22) Filed: Mar. 21, 2011

(65) Prior Publication Data
US 2011/0237570 A1    Sep. 29, 2011

Related U.S. Application Data

(60) Provisional application No. 61/316,599, filed on Mar. 23, 2010.

(51) Int. Cl.
*A01N 43/50* (2006.01)
*A61K 31/415* (2006.01)
*C07D 403/02* (2006.01)

(52) U.S. Cl.
USPC ........... 514/396; 514/250; 544/236; 544/238; 548/303.1; 548/304.4

(58) Field of Classification Search
USPC ..... 544/236, 238; 548/303.1, 304.4; 514/250, 514/396
See application file for complete search history.

(56) References Cited

U.S. PATENT DOCUMENTS

| | | | |
|---|---|---|---|
| 6,696,437 | B1 | 2/2004 | Lubisch et al. |
| 7,338,956 | B2 | 3/2008 | Strobel et al. |
| 7,893,267 | B2 | 2/2011 | Mjalli et al. |
| 2002/0123484 | A1 | 9/2002 | Das et al. |
| 2003/0134854 | A1 | 7/2003 | Flohr et al. |
| 2003/0236267 | A1 | 12/2003 | Kobayashi et al. |
| 2006/0223849 | A1 | 10/2006 | Mjalli et al. |
| 2011/0065713 | A1 | 3/2011 | Mjalli et al. |
| 2012/0101093 | A1 | 4/2012 | Mjalli et al. |
| 2012/0101125 | A1 | 4/2012 | Mjalli et al. |

FOREIGN PATENT DOCUMENTS

| | | |
|---|---|---|
| WO | WO 01/00611 | 1/2001 |
| WO | WO 01/21615 | 3/2001 |
| WO | WO 02/069965 | 9/2002 |
| WO | WO 03/032984 | 4/2003 |
| WO | WO 03/041708 | 5/2003 |
| WO | WO 03/053939 | 7/2003 |
| WO | WO 03/075921 | 9/2003 |
| WO | WO 2004/014369 | 2/2004 |
| WO | WO 2006/099379 | 9/2006 |

OTHER PUBLICATIONS

Cheng et al., "Synthesis and Antiviral Activity Against Coxsackie Virus B3 of some Novel Benzimidazole Derivatives" Bioorganic & Medicinal Chemistry Letters, 15(2):267-269 (2005).
Denny, et al., "Potential Antitumor Agents" Journal of Medicinal Chemistry, 33(2):814-819 (1990).
Ghosh et al., "Potent Memapsin 2 (beta-Secretase) Inhibitors: Design, Synthesis, Protein-Ligand X-ray Structure and in Vivo Evaluation" Bioorganic & Medicinal Chemistry Letters, 18(3):1031-1036 (2008).
International Search Report and Written Opinion for PCT Application No. PCT/US2011/029147, mailed May 18, 2011.
Office Action of Jun. 8, 2012 for U.S. Appl. No. 13/214,434.
Silverman, The Organic Chemistry of Drug Design and Drug Action, 1st Ed., Chapter 2: Drug Discovery, Design, and Development, Academic Press, pp. 5-51 (1992).
Silverman, The Organic Chemistry of Drug Design and Drug Action, 2nd Ed., Elsevier Academic Press, Burlington, MA, pp. 29-34 (2004).
Silvestri, "Boom in the Development of Non-Peptidic Beta-Secretase (BACE1) Inhibitors for the Treatment of Alzheimer's Disease" Medicinal Research Reviews, 29(2):295-338 (2009).
Wermuth, The Practice of Medicinal Chemistry, Chapter 13: Molecular Variations Based on Isosteric Replacements, 2nd Ed., Elsevier, pp. 189-214 (2003).

*Primary Examiner* — Paul V. Ward
(74) *Attorney, Agent, or Firm* — Samuel B. Rollins

(57) ABSTRACT

The present invention provides substituted imidazo[1,2-b]pyridazine derivatives, pharmaceutically acceptable salts thereof, and tautomers of any of the foregoing, where such compounds inhibit β-site amyloid precursor protein-cleaving enzyme (BACE), which may be useful in the treatment of diseases in which BACE is involved, such as Alzheimer's disease. The invention also provides pharmaceutical compositions comprising any of these compounds and the use of any of these compounds and compositions in the treatment of diseases, disorders, or conditions in which BACE is involved.

22 Claims, No Drawings

SUBSTITUTED IMIDAZO[1,2-B]PYRIDAZINE DERIVATIVES, PHARMACEUTICAL COMPOSITIONS, AND METHODS OF USE AS β-SECRETASE INHIBITORS

CROSS-REFERENCE TO RELATED APPLICATION

This application claims the benefit of priority to U.S. Provisional Patent Application No. 61/316,599, filed Mar. 23, 2010, the entirety of which is incorporated by reference as though fully set forth herein.

FIELD OF INVENTION

The present invention relates to substituted imidazo[1,2-b]pyridazines useful as inhibitors of β-secretase, the β-site amyloid precursor protein-cleaving enzyme (BACE).

DESCRIPTION OF RELATED ART

Alzheimer's disease is characterized by the abnormal deposition of β-amyloid (Aβ) in the brain in the form of extra-cellular plaques and intra-cellular neurofibrillary tangles. The rate of amyloid accumulation is a combination of the rates of Aβ formation, aggregation, and egress from the brain. It is generally accepted that the main constituent of amyloid plaques is the 4 kD amyloid protein (βA4, also referred to as Aβ, β-protein and βAP) which is a proteolytic product of a precursor protein of much larger size.

Amyloid precursor protein (APP) is a 695-770 amino acid glycoprotein, expressed in the neurons and glial cells in peripheral tissues. APP has a receptor-like structure with a large ectodomain, a membrane spanning region, and a short cytoplasmic tail. Aβ is a 39-42 amino acid peptide, constitutes part of the ectodomain of APP, and extends partly to the transmembrane domain of APP.

At least two secretory mechanisms exist which release APP from the membrane and generate soluble, truncated forms of APP (sAPP). Proteases that release APP and its fragments from the membrane are termed "secretases." Most sAPP is released by a putative α-secretase that cleaves within the Aβ protein to release sAPPα and precludes the release of intact Aβ. A smaller portion of sAPP is released by a β-secretase that cleaves near the $NH_2$-terminus of APP and produces COOH-terminal fragments (CTFs) which contain the complete Aβ domain.

Thus, the activity of β-secretase or β-site amyloid precursor protein-cleaving enzyme ("BACE") leads to the abnormal cleavage of APP, production of Aβ, and accumulation of β-amyloid plaques in the brain, which is characteristic of Alzheimer's disease. In addition, the processing of APP by β-secretase is thought to be the rate-determining step in Aβ production. Therefore, therapeutic agents that can inhibit BACE may be useful for the treatment of Alzheimer's disease.

The compounds of the present invention may be useful for treating Alzheimer's disease by inhibiting the activity of the BACE, thus preventing or reducing the rate of formation of insoluble Aβ.

BRIEF SUMMARY OF THE INVENTION

The present invention is directed to substituted imidazo[1,2-b]pyridazine derivatives that inhibit the β-site amyloid precursor protein-cleaving enzyme (BACE) and that therefore may be useful in the treatment of diseases in which BACE is involved, such as Alzheimer's disease. The invention is also directed to pharmaceutical compositions comprising substituted imidazo[1,2-b]pyridazine derivatives and the use of these compounds and pharmaceutical compositions in the treatment of diseases in which BACE is involved.

In one aspect, the present invention provides compounds of Formula (I), pharmaceutically acceptable salts thereof, and tautomers of any of the foregoing, where the identity of individual substituents is set forth in greater detail below.

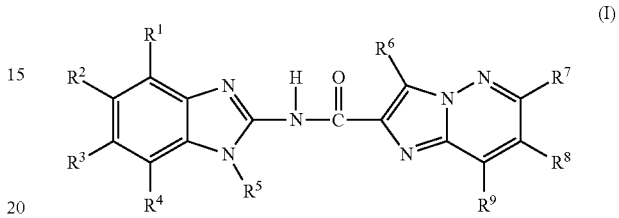

In another aspect, the present invention provides methods for the preparation of compounds of Formula (I), pharmaceutically acceptable salts thereof, and tautomers of any of the foregoing.

In another aspect, the present invention provides pharmaceutical compositions comprising a compound of Formula (I), a pharmaceutically acceptable salt thereof, or a tautomer of any of the foregoing. In one embodiment, the pharmaceutical composition comprises a compound of Formula (I), a pharmaceutically acceptable salt thereof, or a tautomer of any of the foregoing, and a pharmaceutically acceptable carrier, excipient, diluent, or mixture thereof. In another aspect, the present invention provides a method for the preparation of a pharmaceutical composition comprising a compound of Formula (I), a pharmaceutically acceptable salt thereof, or a tautomer of any of the foregoing.

In another aspect, the present invention provides methods of treatment comprising administering a compound of Formula (I), a pharmaceutically acceptable salt thereof, or a tautomer of any of the foregoing, or a pharmaceutical composition comprising a compound of Formula (I), a pharmaceutically acceptable salt thereof, or a tautomer of any of the foregoing, to a subject who has a disease, disorder, or condition.

In another aspect, the present invention provides methods of treatment comprising administering a compound of Formula (I), a pharmaceutically acceptable salt thereof, or a tautomer of any of the foregoing, or a pharmaceutical composition comprising a compound of Formula (I), a pharmaceutically acceptable salt thereof, or a tautomer of any of the foregoing to a subject having a disease, disorder, or condition or a subject at risk for having a disease, disorder, or condition, wherein the disease, disorder, or condition is selected from the group consisting of: Alzheimer's disease, mild cognitive impairment, dementia of the Alzheimer's type, Down's syndrome, Hereditary Cerebral Hemorrhage with Amyloidosis of the Dutch-Type, cerebral amyloid angiopathy, degenerative dementia, diffuse Lewy body type of Alzheimer's disease, and central or peripheral amyloid diseases.

Additional features of the present invention are described hereinafter.

BRIEF DESCRIPTION OF DRAWINGS

Not applicable.

DETAILED DESCRIPTION

The following definitions are meant to clarify the terms defined. If a particular term used herein is not specifically defined, the term should not be considered to be indefinite. Rather, such undefined terms are to be construed in accordance with their plain and ordinary meaning to skilled artisans in a field of art to which the invention is directed.

As used herein the term "alkyl" refers to a fully saturated straight or branched chain hydrocarbon having one to ten carbon atoms, which may be optionally substituted, as herein further described, with multiple degrees of substitution being allowed. Examples of "alkyl" as used herein include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl.

As used throughout this specification, the number carbon atoms in an alkyl group will be represented by the phrase "$C_{x-y}$ alkyl," which refers to an alkyl group, as herein defined, containing from x to y, inclusive, carbon atoms. Thus, $C_{1-6}$ alkyl represents an alkyl chain having from 1 to 6 carbons as described above, and for example, includes, but is not limited to, methyl, ethyl, n-propyl, isopropyl, isobutyl, n-butyl, sec-butyl, tert-butyl, isopentyl, n-pentyl, neopentyl, and n-hexyl.

As used herein, the term "alkylene" refers to a fully saturated straight or branched chain divalent hydrocarbon radical having from one to ten carbon atoms, which may be optionally substituted as herein further described, with multiple degrees of substitution being allowed. Examples of "alkylene" as used herein include, but are not limited to, methylene, ethylene, n-propylene, 1-methylethylene, 2-methylethylene, dimethylmethylene, n-butylene, 1-methyl-n-propylene, and 2-methyl-n-propylene.

As used throughout this specification, the number of carbon atoms in an alkylene group will be represented by the phrase "$C_{x-y}$ alkylene," which refers to an alkylene group, as herein defined, containing from x to y, inclusive, carbon atoms. Thus, $C_{1-4}$ alkylene represents an alkylene chain having from 1 to 4 carbons as described above, and for example, includes, but is not limited to, methylene, ethylene, n-propylene, 1-methylethylene, 2-methylethylene, dimethylmethylene, n-butylene, 1-methyl-n-propylene, and 2-methyl-n-propylene.

As used herein, the term "cycloalkyl" refers to a three- to ten-membered, cyclic hydrocarbon ring, which may be optionally substituted as herein further described, with multiple degrees of substitution being allowed. Such "cycloalkyl" groups are monocyclic, bicyclic, or tricyclic. The term "cycloalkyl," as used herein, does not include ring systems which contain any aromatic rings, but does include ring systems that have one or more degrees of unsaturation. Examples of "cycloalkyl" groups as used herein include, but are not limited to, cyclopropyl, cyclobutyl, cyclopentyl, cyclohexyl, cycloheptyl, 1-norbornyl, 2-norbornyl, 7-norbornyl, 1-adamantyl, and 2-adamantyl.

As used throughout this specification, the number of carbon atoms in a cycloalkyl group will be represented by the phrase "$C_{x-y}$ cycloalkyl," which refers to a cycloalkyl group, as herein defined, containing from x to y, inclusive, carbon atoms. Similar terminology will apply for other terms and ranges as well. Thus, $C_{3-10}$ cycloalkyl represents a cycloalkyl group having from 3 to 10 carbons as described above, and for example, includes, but is not limited to, cyclopropyl, cyclobutyl, cyclopentyl, cyclohexyl, cycloheptyl, 1-norbornyl, 2-norbornyl, 7-norbornyl, 1-adamantyl, and 2-adamantyl.

As used herein, the term "heterocycle" or "heterocyclyl" refers to a mono- or polycyclic ring system containing one or more heteroatoms. Such "heterocycle" or "heterocyclyl" groups may be optionally substituted as herein further described, with multiple degrees of substitution being allowed. The terms "heterocycle" or "heterocyclyl," as used herein, do not include ring systems which contain any aromatic rings, but do include ring systems that have one or more degrees of unsaturation. Examples of heteroatoms include nitrogen, oxygen, or sulfur atoms, including N-oxides, sulfur oxides, and sulfur dioxides. Carbon atoms in the ring system can also be optionally oxidized to form heterocyclic rings such as, 2-oxo-pyrrolidin-1-yl or 2-oxo-piperidin-1-yl. Any ring in the ring system is three- to twelve-membered. Such rings may be optionally fused to one or more of another heterocyclic ring(s) or cycloalkyl ring(s). Examples of "heterocycle" or "heterocyclyl" groups, as used herein, include, but are not limited to, tetrahydrofuran, tetrahydropyran, 1,4-dioxane, 1,3-dioxane, piperidine, pyrrolidine, morpholine, tetrahydrothiopyran, and tetrahydrothiophene, where attachment can occur at any point on said rings, as long as attachment is chemically feasible. Thus, for example, "morpholine" can refer to morpholin-2-yl, morpholin-3-yl, and morpholin-4-yl.

As used herein, when "heterocycle" or "heterocyclyl" is recited as a possible substituent, the "heterocycle" or "heterocyclyl" group can attach through either a carbon atom or any heteroatom, to the extent that attachment at that point is chemically feasible. For example, "heterocyclyl" would include pyrrolidin-1-yl, pyrrolidin-2-yl, and pyrrolidin-3-yl. When "heterocycle" or "heterocyclyl" groups contain a nitrogen atom in the ring, attachment through the nitrogen atom can alternatively be indicated by using an "-ino" suffix with the ring name. For example, pyrrolidino refers to pyrrolidin-1-yl.

As used herein the term "halogen" refers to fluorine, chlorine, bromine, or iodine.

As used herein the term "haloalkyl" refers to an alkyl group, as defined herein, that is substituted one or more times with halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include groups such as —$CF_3$, —$CH_2$—$CF_3$, and —$CF_2Cl$.

As used herein, the term "aryl" refers to a six- to ten-membered cyclic, aromatic hydrocarbon, which may be optionally substituted as herein further described, with multiple degrees of substitution being allowed. Examples of "aryl" groups as used herein include, but are not limited to, phenyl and naphthyl. As used herein, the term "aryl" also includes ring systems in which a phenyl or naphthyl group is optionally fused with one to three non-aromatic, saturated or unsaturated, carbocyclic rings. For example, "aryl" would include ring systems such as indene, with attachment possible to either the aromatic or the non-aromatic ring(s).

As used herein, the term "heteroaryl" refers to a five- to fourteen-membered optionally substituted mono- or polycyclic ring system, which contains at least one aromatic ring and also contains one or more heteroatoms. Such "heteroaryl" groups may be optionally substituted as herein further described, with multiple degrees of substitution being allowed. In a polycyclic "heteroaryl" group that contains at least one aromatic ring and at least one non-aromatic ring, the aromatic ring(s) need not contain a heteroatom. Thus, for example, "heteroaryl," as used herein, would include indolinyl. Further, the point of attachment may be to any ring within the ring system without regard to whether the ring containing the attachment point is aromatic or contains a heteroatom. Thus, for example, "heteroaryl," as used herein, would include indolin-1-yl, indolin-3-yl, and indolin-5-yl. Examples of heteroatoms include nitrogen, oxygen, or sulfur atoms, including N-oxides, sulfur oxides, and sulfur dioxides, where feasible. Examples of "heteraryl" groups, as used herein include, but are not limited to, furyl, thiophenyl, pyrrolyl, oxazolyl, thiazolyl, imidazolyl, isoxazolyl, isothiazolyl, 1,2,4-triazolyl, pyrazolyl, pyridinyl, pyridazinyl, pyrimidinyl, indolyl, isoindolyl, benzo[b]thiophenyl, benzimidazolyl, benzothiazolyl, pteridinyl, and phenazinyl, where attachment can occur at any point on said rings, as long as attachment is chemically feasible. Thus, for example, "thiazolyl" refers to thiazol-2-yl, thiazol-4-yl, and thiaz-5-yl.

As used herein, when "heteroaryl" is recited as a possible substituent, the "heteroaryl" group can attach through either a carbon atom or any heteroatom, to the extent that attachment at that point is chemically feasible.

As used herein, the term "substituted" refers to substitution of one or more hydrogens of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. As used herein, the phrases "substituted with one or more . . ." or "substituted one or more times . . ." refer to a number of substituents that equals from one to the maximum number of substituents possible based on the number of available bonding sites, provided that the above conditions of stability and chemical feasibility are met.

As used herein, the various functional groups represented will be understood to have a point of attachment at the functional group having the hyphen or dash (-) or an asterisk (*). In other words, in the case of —$CH_2CH_2CH_3$, it will be understood that the point of attachment is the $CH_2$ group at the far left. If a substituent group is recited without an asterisk or a dash, then its attachment point is the attachment point that skilled artisans would generally associate with that group. For example, "methyl" is —$CH_3$, as that conforms to the generally understood meaning of what a methyl group is.

When any variable occurs more than one time in any one constituent (e.g., $R^a$), or multiple constituents, its definition on each occurrence is independent of its definition on every other occurrence.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

As used herein, the term "optionally" means that the subsequently described event(s) may or may not occur.

As used herein, "administer" or "administering" means to introduce, such as to introduce to a subject a compound or composition. The term is not limited to any specific mode of delivery, and can include, for example, subcutaneous delivery, intravenous delivery, intramuscular delivery, intracisternal delivery, delivery by infusion techniques, transdermal delivery, oral delivery, nasal delivery, and rectal delivery. Furthermore, depending on the mode of delivery, the administering can be carried out by various individuals, including, for example, a health-care professional (e.g., physician, nurse, etc.), a pharmacist, or the subject (i.e., self-administration).

As used herein, "treat" or "treating" or "treatment" can refer to one or more of: delaying the progress of a disease, disorder, or condition; controlling a disease, disorder, or condition; delaying the onset of a disease, disorder, or condition; ameliorating one or more symptoms characteristic of a disease, disorder, or condition; or delaying the recurrence of a disease, disorder, or condition, or characteristic symptoms thereof, depending on the nature of the disease, disorder, or condition and its characteristic symptoms.

As used herein, "subject" refers to any mammal such as, but not limited to, humans, horses, cows, sheep, pigs, mice, rats, dogs, cats, and primates such as chimpanzees, gorillas, and rhesus monkeys. In an embodiment, the "subject" is a human. In another embodiment, the "subject" is a human who exhibits one or more symptoms characteristic of a disease, disorder, or condition. In another embodiment, the "subject" is a human who has a disease, disorder, or condition in which BACE is involved. The term "subject" does not require one to have any particular status with respect to a hospital, clinic, or research facility (e.g., as an admitted patient, a study participant, or the like).

As used herein, the term "compound" includes free acids, free bases, and salts thereof. Thus, phrases such as "the compound of embodiment 1" or "the compound of claim 1" are intended to refer to any free acids, free bases, and salts thereof that are encompassed by embodiment 1 or claim 1.

As used herein, "substituted imidazo[1,2-b]pyridazine derivatives" refers to derivatives of 2-imidazo[1,2-b]pyridazine carboxylic acid benzimidazol-2-yl amide represented by Formula (I), as described in detail below.

As used herein, the term "pharmaceutical composition" is used to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

As used herein, the term "tautomer," used in reference to compounds or salts of the invention, refers to tautomers that can form with respect to substituted benzimidazole groups, as shown below.

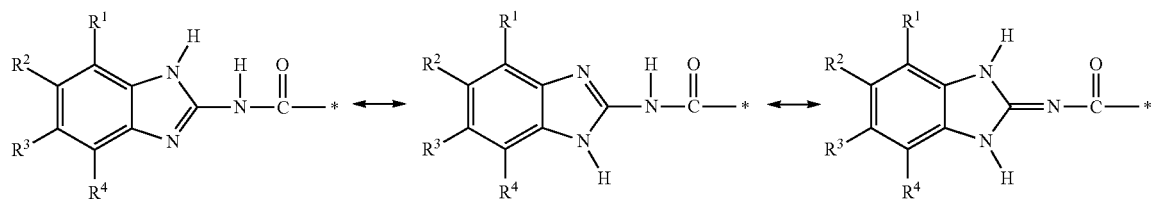

The present invention includes all such tautomers and methods of making and using the same. Throughout this specification, whenever a chemical formula (generic or otherwise) discloses a compound having a 1H-benzimidazole moiety that is unsubstituted at the 1 position (as illustrated in the far left-hand structure shown immediately above), that chemical formula also implicitly discloses compounds that are otherwise identical except that the benzimidazole moiety undergoes tautomerization to form either of the other two benzimidazole tautomers shown immediately above. Thus, the phrase "a tautomer of a compound of Formula (I)" refers to compounds of Formula (I) where the $R^5$ group of Formula (I) is hydrogen, and where said tautomer is related to a compound of Formula (I) according to the tautomeric relationship described immediately above.

As used herein, the term "BACE inhibitor" or "inhibitor of BACE" is used to signify a compound having a structure, as defined herein, which is capable of interacting with BACE and inhibiting its enzymatic activity. Inhibiting BACE enzymatic activity means reducing the ability of BACE to cleave a peptide or protein. The peptide or protein may be APP, and a BACE inhibitor may reduce the ability of BACE to cleave APP near the $NH_2$ terminus of APP and produce COOH-terminal fragments (CTFs) that contain the complete Aβ domain. In various embodiments, such reduction of BACE activity is at least about 50%, at least about 75%, at least about 90%, at least about 95%, or at least about 99%. In various embodiments, the concentration of BACE inhibitor required to reduce a BACE's enzymatic activity is less than about 30 μM, less than about 10 μM, or less than about 1 μM.

Also included within the scope of the invention are the individual enantiomers of the compounds represented by Formula (I), pharmaceutically acceptable salts thereof, or tautomers of any of the foregoing, as well as any wholly or partially racemic mixtures thereof. The invention also covers the individual enantiomers of the compounds represented by Formula (I), pharmaceutically acceptable salts thereof, or tautomers of any of the foregoing, as well as mixtures with diastereoisomers thereof in which one or more stereocenters are inverted. Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}C$- or $^{14}C$-enriched carbon are within the scope of the invention.

In several aspects, the present invention relates to substituted imidazo[1,2-b]pyridazine derivatives, pharmaceutical compositions comprising substituted imidazo[1,2-b]pyridazine derivatives, methods of making substituted imidazo[1,2-b]pyridazine derivatives, methods of making pharmaceutical compositions comprising substituted imidazo[1,2-b]pyridazine derivatives, and methods of using substituted imidazo[1,2-b]pyridazine derivatives or pharmaceutical compositions comprising substituted imidazo[1,2-b]pyridazine derivatives, particularly for the treatment of diseases, disorders, or conditions that may be related to the enzymatic activity of BACE, such as Alzheimer's disease.

In a first aspect, the present invention provides substituted imidazo[1,2-b]pyridazine derivatives, pharmaceutically acceptable salts thereof, and tautomers of any of the foregoing. Such compounds, salts, or tautomers thereof are useful in the reduction of the proteolytic activity of BACE, as discussed in more detail below.

In a first embodiment (i.e., embodiment 1), the invention provides a compound of Formula (I) or a pharmaceutically acceptable salt thereof:

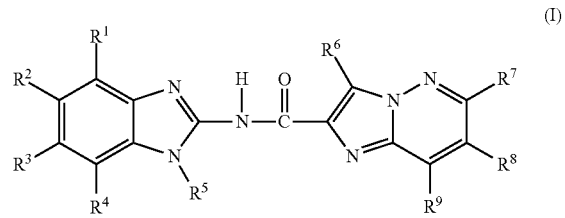

(I)

wherein
$R^1$, $R^2$, $R^3$, and $R^4$ are each independently selected from the group consisting of:
a) —H,
b) -halogen,
c) —$C_{1-6}$ alkyl,
d) —$C_{3-10}$ cycloalkyl,
e) —$C_{1-4}$ alkylene-$C_{3-10}$ cycloalkyl,
f) -heterocyclyl,
g) —$C_{1-4}$ alkylene-heterocyclyl,
h) -phenyl,
i) —$C_{1-4}$ alkylene-phenyl,
j) -heteroaryl,
k) —$C_{1-4}$ alkylene-heteroaryl,
l) -cyano,
m) —$CF_3$,
n) —$OCF_3$,
o) —O—$R^a$,
p) —S(O), $R^a$,
q) —S(O)$_2$O—$R^a$,
r) —N$R^a R^b$,
s) —C(O)—$R^a$,
t) —C(O)—O—$R^a$,
u) —OC(O)—$R^a$,
v) —C(O)N$R^a R^b$,
w) —N$R^a$C(O)$R^b$,
x) —OC(O)N$R^a R^b$,
y) —N$R^a$C(O)O$R^b$, and
z) —N$R^a$C(O)N$R^a R^b$,
where the alkyl, alkylene, cycloalkyl, heterocyclyl, phenyl, and heteroaryl groups are optionally substituted one or more times with substituents independently selected from $R^z$;

$R^5$ is hydrogen, —$C_{1-6}$ alkyl, or —$C_{1-4}$ alkylene-$C_{3-10}$ cycloalkyl, where the alkyl, alkylene, and cycloalkyl groups are optionally substituted one or more times with substituents independently selected from $R^z$.

$R^6$ is hydrogen, —$C_{1-6}$ alkyl, or —$C_{1-4}$ alkylene-$C_{3-10}$ cycloalkyl, where the alkyl, alkylene, and cycloalkyl groups are optionally substituted one or more times with substituents independently selected from $R^z$.

$R^7$ is:
a) —H,
b) -halogen,
c) —$C_{1-6}$ alkyl,
d) —$C_{3-10}$ cycloalkyl,
e) —$C_{1-4}$ alkylene-$C_{3-10}$ cycloalkyl,
f) -heterocyclyl,
g) —$C_{1-4}$ alkylene-heterocyclyl,
h) -phenyl,
i) —$C_{1-4}$ alkylene-phenyl,
j) -heteroaryl,
k) —$C_{1-4}$ alkylene-heteroaryl,
l) -cyano,
m) —$CF_3$,
n) —$OCF_3$,
o) —O—$R^c$,
p) —$S(O)_w$—$R^c$,
q) —$S(O)_2O$—$R^c$,
r) —$NR^cR^d$,
s) —C(O)—$R^c$,
t) —C(O)—O—$R^c$,
u) —OC(O)—$R^c$,
v) —C(O)$NR^cR^d$,
w) —$NR^cC(O)R^d$,
x) —OC(O)$NR^cR^d$,
y) —$NR^cC(O)OR^d$,
z) —$NR^cC(O)NR^cR^d$,
aa) —O—$C_{1-6}$ alkylene-O—$R^c$, or
bb) —O—$C_{1-6}$ alkylene-$NR^cR^d$,
where the alkyl, alkylene, cycloalkyl, heterocyclyl, phenyl, and heteroaryl groups are optionally substituted one or more times with substituents independently selected from $R^y$;

$R^8$ and $R^9$ are each independently selected from the group consisting of:
a) —H,
b) -halogen,
c) —$C_{1-6}$ alkyl,
d) —$C_{3-10}$ cycloalkyl,
e) —$C_{1-4}$ alkylene-$C_{3-10}$ cycloalkyl,
f) -heterocyclyl,
g) —$C_{1-4}$ alkylene-heterocyclyl,
h) -phenyl,
i) —$C_{1-4}$ alkylene-phenyl,
j) -heteroaryl,
k) —$C_{1-4}$ alkylene-heteroaryl,
l) -cyano,
m) —$CF_3$,
n) —$OCF_3$,
o) —O—$R^a$,
p) —$S(O)_w$—$R^a$,
q) —$S(O)_2O$—$R^a$,
r) —$NR^aR^b$,
s) —C(O)—$R^a$,
t) —C(O)—O—$R^a$,
u) —OC(O)—$R^a$,
v) —C(O)$NR^aR^b$,
w) —$NR^aC(O)R^b$,
x) —OC(O)$NR^aR^b$,
y) —$NR^aC(O)OR^b$, and
z) —$NR^aC(O)NR^aR^b$,
where the alkyl, alkylene, cycloalkyl, heterocyclyl, phenyl, and heteroaryl groups are optionally substituted one or more times with substituents independently selected from $R^z$;

$R^a$ and $R^b$ are independently selected from the group consisting of hydrogen, —$C_{1-6}$ alkyl, —$C_{3-10}$ cycloalkyl, heterocyclyl, phenyl, heteroaryl, —$C_{1-4}$ alkylene-$C_{3-10}$ cycloalkyl, —$C_{1-4}$ alkylene-heterocyclyl, —$C_{1-4}$ alkylene-phenyl, and —$C_{1-4}$ alkylene-heteroaryl, where the alkyl, alkylene, cycloalkyl, heterocyclyl, phenyl, and heteroaryl groups are optionally substituted one or more times with substituents independently selected from $R^z$; or, if $R^a$ and $R^b$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, azepano, 2-oxo-pyrrolidin-1-yl, 2-oxo-imidazolidin-1-yl, 2-oxo-oxazolidin-3-yl, 2-oxo-thiazolidin-3-yl, 3-oxo-isoxazolidin-2-yl, 3-oxo-isothiazolidin-3-yl, 2-oxo-piperidin-1-yl, 2-oxo-piperazin-1-yl, 3-oxo-morpholin-4-yl, 3-oxo-thiomorpholin-4-yl, 2-oxo-azepan-1-yl, 1H-pyrrol-1-yl, 3-pyrrolin-1-yl, imidazol-1-yl, 2-imidazolin-1-yl, 1H-pyrazol-1-yl, 2-pyrazolin-1-yl, 1,2,3-triazol-1-yl, 1,2,4-triazol-1-yl, and tetrazol-1-yl, where each ring is optionally substituted one or more times with substituents independently selected from $R^z$;

$R^c$ and $R^d$ are independently selected from the group consisting of hydrogen, —$C_{1-6}$ alkyl, —$C_{3-10}$ cycloalkyl, heterocyclyl, phenyl, heteroaryl, —$C_{1-4}$ alkylene-$C_{3-10}$ cycloalkyl, —$C_{1-4}$ alkylene-heterocyclyl, —$C_{1-4}$ alkylene-phenyl, and —$C_{1-4}$ alkylene-heteroaryl, where the alkyl, alkylene, cycloalkyl, heterocyclyl, phenyl, and heteroaryl groups are optionally substituted one or more times with substituents independently selected from $R^y$; or, if $R^c$ and $R^d$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, azepano, 2-oxo-pyrrolidin-1-yl, 2-oxo-imidazolidin-1-yl, 2-oxo-oxazolidin-3-yl, 2-oxo-thiazolidin-3-yl, 3-oxo-isoxazolidin-2-yl, 3-oxo-isothiazolidin-3-yl, 2-oxo-piperidin-1-yl, 2-oxo-piperazin-1-yl, 3-oxo-morpholin-4-yl, 3-oxo-thiomorpholin-4-yl, 2-oxo-azepan-1-yl, 1H-pyrrol-1-yl, 3-pyrrolin-1-yl, imidazol-1-yl, 2-imidazolin-1-yl, 1H-pyrazol-1-yl, 2-pyrazolin-1-yl, 1,2,3-triazol-1-yl, 1,2,4-triazol-1-yl, and tetrazol-1-yl, where each ring is optionally substituted one or more times with substituents independently selected from $R^y$;

$R^e$ and $R^f$ are independently selected from the group consisting of hydrogen, —$C_{1-6}$ alkyl, —$C_{3-10}$ cycloalkyl, heterocyclyl, phenyl, 1-naphthyl, 2-naphthyl, heteroaryl, —$C_{1-4}$ alkylene-$C_{3-10}$ cycloalkyl, —$C_{1-4}$ alkylene-heterocyclyl, —$C_{1-4}$ alkylene-phenyl, and —$C_{1-4}$ alkylene-heteroaryl, where the alkyl, alkylene, cycloalkyl, heterocyclyl, phenyl, naphthyl, and heteroaryl groups are optionally substituted one or more times with substituents independently selected from the group consisting of halogen, methyl, ethyl, isopropyl, —$CF_3$, —$OCH_3$, —$OCH_2CH_3$, —$OCH(CH_3)_2$, —$OCF_3$, —$OCH_2CF_3$; or, if $R^e$ and $R^f$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, azepano, 2-oxo-pyrrolidin-1-yl, 2-oxo-imidazolidin-1-yl, 2-oxo-oxazolidin-3-yl, 2-oxo-thiazolidin-3-yl, 3-oxo-isoxazolidin-2-yl, 3-oxo-isothiazolidin-3-yl, 2-oxo-piperidin-1-yl, 2-oxo-piperazin-1-yl, 3-oxo-morpholin-4-yl, 3-oxo-thiomorpholin-4-yl, 2-oxo-azepan-1-yl, 1H-pyrrol-1-yl, 3-pyrrolin-1-yl, imidazol-1-yl, 2-imidazolin-1-yl, 1H-pyrazol-1-yl, 2-pyrazolin-1-yl, 1,2,3-triazol-1-yl, 1,2,4-triazol-1-yl, and tetrazol-1-yl, where each ring is optionally substituted one or more times with substituents independently selected from the group consisting of halogen, methyl, ethyl, isopropyl, —$CF_3$, —$OCH_3$, —$OCH_2CH_3$, —$OCH(CH_3)_2$, —$OCF_3$, —$OCH_2CF_3$;

$R^y$ is
a) -halogen,
b) —$NR^eR^f$,
c) —O—$R^e$,
d) —S—$R^e$,
e) —$S(O)_2$—$R^e$,
f) -cyano,
g) —C(O)—$R^e$,
h) —C(O)—O—$R^e$,
i) —C(O)$NR^eR^f$,
j) —$C_{1-6}$ alkyl, optionally substituted one or more times with substituents selected independently from the group consisting of halogen and —OH,
k) -heterocyclyl, optionally substituted one or more times with substituents selected independently from the group consisting of halogen and —OH,
l) —$C_{3-10}$ cycloalkyl, optionally substituted one or more times with substituents selected independently from the group consisting of halogen and —OH,
m) —$CF_3$,
n) —$OCF_3$,
o) -phenyl, optionally substituted one or more times with substituents selected independently from the group consisting of halogen and —OH, or
p) -heteroaryl; optionally substituted one or more times with substituents selected independently from the group consisting of halogen and —OH;

$R^z$ is
a) -halogen,
b) —$NR^eR^f$,
c) —O—$R^e$,
d) —S—$R^e$,
e) —$S(O)_2$—$R^e$,
f) -cyano,
g) —C(O)—$R^e$,
h) —C(O)—O—$R^e$,
i) —C(O)$NR^eR^f$,
j) —$C_{1-6}$ alkyl, optionally substituted one or more times with halogen,
k) -heterocyclyl, optionally substituted one or more times with halogen,
l) —$C_{3-10}$ cycloalkyl, optionally substituted one or more times with halogen,
m) —$CF_3$,
n) —$OCF_3$,
o) -phenyl, optionally substituted one or more times with halogen, or
p) -heteroaryl; optionally substituted one or more times with halogen; and w is an integer from 0 to 2;
wherein at least one of $R^2$ and $R^3$ is not —H, or a tautomer of any of the foregoing.

Embodiment 2

A compound according to embodiment 1, wherein
$R^y$ is
a) -halogen,
b) —$NR^eR^f$,
c) —O—$R^e$,
d) —S—$R^e$,
e) —$S(O)_2$—$R^e$,
f) -cyano,
g) —C(O)—$R^e$,
h) —C(O)—O—$R^e$,
i) —C(O)$NR^eR^f$,
j) —$C_{1-6}$ alkyl, optionally substituted one or more times with halogen,
k) -heterocyclyl, optionally substituted one or more times with halogen,
l) —$C_{3-10}$ cycloalkyl, optionally substituted one or more times with halogen,
m) —$CF_3$,
n) —$OCF_3$,
o) -phenyl, optionally substituted one or more times with halogen, or
p) -heteroaryl; optionally substituted one or more times with halogen.

Embodiment 3

A compound according to embodiment 2, wherein
$R^1$ is —H, halogen, methyl, ethyl, isopropyl, —CN, —$CF_3$, —$CH_2CF_3$, —$OCF_3$, —$OCH_3$, —$OCH_2CH_3$, —$SCH_3$, —$SO_2$—$CH_3$, —$NH_2$, —NH—$CH_3$, —$N(CH_3)_2$, —NH—$CH_2CH_3$, —$N(CH_3)(CH_2CH_3)$, —$N(CH_2CH_3)_2$, —$CO_2H$, —C(O)—O—$CH_3$, —C(O)—O—$CH_2CH_3$, —C(O)—$NH_2$, —C(O)—NH—$CH_3$, —C(O)—$N(CH_3)_2$, —C(O)—$CH_3$, —O—C(O)—$CH_3$, —OH, or —SH.

Embodiment 4

A compound according to embodiment 3, wherein
$R^1$ is hydrogen, halogen, —$CH_3$, —$OCH_3$, —$CF_3$, or —$OCF_3$.

Embodiment 5

A compound according to embodiment 4, wherein
$R^1$ is hydrogen.

Embodiment 6

A compound according to any one of embodiments 2 to 5, wherein
$R^4$ is —H, halogen, methyl, ethyl, isopropyl, —CN, —$CF_3$, —$CH_2CF_3$, —$OCF_3$, —$OCH_3$, —$OCH_2CH_3$, —$SCH_3$, —$SO_2$—$CH_3$, —$NH_2$, —NH—$CH_3$, —$N(CH_3)_2$, —NH—$CH_2CH_3$, —$N(CH_3)(CH_2CH_3)$, —$N(CH_2CH_3)_2$, —$CO_2H$, —C(O)—O—$CH_3$, —C(O)—O—$CH_2CH_3$, —C(O)—$NH_2$, —C(O)—NH—$CH_3$, —C(O)—$N(CH_3)_2$, —C(O)—$CH_3$, —O—C(O)—$CH_3$, —OH, or —SH.

Embodiment 7

A compound according to embodiment 6, wherein
$R^4$ is hydrogen, halogen, —$CH_3$, —$OCH_3$, —$CF_3$, or —$OCF_3$.

Embodiment 8

A compound according to any one of embodiments 2 to 7, wherein
$R^4$ is hydrogen.

Embodiment 9

A compound according to any one of embodiments 2 to 8, wherein
$R^5$ is hydrogen.

Embodiment 10

A compound according to any one of embodiments 2 to 9, wherein
$R^6$ is hydrogen, halogen, methyl, ethyl, isopropyl, —CN, —$CF_3$, —$CH_2CF_3$, —$OCF_3$, —$OCH_3$, —$OCH_2CH_3$, —$SCH_3$, —$SO_2$—$CH_3$, —$NH_2$, —NH—$CH_3$, —$N(CH_3)_2$, —NH—$CH_2CH_3$, —$N(CH_3)(CH_2CH_3)$, —$N(CH_2CH_3)_2$, —$CO_2H$, —C(O)—O—$CH_3$, —C(O)—O—$CH_2CH_3$, —C(O)—$NH_2$, —C(O)—NH—$CH_3$, —C(O)—$N(CH_3)_2$, —C(O)—$CH_3$, —O—C(O)—$CH_3$, —OH, or —SH.

Embodiment 11

A compound according to embodiment 10, wherein
$R^6$ is hydrogen, halogen, —$CH_3$, —$OCH_3$, —$CF_3$, or —$OCF_3$.

Embodiment 12

A compound according to embodiments 11, wherein
$R^6$ is hydrogen.

Embodiment 13

A compound according to any one of embodiments 2 to 12, wherein
$R^2$ is —H, halogen, methyl, ethyl, isopropyl, —CN, —$CF_3$, —$CH_2CF_3$, —$OCF_3$, —$OCH_3$, —$OCH_2CH_3$, —$SCH_3$, —$SO_2$—$CH_3$, —$NH_2$, —NH—$CH_3$, —$N(CH_3)_2$, —NH—$CH_2CH_3$, —$N(CH_3)(CH_2CH_3)$, —$N(CH_2CH_3)_2$, —$CO_2H$, —C(O)—O—$CH_3$, —C(O)—O—$CH_2CH_3$, —C(O)—$NH_2$, —C(O)—NH—$CH_3$, —C(O)—$N(CH_3)_2$, —C(O)—$CH_3$, —O—C(O)—$CH_3$, —OH, —SH, —O—$C_{1-4}$ alkylene-phenyl, —S—$C_{1-4}$ alkylene-phenyl, —$S(O)_2$—$C_{1-4}$ alkylene-phenyl, —O-phenyl, —S-phenyl, —$S(O)_2$-phenyl, phenyl, —O—$C_{1-4}$ alkylene-heteroaryl, —S—$C_{1-4}$ alkylene-heteroaryl, —$S(O)_2$—$C_{1-4}$ alkylene-heteroaryl, —O-heteroaryl, —S-heteroaryl, —$S(O)_2$-heteroaryl, heteroaryl, —O—$C_{1-4}$ alkylene-$C_{3-10}$ cycloalkyl, —S—$C_{1-4}$ alkylene-$C_{3-10}$ cycloalkyl, —$S(O)_2$—$C_{1-4}$ alkylene-$C_{3-10}$ cycloalkyl, —O—$C_{3-10}$ cycloalkyl, —S—$C_{3-10}$ cycloalkyl, —$S(O)_2$—$C_{3-10}$ cycloalkyl, or —$C_{3-10}$ cycloalkyl, where the alkylene, phenyl, heteroaryl, and cycloalkyl groups are each optionally substituted one or more times with substituents independently selected from $R^z$.

Embodiment 14

A compound according to embodiment 13, wherein
$R^2$ is —H.

Embodiment 15

A compound according to embodiment 13, wherein
$R^2$ is —O—$C_{1-4}$ alkylene-phenyl, —S—$C_{1-4}$ alkylene-phenyl, —$S(O)_2$—$C_{1-4}$ alkylene-phenyl, —O-phenyl, —S-phenyl, —$S(O)_2$-phenyl, phenyl, —O—$C_{1-4}$ alkylene-heteroaryl, —S—$C_{1-4}$ alkylene-heteroaryl, —$S(O)_2$—$C_{1-4}$ alkylene-heteroaryl, —O-heteroaryl, —S-heteroaryl, —$S(O)_2$-heteroaryl, heteroaryl, —O—$C_{1-4}$ alkylene-$C_{3-10}$ cycloalkyl, —S—$C_{1-4}$ alkylene-$C_{3-10}$ cycloalkyl, —$S(O)_2$—$C_{1-4}$ alkylene-$C_{3-10}$ cycloalkyl, —O—$C_{3-10}$ cycloalkyl, —S—$C_{3-10}$ cycloalkyl, —$S(O)_2$—$C_{3-10}$ cycloalkyl, or —$C_{3-10}$ cycloalkyl, where the alkylene, phenyl, heteroaryl, and cycloalkyl groups are each optionally substituted one or more times with substituents independently selected from $R^z$.

Embodiment 16

A compound according to embodiment 13, wherein
$R^2$ is —O—$CH_2$-phenyl, phenyl, or —$C_{3-10}$ cycloalkyl, where the phenyl and cycloalkyl groups are each optionally substituted one or more times with substituents independently selected from $R^z$.

Embodiment 17

A compound according to embodiment 13, wherein
$R^2$ is —O—$CH_2$-phenyl, where the phenyl group is optionally substituted one or more times with substituents independently selected from the group consisting of halogen, —$CF_3$, —O—$CF_3$, —$CH_3$, and —$OCH_3$.

Embodiment 18

A compound according to embodiment 13, wherein
$R^2$ is phenyl, where the phenyl group is optionally substituted one or more times with substituents independently selected from the group consisting of halogen, —$CF_3$, —O—$CF_3$, —$CH_3$, and —$OCH_3$.

Embodiment 19

A compound according to embodiment 13, wherein
$R^2$ is —$C_{3-10}$ cycloalkyl, where the cycloalkyl group is optionally substituted one or more times with substituents independently selected from the group consisting of halogen, —$CF_3$, —O—$CF_3$, —$CH_3$, and —$OCH_3$.

Embodiment 20

A compound according to embodiment 13, wherein
$R^2$ is cyclohexyl or cyclopentyl, where each cycloalkyl group is optionally substituted one or more times with substituents independently selected from the group consisting of halogen, —$CF_3$, —O—$CF_3$, —$CH_3$, and —$OCH_3$.

Embodiment 21

A compound according to embodiment 13, wherein
$R^2$ is heteroaryl, where the heteroaryl group is optionally substituted one or more times with substituents independently selected from the group consisting of halogen, —$CF_3$, —O—$CF_3$, —$CH_3$, and —$OCH_3$.

Embodiment 22

A compound according to embodiment 13, wherein
$R^2$ is 1H-pyrrol-1-yl, 1H-pyrrol-2-yl, 1H-pyrrol-3-yl, furan-2-yl, furan-3-yl, thiophen-2-yl, thiophen-3-yl, 1H-imidazol-1-yl, 1H-imidazol-2-yl, 1H-imidazol-4-yl, 1H-imidazol-5-yl, 1H-pyrazol-1-yl, 1H-pyrazol-3-yl, 1H-pyrazol-4-yl, 1H-pyrazol-5-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl, 1H-1,2,4-triazol-5-yl, furazan-3-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, and 1,3,5-triazin-2-yl, where each heteroaryl group is optionally substituted one or more times with substituents independently selected from the group consisting of halogen, —$CF_3$, —O—$CF_3$, —$CH_3$, and —$OCH_3$.

Embodiment 23

A compound according to embodiment 13, wherein
$R^2$ is 1H-pyrrol-2-yl, 1H-pyrrol-3-yl, furan-2-yl, and thiophen-2-yl, where each heteroaryl group is optionally substituted one or more times with substituents independently selected from the group consisting of halogen, —$CF_3$, —O—$CF_3$, —$CH_3$, and —$OCH_3$.

Embodiment 24

A compound according to any one of embodiments 2 to 23, wherein
$R^3$ is —H, halogen, methyl, ethyl, isopropyl, —CN, —$CF_3$, —$CH_2CF_3$, —$OCF_3$, —$OCH_3$, —$OCH_2CH_3$, —$SCH_3$, —$SO_2$—$CH_3$, —$NH_2$, —NH—$CH_3$, —N($CH_3$)$_2$, —NH—$CH_2CH_3$, —N($CH_3$)($CH_2CH_3$), —N($CH_2CH_3$)$_2$, —$CO_2H$, —C(O)—O—$CH_3$, —C(O)—O—$CH_2CH_3$, —C(O)—$NH_2$, —C(O)—NH—$CH_3$, —C(O)—N($CH_3$)$_2$, —C(O)—$CH_3$, —O—C(O)—$CH_3$, —OH, —SH, —O—$C_{1-4}$ alkylene-phenyl, —S—$C_{1-4}$ alkylene-phenyl, —S(O)$_2$—$C_{1-4}$ alkylene-phenyl, —O-phenyl, —S-phenyl, —S(O)$_2$-phenyl, phenyl, —O—$C_{1-4}$ alkylene-heteroaryl, —S—$C_{1-4}$ alkylene-heteroaryl, —S(O)$_2$—$C_{1-4}$ alkylene-heteroaryl, —O-heteroaryl, —S-heteroaryl, —S(O)$_2$-heteroaryl, heteroaryl, —O—$C_{1-4}$ alkylene-$C_{3-10}$ cycloalkyl, —S—$C_{1-4}$ alkylene-$C_{3-10}$ cycloalkyl, —S(O)$_2$—$C_{1-4}$ alkylene-$C_{3-10}$ cycloalkyl, —O—$C_{3-10}$ cycloalkyl, —S—$C_{3-10}$ cycloalkyl, —S(O)$_2$—$C_{3-10}$ cycloalkyl, or $C_{3-10}$ cycloalkyl, where the alkylene, phenyl, heteroaryl, and cycloalkyl groups are each optionally substituted one or more times with substituents independently selected from $R^z$.

Embodiment 25

A compound according to embodiment 24, wherein
$R^3$ is hydrogen.

Embodiment 26

A compound according to embodiment 24, wherein
$R^3$ is —O—$C_{1-4}$ alkylene-phenyl, —S—$C_{1-4}$ alkylene-phenyl, —S(O)$_2$—$C_{1-4}$ alkylene-phenyl, —O-phenyl, —S-phenyl, —S(O)$_2$-phenyl, phenyl, —O—$C_{1-4}$ alkylene-heteroaryl, —S—$C_{1-4}$ alkylene-heteroaryl, —S(O)$_2$ —$C_{1-4}$ alkylene-heteroaryl, —O-heteroaryl, —S-heteroaryl, —S(O)$_2$-heteroaryl, heteroaryl, —O—$C_{1-4}$ alkylene-$C_{3-10}$ cycloalkyl, —S—$C_{1-4}$ alkylene-$C_{3-10}$ cycloalkyl, —S(O)$_2$—$C_{1-4}$ alkylene-$C_{3-10}$ cycloalkyl, —O—$C_{3-10}$ cycloalkyl, —S—$C_{3-10}$ cycloalkyl, —S(O)$_2$—$C_{3-10}$ cycloalkyl, or —$C_{3-10}$ cycloalkyl, where the alkylene, phenyl, heteroaryl, and cycloalkyl groups are each optionally substituted one or more times with substituents independently selected from $R^z$.

Embodiment 27

A compound according to embodiment 24, wherein
$R^3$ is —O—$CH_2$-phenyl, phenyl, or —$C_{3-10}$ cycloalkyl, where the phenyl and cycloalkyl groups are each optionally substituted one or more times with substituents independently selected from $R^z$.

Embodiment 28

A compound according to embodiment 24, wherein
$R^3$ is —O—$CH_2$-phenyl, where the phenyl group is optionally substituted one or more times with substituents independently selected from the group consisting of halogen, —$CF_3$, —O—$CF_3$, —$CH_3$, and —$OCH_3$.

Embodiment 29

A compound according to embodiment 24, wherein
$R^3$ is phenyl, where the phenyl group is optionally substituted one or more times with substituents independently selected from the group consisting of halogen, —$CF_3$, —O—$CF_3$, —$CH_3$, and —$OCH_3$.

Embodiment 30

A compound according to embodiment 24, wherein
$R^3$ is —$C_{3-10}$ cycloalkyl, where the cycloalkyl group is optionally substituted one or more times with substituents independently selected from the group consisting of halogen, —$CF_3$, —O—$CF_3$, —$CH_3$, and —$OCH_3$.

Embodiment 31

A compound according to embodiment 24, wherein
$R^3$ is cyclohexyl or cyclopentyl, where each cycloalkyl group is optionally substituted one or more times with substituents independently selected from the group consisting of halogen, —$CF_3$, —O—$CF_3$, —$CH_3$, and —$OCH_3$.

Embodiment 32

A compound according to embodiment 24, wherein
$R^3$ is heteroaryl, where the heteroaryl group is optionally substituted one or more times with substituents independently selected from the group consisting of halogen, —$CF_3$, —O—$CF_3$, —$CH_3$, and —$OCH_3$.

Embodiment 33

A compound according to embodiment 24, wherein
$R^3$ is 1H-pyrrol-1-yl, 1H-pyrrol-2-yl, 1H-pyrrol-3-yl, furan-2-yl, furan-3-yl, thiophen-2-yl, thiophen-3-yl, 1H-imidazol-1-yl, 1H-imidazol-2-yl, 1H-imidazol-4-yl, 1H-imidazol-5-yl, 1H-pyrazol-1-yl, 1H-pyrazol-3-yl, 1H-pyrazol-4-yl, 1H-pyrazol-5-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl, 1H-1,2,4-triazol-5-yl, furazan-3-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, and 1,3,5-triazin-2-yl, where each heteroaryl group is optionally substituted one or more times with substituents independently selected from the group consisting of halogen, —$CF_3$, —O—$CF_3$, —$CH_3$, and —$OCH_3$.

Embodiment 34

A compound according to embodiment 24, wherein
$R^3$ is 1H-pyrrol-2-yl, 1H-pyrrol-3-yl, furan-2-yl, and thiophen-2-yl, where each heteroaryl group is optionally substituted one or more times with substituents independently selected from the group consisting of halogen, —$CF_3$, —O—$CF_3$, —$CH_3$, and —$OCH_3$.

Embodiment 35

A compound according to any one of embodiments 2 to 34, wherein
$R^8$ is —H, halogen, methyl, ethyl, isopropyl, —CN, —$CF_3$, —$CH_2CF_3$, —$OCF_3$, —$OCH_3$, —$OCH_2CH_3$, —$SCH_3$, —$SO_2$—$CH_3$, —$NH_2$, —NH—$CH_3$, —$N(CH_3)_2$, —NH—$CH_2CH_3$, —$N(CH_3)(CH_2CH_3)$, —$N(CH_2CH_3)_2$, —$CO_2H$, —C(O)—O—$CH_3$, —C(O)—O—$CH_2CH_3$, —C(O)—$NH_2$, —C(O)—NH—$CH_3$, —C(O)—$N(CH_3)_2$, —C(O)—$CH_3$, —O—C(O)—$CH_3$, —OH, or —SH.

Embodiment 36

A compound according to embodiment 35, wherein
$R^8$ is halogen, —$CH_3$, —$OCH_3$, —$CF_3$, or —$OCF_3$.

Embodiment 37

A compound according to embodiment 35, wherein
$R^8$ is —$NH_2$, —NH—$CH_3$, —$N(CH_3)_2$, —NH—$CH_2CH_3$, —$N(CH_3)(CH_2CH_3)$, or —$N(CH_2CH_3)_2$.

Embodiment 38

A compound according to embodiments 35, wherein
$R^9$ is —H.

Embodiment 39

A compound according to any one of embodiments 2 to 38, wherein
$R^9$ is —H, halogen, methyl, ethyl, isopropyl, —CN, —$CF_3$, —$CH_2CF_3$, —$OCF_3$, —$OCH_3$, —$OCH_2CH_3$, —$SCH_3$, —$SO_2$—$CH_3$, —$NH_2$, —NH—$CH_3$, —$N(CH_3)_2$, —NH—$CH_2CH_3$, —$N(CH_3)(CH_2CH_3)$, —$N(CH_2CH_3)_2$, —$CO_2H$, —C(O)—O—$CH_3$, —C(O)—O—$CH_2CH_3$, —C(O)—$NH_2$, —C(O)—NH—$CH_3$, —C(O)—$N(CH_3)_2$, —C(O)—$CH_3$, —O—C(O)—$CH_3$, —OH, or —SH.

Embodiment 40

A compound according to embodiment 39, wherein
$R^9$ is halogen, —$CH_3$, —$OCH_3$, —$CF_3$, or —$OCF_3$.

Embodiment 41

A compound according to embodiment 39, wherein
$R^9$ is —$NH_2$, —NH—$CH_3$, —$N(CH_3)_2$, —NH—$CH_2CH_3$, —$N(CH_3)(CH_2CH_3)$, or —$N(CH_2CH_3)_2$.

Embodiment 42

A compound according to embodiment 39, wherein
$R^9$ is —H.

Embodiment 43

A compound according to any one of embodiments 2 to 42, wherein
$R^7$ is not —H.

Embodiment 44

A compound according to any one of embodiments 2 to 42, wherein
$R^7$ is halogen, —$C_{1-6}$ alkyl, —$C_{1-4}$ alkylene-$C_{3-10}$ cycloalkyl, —$C_{1-4}$ alkylene-heterocyclyl, —O—$R^c$, —$NR^cR^d$, —O—$C_{1-6}$ alkylene-O—$R^c$, or O—$C_{1-6}$ alkylene-$NR^cR^d$, where the alkyl, alkylene, and cycloalkyl groups are optionally substituted one or more times with substituents independently selected from $R^y$.

Embodiment 45

A compound according to embodiment 44, wherein
$R^7$ is fluoro or chloro.

Embodiment 46

A compound according to embodiment 44, wherein
$R^7$ is —$C_{1-6}$ alkyl optionally substituted one or more times with substituents independently selected from $R^y$.

Embodiment 47

A compound according to embodiment 44, wherein
$R^7$ is —$C_{1-6}$ alkyl optionally substituted one or more times with halogen, —$OCH_3$, —$OCH_2CH_3$, —$OCF_3$, or —$OCH_2CF_3$.

Embodiment 48

A compound according to embodiment 44, wherein
$R^7$ is —$C_{1-6}$ alkyl optionally substituted one or more times with halogen.

Embodiment 49

A compound according to embodiment 44, wherein
$R^7$ is methyl, ethyl, isopropyl, n-propyl, isobutyl, n-butyl, sec-butyl, or tert-butyl.

Embodiment 50

A compound according to embodiment 44, wherein
$R^7$ is methyl, ethyl, or isopropyl.

Embodiment 51

A compound according to embodiment 44, wherein
$R^7$ is methyl.

Embodiment 52

A compound according to embodiment 44, wherein
$R^7$ is —O—$R^c$.

Embodiment 53

A compound according to embodiment 44, wherein
$R^7$ is —NH—$R^c$.

Embodiment 54

A compound according to embodiment 44, wherein
$R^7$ is —N(CH$_3$)—$R^c$.

Embodiment 55

A compound according to any one of embodiments 52 to 54, wherein
$R^c$ is methyl, ethyl, n-propyl, isopropyl, n-butyl, isobutyl, sec-butyl, or tert-butyl.

Embodiment 56

A compound according to any one of embodiments 52 to 54, wherein
$R^c$ is -phenyl, —CH$_2$-phenyl, or —(CH$_2$)$_2$-phenyl, where the phenyl groups are optionally substituted one or more times with substituents independently selected from the group consisting of halogen, methyl, ethyl, isopropyl, —CF$_3$, —CH$_2$CF$_3$, —OCH$_3$, —OCF$_3$, —OCH$_2$CH$_3$, —NH—CH$_3$, —N(CH$_3$)$_2$, —NH—CH$_2$CH$_3$, —N(CH$_3$)(CH$_2$CH$_3$), and —N(CH$_2$CH$_3$)$_2$.

Embodiment 57

A compound according to any one of embodiments 52 to 54, wherein
$R^c$ is —CH$_2$-heteroaryl, or —(CH$_2$)$_2$-heteroaryl, where the heteroaryl groups are optionally substituted one or more times with substituents independently selected from the group consisting of halogen, methyl, ethyl, isopropyl, —CF$_3$, —CH$_2$CF$_3$, —OCH$_3$, —OCF$_3$, —OCH$_2$CH$_3$, —NH—CH$_3$, —N(CH$_3$)$_2$, —NH—CH$_2$CH$_3$, —N(CH$_3$)(CH$_2$CH$_3$), and —N(CH$_2$CH$_3$)$_2$.

Embodiment 58

A compound according to any one of embodiments 52 to 54, wherein
$R^c$ is pyrid-2-yl, pyrrol-2-yl, oxazol-2-yl, thiazol-2-yl, imidazol-2-yl, isoxazol-3-yl, and isothiazol-3-yl, where each of the named heteroaryl groups is optionally substituted one or more times with substituents independently selected from the group consisting of halogen, methyl, ethyl, isopropyl, —CF$_3$, —CH$_2$CF$_3$, —OCH$_3$, —OCF$_3$, —OCH$_2$CH$_3$, —NH—CH$_3$, —N(CH$_3$)$_2$, —NH—CH$_2$CH$_3$, —N(CH$_3$)(CH$_2$CH$_3$), and —N(CH$_2$CH$_3$)$_2$.

Embodiment 59

A compound according to any one of embodiments 52 to 54, wherein
$R^c$ is —$C_{3-10}$ cycloalkyl, —CH$_2$—$C_{3-10}$ cycloalkyl, or —(CH$_2$)$_2$—$C_{3-10}$ cycloalkyl, where the cycloalkyl groups are optionally substituted one or more times with substituents independently selected from the group consisting of halogen, methyl, ethyl, isopropyl, —CF$_3$, —CH$_2$CF$_3$, —OCH$_3$, —OCF$_3$, —OCH$_2$CH$_3$, —NH—CH$_3$, —N(CH$_3$)$_2$, —NH—CH$_2$CH$_3$, —N(CH$_3$)(CH$_2$CH$_3$), and —N(CH$_2$CH$_3$)$_2$.

Embodiment 60

A compound according to any one of embodiments 52 to 54, wherein
$R^c$ is —(CH$_2$)$_{0-2}$-cyclopropyl, —(CH$_2$)$_{0-2}$-cyclobutyl, —(CH$_2$)$_{0-2}$-cyclopentyl, —(CH$_2$)$_{0-2}$-cyclohexyl, —(CH$_2$)$_{0-2}$-1-adamantyl, —(CH$_2$)$_{0-2}$-2-adamantyl, where each of the named cycloalkyl groups is optionally substituted one or more times with substituents independently selected from the group consisting of halogen, methyl, ethyl, isopropyl, —CF$_3$, —CH$_2$CF$_3$, —OCH$_3$, —OCF$_3$, —OCH$_2$CH$_3$, —NH—CH$_3$, —N(CH$_3$)$_2$, —NH—CH$_2$CH$_3$, —N(CH$_3$)(CH$_2$CH$_3$), and —N(CH$_2$CH$_3$)$_2$.

Embodiment 61

A compound according to any one of embodiments 52 to 54, wherein
$R^c$ is —CH$_2$-heterocyclyl, or —(CH$_2$)$_2$-heterocyclyl, where the heterocyclyl groups are optionally substituted one or more times with substituents independently selected from the group consisting of halogen, methyl, ethyl, isopropyl, —CF$_3$, —CH$_2$CF$_3$, —OCH$_3$, —OCF$_3$, —OCH$_2$CH$_3$, —NH—CH$_3$, —N(CH$_3$)$_2$, —NH—CH$_2$CH$_3$, —N(CH$_3$)(CH$_2$CH$_3$), —N(CH$_2$CH$_3$)$_2$, and —C(O)—O—C(CH$_3$)$_3$.

Embodiment 62

A compound according to embodiment 61, wherein
the heterocyclyl group is selected from the group consisting of tetrahydrofuran-2-yl, tetrahydrofuran-3-yl, pyrrolidin-1-yl, pyrrolidin-2-yl, pyrrolidin-3-yl, tetrahydrothiophen-2-yl, tetrahydrothiophen-3-yl, tetrahydropyran-2-yl, tetrahydropyran-3-yl, tetrahydropyran-4-yl, piperidin-1-yl, piperidin-2-yl, piperidin-3-yl, piperidin-4-yl, piperazin-1-yl, piperazin-2-yl, morpholin-2-yl, morpholin-3-yl, morpholin-4-yl, thiomorpholin-2-yl, thiomorpholin-3-yl, and thiomorpholin-4-yl, where each of said heterocyclyl groups is optionally substituted one or more times with substituents independently selected from the group consisting of halogen, methyl, ethyl, isopropyl, —CF$_3$, —CH$_2$CF$_3$, —OCH$_3$, —OCF$_3$, —OCH$_2$CH$_3$, —NH—CH$_3$, —N(CH$_3$)$_2$, —NH—CH$_2$CH$_3$, —N(CH$_3$)(CH$_2$CH$_3$), —N(CH$_2$CH$_3$)$_2$, and —C(O)—O—C(CH$_3$)$_3$.

Embodiment 63

A compound according to any one of embodiments 52 to 54, wherein
R$^c$ is -heterocyclyl, where the heterocyclyl group is optionally substituted one or more times with substituents independently selected from the group consisting of halogen, methyl, ethyl, isopropyl, —CF$_3$, —CH$_2$CF$_3$, —OCH$_3$, —OCF$_3$, —OCH$_2$CH$_3$, —NH—CH$_3$, —N(CH$_3$)$_2$, —NH—CH$_2$CH$_3$, —N(CH$_3$)(CH$_2$CH$_3$), —N(CH$_2$CH$_3$)$_2$, and —C(O)—O—C(CH$_3$)$_3$.

Embodiment 64

A compound according to embodiment 63, wherein
the heterocyclyl group is selected from the group consisting of tetrahydrofuran-2-yl, tetrahydrofuran-3-yl, pyrrolidin-2-yl, pyrrolidin-3-yl, tetrahydrothiophen-2-yl, tetrahydrothiophen-3-yl, tetrahydropyran-2-yl, tetrahydropyran-3-yl, tetrahydropyran-4-yl, piperidin-2-yl, piperidin-3-yl, piperidin-4-yl, piperazin-2-yl, morpholin-2-yl, morpholin-3-yl, thiomorpholin-2-yl, and thiomorpholin-3-yl, where each of said heterocyclyl groups is optionally substituted one or more times with substituents independently selected from the group consisting of halogen, methyl, ethyl, —CF$_3$, —CH$_2$CF$_3$, —OCH$_3$, —OCF$_3$, —OCH$_2$CH$_3$, —NH—CH$_3$, —N(CH$_3$)$_2$, —NH—CH$_2$CH$_3$, —N(CH$_3$)(CH$_2$CH$_3$), —N(CH$_2$CH$_3$)$_2$, and —C(O)—O—C(CH$_3$)$_3$.

Embodiment 65

A compound according to embodiment 44, wherein
R$^7$ is —O—(CH$_2$)$_{1-4}$—R$^y$, —O—CH(CH$_3$)R$^y$, —O—C(CH$_3$)$_2$—R$^y$, —O—CH$_2$—CH(CH$_3$)—R$^y$, —O—CH(CH$_3$)—CH$_2$—R$^y$, —O—(CH$_2$)$_2$—CH(CH$_3$)—R$^y$, —O—CH$_2$—C(CH$_3$)$_2$—R$^y$, or —O—(CH$_2$)$_{1-3}$—O—(CH$_2$)$_{1-3}$—R$^y$.

Embodiment 66

A compound according to embodiment 44, wherein
R$^7$ is —O—(CH$_2$)$_{1-4}$—R$^y$, —O—CH$_2$—CH(CH$_3$)—R$^y$, —O—(CH$_2$)$_2$—CH(CH$_3$)—R$^y$, or —O—(CH$_2$)$_{1-3}$—O—(CH$_2$)$_{1-3}$—R$^y$.

Embodiment 67

A compound according to embodiment 44, wherein
R$^7$ is —O—CH$_2$—R$^y$.

Embodiment 68

A compound according to embodiment 44, wherein
R$^7$ is —O—(CH$_2$)$_2$—R$^y$.

Embodiment 69

A compound according to embodiment 44, wherein
R$^7$ is —O—(CH$_2$)$_3$—R$^y$.

Embodiment 70

A compound according to embodiment 44, wherein
R$^7$ is —O—(CH$_2$)$_3$—R$^y$.

Embodiment 71

A compound according to embodiment 44, wherein
R$^7$ is —O—(CH$_2$)$_4$—R$^y$.

Embodiment 72

A compound according to embodiment 44, wherein
R$^7$ is —O—CH$_2$—CH(CH$_3$)—R$^y$, or —O—(CH$_2$)$_2$—CH(CH$_3$)—R$^y$.

Embodiment 73

A compound according to embodiment 44, wherein
R$^7$ is —O—(CH$_2$)$_2$—O—(CH$_2$)$_2$—R$^y$, —O—(CH$_2$)$_2$—O—CH$_2$—R$^y$, —O—(CH$_2$)$_2$—O—(CH$_2$)$_3$—R$^y$, —O—(CH$_2$)$_3$—O—CH$_2$—R$^y$, —O—(CH$_2$)$_3$—O—(CH$_2$)$_2$—R$^y$, —O—CH$_2$—O—(CH$_2$)$_2$—R$^y$, or —O—CH$_2$—O—(CH$_2$)$_3$—R$^y$.

Embodiment 74

A compound according to any one of embodiments 65 to 73, wherein
R$^y$ is —NR$^e$R$^f$ or —O—R$^e$.

Embodiment 75

A compound according to any one of embodiments 65 to 74, wherein
R$^y$ is —O—R$^e$.

Embodiment 76

A compound according to any one of embodiments 65 to 74, wherein
R$^y$ is —NR$^e$R$^f$.

Embodiment 77

A compound according to any one of embodiments 74 to 76, wherein
R$^e$ and R$^f$ are independently selected from the group consisting of hydrogen, —C$_{1-6}$ alkyl, —C$_{3-10}$ cycloalkyl, and phenyl, where the alkyl, cycloalkyl, and phenyl groups are optionally substituted one or more times with substituents independently selected from the group consisting of halogen, methyl, —CF$_3$, —OCH$_3$, and —OCF$_3$; or, if R$^e$ and R$^f$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, azepano, 2-oxo-pyrrolidin-1-yl, 2-oxo-imidazolidin-1-yl, 2-oxo-oxazolidin-3-yl, 2-oxo-thiazolidin-3-yl, 3-oxo-isoxazolidin-2-yl, 3-oxo-isothiazolidin-3-yl, 2-oxo-piperidin-1-yl, 2-oxo-piperazin-1-yl, 3-oxo-morpholin-4-yl, 3-oxo-thiomorpholin-4-yl, 2-oxo-azepan-1-yl, 1H-pyrrol-1-yl, 3-pyrrolin-1-yl, imidazol-1-yl, 2-imidazolin-1-yl, 1H-pyrazol-1-yl, 2-pyrazolin-1-yl, 1,2,3-triazol-1-yl, 1,2,4-triazol-1-yl, and tetrazol-1-yl, where each ring is optionally substituted one or more times with substituents independently selected from the group consisting of halogen, methyl, —$CF_3$, —$OCH_3$, and —$OCF_3$.

Embodiment 78

A compound according to any one of embodiments 74 to 77, wherein
$R^f$ is hydrogen; and $R^e$ is methyl, ethyl, n-propyl, isopropyl, n-butyl, sec-butyl, isobutyl, or tert-butyl, where each named alkyl group is optionally substituted one or more times with substituents independently selected from the group consisting of halogen, —$CF_3$, —$OCH_3$, and —$OCF_3$.

Embodiment 79

A compound according to any one of embodiments 74 to 77, wherein
$R^f$ is methyl; and $R^e$ is methyl, ethyl, n-propyl, isopropyl, n-butyl, sec-butyl, isobutyl, or tert-butyl, where each named alkyl group is optionally substituted one or more times with substituents independently selected from the group consisting of halogen, —$CF_3$, —$OCH_3$, and —$OCF_3$.

Embodiment 80

A compound according to embodiment 76, wherein
$NR^eR^f$ is —$N(CH_3)_2$, —$N(CH_3)(CH_2CH_3)$, —$N(CH_2CH_3)_2$, —$N(CH(CH_3)_2)_2$, —$NH_2$, —$NH(CH_3)$, —$NH(CH_2CH_3)$, —$NH(CH(CH_3)_2)$, —$NH(CH_2CH_2CH_3)$, —$NH(C(CH_3)_3)$, —$NH(CH_2CH(CH_3)_2)$, azetidino, pyrrolidino, pyrazolidino, imidazolidino, oxazolidino, isoxazolidino, thiazolidino, isothiazolidino, piperidino, piperazino, morpholino, thiomorpholino, azepano, 2-oxo-pyrrolidin-1-yl, 2-oxo-imidazolidin-1-yl, 2-oxo-oxazolidin-3-yl, 2-oxo-thiazolidin-3-yl, 3-oxo-isoxazolidin-2-yl, 3-oxo-isothiazolidin-3-yl, 2-oxo-piperidin-1-yl, 2-oxo-piperazin-1-yl, 3-oxo-morpholin-4-yl, 3-oxo-thiomorpholin-4-yl, 2-oxo-azepan-1-yl, 1H-pyrrol-1-yl, 3-pyrrolin-1-yl, imidazol-1-yl, 2-imidazolin-1-yl, 1H-pyrazol-1-yl, 2-pyrazolin-1-yl, 1,2,3-triazol-1-yl, 1,2,4-triazol-1-yl, and tetrazol-1-yl, where each ring is optionally substituted one or more times with substituents independently selected from the group consisting of halogen, methyl, —$CF_3$, —$OCH_3$, and —$OCF_3$.

Embodiment 81

A compound according to embodiment 76, wherein
$NR^eR^f$ is —$N(CH_3)_2$, —$N(CH_3)(CH_2CH_3)$, —$N(CH_2CH_3)_2$, —$N(CH(CH_3)_2)_2$, —$NH_2$, —$NH(CH_3)$, —$NH(CH_2CH_3)$, —$NH(CH(CH_3)_2)$, —$NH(CH_2CH_2CH_3)$, —$NH(C(CH_3)_3)$, or —$NH(CH_2CH(CH_3)_2)$.

Embodiment 82

A compound according to embodiment 76, wherein
$NR^eR^f$ is azetidino, pyrrolidino, pyrazolidino, imidazolidino, oxazolidino, isoxazolidino, thiazolidino, isothiazolidino, piperidino, piperazino, morpholino, thiomorpholino, azepano, 2-oxo-pyrrolidin-1-yl, 2-oxo-imidazolidin-1-yl, 2-oxo-oxazolidin-3-yl, 2-oxo-thiazolidin-3-yl, 3-oxo-isoxazolidin-2-yl, 3-oxo-isothiazolidin-3-yl, 2-oxo-piperidin-1-yl, 2-oxo-piperazin-1-yl, 3-oxo-morpholin-4-yl, 3-oxo-thiomorpholin-4-yl, 2-oxo-azepan-1-yl, 1H-pyrrol-1-yl, 3-pyrrolin-1-yl, imidazol-1-yl, 2-imidazolin-1-yl, 1H-pyrazol-1-yl, 2-pyrazolin-1-yl, 1,2,3-triazol-1-yl, 1,2,4-triazol-1-yl, and tetrazol-1-yl, where each ring is optionally substituted one or more times with substituents independently selected from the group consisting of halogen, methyl, —$CF_3$, —$OCH_3$, and —$OCF_3$.

Embodiment 83

A compound according to any one of embodiments 2 to 82, wherein
the compound is in its free (non-salted) form.

Embodiment 84

A compound according to any one of embodiments 2 to 82, wherein
the compound is in the form of a pharmaceutically acceptable salt.

Embodiment 85

A compound according to embodiment 84, wherein
the compound is in the form of a hydrochloride salt.

Embodiment 86

A compound according to any one of embodiments 1 to 85, wherein
any "heterocyclyl" group present in the compound is selected from the group consisting of: azetidin-1-yl, azetidin-2-yl, azetidin-3-yl, pyrrolidin-1-yl, pyrrolidin-2-yl, pyrrolidin-3-yl, tetrahydrofuran-2-yl, tetrahydrofuran-3-yl, tetrahydrothiophen-2-yl, tetrahydrothiophen-3-yl, pyrazolidin-1-yl, pyrazolidin-3-yl, pyrazolidin-4-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolodin-5-yl, isothiazolidin-2-yl, isothiazolidin-3-yl, isothiazolidin-4-yl, isothiazolodin-5-yl, 1,3-dioxolan-2-yl, 1,3-dioxolan-4-yl, 1,3-oxathiolan-2-yl, 1,3-oxathiolane-4-yl, 1,3-oxathiolan-5-yl, 1,2-dithiolan-3-yl, 1,2-dithiolan-4-yl, 1,3-dithiolan-2-yl, 1,3-dithiolan-4-yl, piperidin-1-yl, piperidin-2-yl, piperidin-3-yl, piperidin-4-yl, tetrahydropyran-2-yl, tetrahydropyran-3-yl, tetrahydropyran-4-yl, thian-2-yl, thian-3-yl, thian-4-yl, piperazin-1-yl, piperazin-2-yl, morpholin-2-yl, morpholin-3-yl, morpholin-4-yl, thiomorpholin-2-yl, thiomorpholin-3-yl, thiomorpholin-4-yl, 1,4-dioxan-2-yl, 1,3-dioxan-2-yl, 1,3-dioxan-4-yl, 1,3-dioxan-5-yl, 1,4-dithian-2-yl, 1,3-dithian-2-yl, 1,3-dithian-4-yl, 1,3-dithian-5-yl, 1,2-dithian-3-yl, 1,2-dithian-4-yl, azepan-1-yl, azepan-2-yl, azepan-3-yl, azepan-4-yl, and 2-oxo-pyrrolidin-1-yl, 2-oxo-imidazolidin-1-yl, 2-oxo-oxazolidin-3-yl, 2-oxo-thiazolidin-3-yl, 3-oxo-isoxazolidin-2-yl, 3-oxo-isothiazolidin-3-yl, 2-oxo-piperidin-1-yl, 2-oxo-piperazin-1-yl, 3-oxo-morpholin-4-yl, 3-oxo-thiomorpholin-4-yl, and 2-oxo-azepan-1-yl, where each of these named rings may optionally be substituted one or more times with substituents independently selected from the group consisting of halogen, —NH$_2$, cyano, —CO$_2$H, C$_{1-4}$ alkyl, C$_{3-10}$ cycloalkyl, hydroxyl, thiol, —CF$_3$, —OCF$_3$, —O—C$_{1-4}$ alkyl, —NH—C$_{1-4}$ alkyl, —N(C$_{1-4}$ alkyl)$_2$, —S—C$_{1-4}$ alkyl, —S(O)$_2$—C$_{1-4}$ alkyl, —C(O)—C$_{1-4}$ alkyl, —C(O)O—C$_{1-4}$ alkyl, —C(O)NH$_2$, —C(O)NH—C$_{1-4}$ alkyl, and —C(O)N(C$_{1-4}$ alkyl)$_2$, and where any nitrogen atom in any of these named rings may optionally be oxidized when chemically feasible, and where any sulfur atom in any of these named rings may optionally be oxidized once or twice when chemically feasible.

Embodiment 87

A compound according to any one of embodiments 1 to 86, wherein
any "heteroaryl" group present in the compound is selected from the group consisting of: 1H-pyrrol-1-yl, 1H-pyrrol-2-yl, 1H-pyrrol-3-yl, furan-2-yl, furan-3-yl, thiophen-2-yl, thiophen-3-yl, 1H-imidazol-1-yl, 1H-imidazol-2-yl, 1H-imidazol-4-yl, 1H-imidazol-5-yl, 1H-pyrazol-1-yl, 1H-pyrazol-3-yl, 1H-pyrazol-4-yl, 1H-pyrazol-5-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl, 1H-1,2,4-triazol-5-yl, furazan-3-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1H-indol-1-yl, 1H-indol-2-yl, 1H-indol-3-yl, 2H-isoindol-1-yl, 2H-isoindol-2-yl, quinolin-2-yl, quinolin-3-yl, quinolin-4-yl, isoquinolin-1-yl, isoquinolin-3-yl, isoquinolin-4-yl, benzoxazol-2-yl, benzothiazol-2-yl, 1H-benzimidazol-1-yl, 1H-benzimidazol-2-yl, benzofuran-2-yl, benzofuran-3-yl, benzothiophen-2-yl, and benzothiophen-3-yl, where each of these named rings may optionally be substituted one or more times with substituents independently selected from the group consisting of halogen, —NH$_2$, cyano, —CO$_2$H, C$_{1-4}$ alkyl, C$_{3-10}$ cycloalkyl, hydroxyl, thiol, —CF$_3$, —OCF$_3$, —O—C$_{1-4}$ alkyl, —NH—C$_{1-4}$ alkyl, —N(C$_{1-4}$ alkyl)$_2$, —S—C$_{1-4}$ alkyl, —S(O)$_2$—C$_{1-4}$ alkyl, —C(O)—C$_{1-4}$ alkyl, —C(O)O—C$_{1-4}$ alkyl, —C(O)NH$_2$, —C(O)NH—C$_{1-4}$ alkyl, —C(O)N(C$_{1-4}$ alkyl)$_2$, and phenyl.

Embodiment 88

A compound according to any one of embodiments 2 to 87, wherein R$^5$ is
hydrogen and the benzimidazole exists in the following tautomeric form:

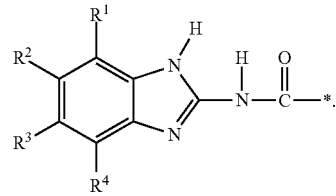

Embodiment 89

A compound according to any one of embodiments 2 to 87, wherein R$^5$ is
hydrogen and the benzimidazole exists in the following tautomeric form:

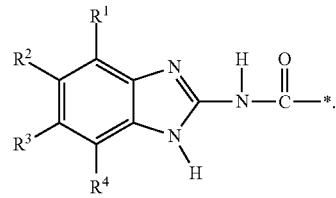

Embodiment 90

A compound according to any one of embodiments 2 to 87, wherein R$^5$ is
hydrogen and the benzimidazole exists in the following tautomeric form:

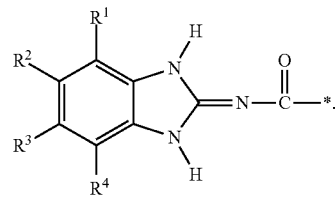

Embodiment 91

A compound according to embodiment 1.

Embodiment 92

A compound according to embodiment 91, wherein
R$^1$ is —H, halogen, methyl, ethyl, isopropyl, —CN, —CF$_3$, —CH$_2$CF$_3$, —OCF$_3$, —OCH$_3$, —OCH$_2$CH$_3$, —SCH$_3$, —SO$_2$—CH$_3$, —NH$_2$, —NH—CH$_3$, —N(CH$_3$)$_2$, —NH—CH$_2$CH$_3$, —N(CH$_3$)(CH$_2$CH$_3$), —N(CH$_2$CH$_3$)$_2$, —CO$_2$H, —C(O)—O—CH$_3$, —C(O)—O—CH$_2$CH$_3$, —C(O)—NH$_2$, —C(O)—NH—CH$_3$, —C(O)—N(CH$_3$)$_2$, —C(O)—CH$_3$, —O—C(O)—CH$_3$, —OH, or —SH.

Embodiment 93

A compound according to embodiment 92, wherein
R$^1$ is hydrogen, halogen, —CH$_3$, —OCH$_3$, —CF$_3$, or —OCF$_3$.

Embodiment 94

A compound according to embodiment 93, wherein $R^1$ is hydrogen.

Embodiment 95

A compound according to any one of embodiments 91 to 94, wherein
$R^4$ is —H, halogen, methyl, ethyl, isopropyl, —CN, —$CF_3$, —$CH_2CF_3$, —$OCF_3$, —$OCH_3$, —$OCH_2CH_3$, —$SCH_3$, —$SO_2$—$CH_3$, —$NH_2$, —NH—$CH_3$, —$N(CH_3)_2$, —NH—$CH_2CH_3$, —$N(CH_3)(CH_2CH_3)$, —$N(CH_2CH_3)_2$, —$CO_2H$, —C(O)—O—$CH_3$, —C(O)—O—$CH_2CH_3$, —C(O)—$NH_2$, —C(O)—NH—$CH_3$, —C(O)—$N(CH_3)_2$, —C(O)—$CH_3$, —O—C(O)—$CH_3$, —OH, or —SH.

Embodiment 96

A compound according to embodiment 95, wherein
$R^4$ is hydrogen, halogen, —$CH_3$, —$OCH_3$, —$CF_3$, or —$OCF_3$.

Embodiment 97

A compound according to embodiment 96, wherein $R^4$ is hydrogen.

Embodiment 98

A compound according to any one of embodiments 91 to 97, wherein
$R^5$ is hydrogen.

Embodiment 99

A compound according to any one of embodiments 91 to 98, wherein
$R^6$ is hydrogen, halogen, methyl, ethyl, isopropyl, —CN, —$CF_3$, —$CH_2CF_3$, —$OCF_3$, —$OCH_3$, —$OCH_2CH_3$, —$SCH_3$, —$SO_2$—$CH_3$, —$NH_2$, —NH—$CH_3$, —$N(CH_3)_2$, —NH—$CH_2CH_3$, —$N(CH_3)(CH_2CH_3)$, —$N(CH_2CH_3)_2$, —$CO_2H$, —C(O)—O—$CH_3$, —C(O)—O—$CH_2CH_3$, —C(O)—$NH_2$, —C(O)—NH—$CH_3$, —C(O)—$N(CH_3)_2$, —C(O)—$CH_3$, —O—C(O)—$CH_3$, —OH, or —SH.

Embodiment 100

A compound according to embodiment 99, wherein
$R^6$ is hydrogen, halogen, —$CH_3$, —$OCH_3$, —$CF_3$, or —$OCF_3$.

Embodiment 101

A compound according to embodiment 100, wherein $R^6$ is hydrogen.

Embodiment 102

A compound according to any one of embodiments 91 to 101, wherein
$R^2$ is —H, halogen, methyl, ethyl, isopropyl, —CN, —$CF_3$, —$CH_2CF_3$, —$OCF_3$, —$OCH_3$, —$OCH_2CH_3$, —$SCH_3$, —$SO_2$—$CH_3$, —$NH_2$, —NH—$CH_3$, —$N(CH_3)_2$, —NH—$CH_2CH_3$, —$N(CH_3)(CH_2CH_3)$, —$N(CH_2CH_3)_2$, —$CO_2H$, —C(O)—O—$CH_3$, —C(O)—O—$CH_2CH_3$, —C(O)—$NH_2$, —C(O)—NH—$CH_3$, —C(O)—$N(CH_3)_2$, —C(O)—$CH_3$, —O—C(O)—$CH_3$, —OH, —SH, —O—$C_{1-4}$ alkylene-phenyl, —S—$C_{1-4}$ alkylene-phenyl, —$S(O)_2$—$C_{1-4}$ alkylene-phenyl, —O-phenyl, —S-phenyl, —$S(O)_2$-phenyl, phenyl, —O—$C_{1-4}$ alkylene-heteroaryl, —S—$C_{1-4}$ alkylene-heteroaryl, —$S(O)_2$—$C_{1-4}$ alkylene-heteroaryl, —O-heteroaryl, —S-heteroaryl, —$S(O)_2$-heteroaryl, heteroaryl, —O—$C_{1-4}$ alkylene-$C_{3-10}$ cycloalkyl, —S—$C_{1-4}$ alkylene-$C_{3-10}$ cycloalkyl, —$S(O)_2$—$C_{1-4}$ alkylene-$C_{3-10}$ cycloalkyl, —O—$C_{3-10}$ cycloalkyl, —S—$C_{3-10}$ cycloalkyl, —$S(O)_2$—$C_{3-10}$ cycloalkyl, or $C_{3-10}$ cycloalkyl, where the alkylene, phenyl, heteroaryl, and cycloalkyl groups are each optionally substituted one or more times with substituents independently selected from $R^z$.

Embodiment 103

A compound according to embodiment 102, wherein $R^2$ is —H.

Embodiment 104

A compound according to embodiment 102, wherein
$R^2$ is —O—$C_{1-4}$ alkylene-phenyl, —S—$C_{1-4}$ alkylene-phenyl, —$S(O)_2$—$C_{1-4}$ alkylene-phenyl, —O-phenyl, —S-phenyl, —$S(O)_2$-phenyl, phenyl, —O—$C_{1-4}$ alkylene-heteroaryl, —S—$C_{1-4}$ alkylene-heteroaryl, —$S(O)_2$—$C_{1-4}$ alkylene-heteroaryl, —O-heteroaryl, —S-heteroaryl, —$S(O)_2$-heteroaryl, heteroaryl, —O—$C_{1-4}$ alkylene-$C_{3-10}$ cycloalkyl, —S—$C_{1-4}$ alkylene-$C_{3-10}$ cycloalkyl, —$S(O)_2$—$C_{1-4}$ alkylene-$C_{3-10}$ cycloalkyl, —O—$C_{3-10}$ cycloalkyl, —S—$C_{3-10}$ cycloalkyl, —$S(O)_2$—$C_{3-10}$ cycloalkyl, or —$C_{3-10}$ cycloalkyl, where the alkylene, phenyl, heteroaryl, and cycloalkyl groups are each optionally substituted one or more times with substituents independently selected from $R^z$.

Embodiment 105

A compound according to embodiment 102, wherein
$R^2$ is —O—$CH_2$-phenyl, phenyl, or —$C_{3-10}$ cycloalkyl, where the phenyl and cycloalkyl groups are each optionally substituted one or more times with substituents independently selected from $R^z$.

Embodiment 106

A compound according to embodiment 102, wherein
$R^2$ is —O—$CH_2$-phenyl, where the phenyl group is optionally substituted one or more times with substituents independently selected from the group consisting of halogen, —$CF_3$, —O—$CF_3$, —$CH_3$, and —$OCH_3$.

Embodiment 107

A compound according to embodiment 102, wherein
$R^2$ is phenyl, where the phenyl group is optionally substituted one or more times with substituents independently selected from the group consisting of halogen, —$CF_3$, —O—$CF_3$, —$CH_3$, and —$OCH_3$.

Embodiment 108

A compound according to embodiment 102, wherein
$R^2$ is —$C_{3-10}$ cycloalkyl, where the cycloalkyl group is optionally substituted one or more times with substituents independently selected from the group consisting of halogen, —$CF_3$, —O—$CF_3$, —$CH_3$, and —$OCH_3$.

Embodiment 109

A compound according to embodiment 102, wherein
$R^2$ is cyclohexyl or cyclopentyl, where each cycloalkyl group is optionally substituted one or more times with substituents independently selected from the group consisting of halogen, —$CF_3$, —O—$CF_3$, —$CH_3$, and —$OCH_3$.

Embodiment 110

A compound according to embodiment 102, wherein
$R^2$ is heteroaryl, where the heteroaryl group is optionally substituted one or more times with substituents independently selected from the group consisting of halogen, —$CF_3$, —O—$CF_3$, —$CH_3$, and —$OCH_3$.

Embodiment 111

A compound according to embodiment 102, wherein
$R^2$ is 1H-pyrrol-1-yl, 1H-pyrrol-2-yl, 1H-pyrrol-3-yl, furan-2-yl, furan-3-yl, thiophen-2-yl, thiophen-3-yl, 1H-imidazol-1-yl, 1H-imidazol-2-yl, 1H-imidazol-4-yl, 1H-imidazol-5-yl, 1H-pyrazol-1-yl, 1H-pyrazol-3-yl, 1H-pyrazol-4-yl, 1H-pyrazol-5-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl, 1H-1,2,4-triazol-5-yl, furazan-3-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, and 1,3,5-triazin-2-yl, where each heteroaryl group is optionally substituted one or more times with substituents independently selected from the group consisting of halogen, —$CF_3$, —O—$CF_3$, —$CH_3$, and —$OCH_3$.

Embodiment 112

A compound according to embodiment 102, wherein
$R^2$ is 1H-pyrrol-2-yl, 1H-pyrrol-3-yl, furan-2-yl, and thiophen-2-yl, where each heteroaryl group is optionally substituted one or more times with substituents independently selected from the group consisting of halogen, —$CF_3$, —O—$CF_3$, —$CH_3$, and —$OCH_3$.

Embodiment 113

A compound according to any one of embodiments 91 to 112, wherein
$R^3$ is —H, halogen, methyl, ethyl, isopropyl, —CN, —$CF_3$, —$CH_2CF_3$, —$OCF_3$, —$OCH_3$, —$OCH_2CH_3$, —$SCH_3$, —$SO_2$—$CH_3$, —$NH_2$, —NH—$CH_3$, —N($CH_3$)$_2$, —NH—$CH_2CH_3$, —N($CH_3$)($CH_2CH_3$), —N($CH_2CH_3$)$_2$, —$CO_2H$, —C(O)—O—$CH_3$, —C(O)—O—$CH_2CH_3$, —C(O)—$NH_2$, —C(O)—NH—$CH_3$, —C(O)—N($CH_3$)$_2$, —C(O)—$CH_3$, —O—C(O)—$CH_3$, —OH, —SH, —O—$C_{1-4}$ alkylene-phenyl, —S—$C_{1-4}$ alkylene-phenyl, —S(O)$_2$—$C_{1-4}$ alkylene-phenyl, —O-phenyl, —S-phenyl, —S(O)$_2$-phenyl, phenyl, —O—$C_{1-4}$ alkylene-heteroaryl, —S—$C_{1-4}$ alkylene-heteroaryl, —S(O)$_2$—$C_{1-4}$ alkylene-heteroaryl, —O-heteroaryl, —S-heteroaryl, —S(O)$_2$-heteroaryl, heteroaryl, —O—$C_{1-4}$ alkylene-$C_{3-10}$ cycloalkyl, —S—$C_{1-4}$ alkylene-$C_{3-10}$ cycloalkyl, —S(O)$_2$—$C_{1-4}$ alkylene-$C_{3-10}$ cycloalkyl, —O—$C_{3-10}$ cycloalkyl, —S—$C_{3-10}$ cycloalkyl, —S(O)$_2$—$C_{3-10}$ cycloalkyl, or $C_{3-10}$ cycloalkyl, where the alkylene, phenyl, heteroaryl, and cycloalkyl groups are each optionally substituted one or more times with substituents independently selected from $R^z$.

Embodiment 114

A compound according to embodiment 113, wherein
$R^3$ is hydrogen.

Embodiment 115

A compound according to embodiment 113, wherein
$R^3$ is —O—$C_{1-4}$ alkylene-phenyl, —S—$C_{1-4}$ alkylene-phenyl, —S(O)$_2$—$C_{1-4}$ alkylene-phenyl, —O-phenyl, —S-phenyl, —S(O)$_2$-phenyl, phenyl, —O—$C_{1-4}$ alkylene-heteroaryl, —S—$C_{1-4}$ alkylene-heteroaryl, —S(O)$_2$ —$C_{1-4}$ alkylene-heteroaryl, —O-heteroaryl, —S-heteroaryl, —S(O)$_2$-heteroaryl, heteroaryl, —O—$C_{1-4}$ alkylene-$C_{3-10}$ cycloalkyl, —S—$C_{1-4}$ alkylene-$C_{3-10}$ cycloalkyl, —S(O)$_2$—$C_{1-4}$ alkylene-$C_{3-10}$ cycloalkyl, —O—$C_{3-10}$ cycloalkyl, —S—$C_{3-10}$ cycloalkyl, —S(O)$_2$—$C_{3-10}$ cycloalkyl, or —$C_{3-10}$ cycloalkyl, where the alkylene, phenyl, heteroaryl, and cycloalkyl groups are each optionally substituted one or more times with substituents independently selected from $R^z$.

Embodiment 116

A compound according to embodiment 113, wherein
$R^3$ is —O—$CH_2$-phenyl, phenyl, or —$C_{3-10}$ cycloalkyl, where the phenyl and cycloalkyl groups are each optionally substituted one or more times with substituents independently selected from $R^z$.

Embodiment 117

A compound according to embodiment 113, wherein
$R^3$ is —O—$CH_2$-phenyl, where the phenyl group is optionally substituted one or more times with substituents independently selected from the group consisting of halogen, —$CF_3$, —O—$CF_3$, —$CH_3$, and —$OCH_3$.

Embodiment 118

A compound according to embodiment 113, wherein
$R^3$ is phenyl, where the phenyl group is optionally substituted one or more times with substituents independently selected from the group consisting of halogen, —$CF_3$, —O—$CF_3$, —$CH_3$, and —$OCH_3$.

Embodiment 119

A compound according to embodiment 113, wherein
$R^3$ is —$C_{3-10}$ cycloalkyl, where the cycloalkyl group is optionally substituted one or more times with substitu-

Embodiment 120

A compound according to embodiment 113, wherein
$R^3$ is cyclohexyl or cyclopentyl, where each cycloalkyl group is optionally substituted one or more times with substituents independently selected from the group consisting of halogen, —$CF_3$, —O—$CF_3$, —$CH_3$, and —$OCH_3$.

Embodiment 121

A compound according to embodiment 113, wherein
$R^3$ is heteroaryl, where the heteroaryl group is optionally substituted one or more times with substituents independently selected from the group consisting of halogen, —$CF_3$, —O—$CF_3$, —$CH_3$, and —$OCH_3$.

Embodiment 122

A compound according to embodiment 113, wherein
$R^3$ is 1H-pyrrol-1-yl, 1H-pyrrol-2-yl, 1H-pyrrol-3-yl, furan-2-yl, furan-3-yl, thiophen-2-yl, thiophen-3-yl, 1H-imidazol-1-yl, 1H-imidazol-2-yl, 1H-imidazol-4-yl, 1H-imidazol-5-yl, 1H-pyrazol-1-yl, 1H-pyrazol-3-yl, 1H-pyrazol-4-yl, 1H-pyrazol-5-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl, 1H-1,2,4-triazol-5-yl, furazan-3-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, and 1,3,5-triazin-2-yl, where each heteroaryl group is optionally substituted one or more times with substituents independently selected from the group consisting of halogen, —$CF_3$, —O—$CF_3$, —$CH_3$, and —$OCH_3$.

Embodiment 123

A compound according to embodiment 113, wherein
$R^3$ is 1H-pyrrol-2-yl, 1H-pyrrol-3-yl, furan-2-yl, and thiophen-2-yl, where each heteroaryl group is optionally substituted one or more times with substituents independently selected from the group consisting of halogen, —$CF_3$, —O—$CF_3$, —$CH_3$, and —$OCH_3$.

Embodiment 124

A compound according to any one of embodiments 91 to 123, wherein
$R^8$ is —H, halogen, methyl, ethyl, isopropyl, —CN, —$CF_3$, —$CH_2CF_3$, —$OCF_3$, —$OCH_3$, —$OCH_2CH_3$, —$SCH_3$, —$SO_2$—$CH_3$, —$NH_2$, —NH—$CH_3$, —$N(CH_3)_2$, —NH—$CH_2CH_3$, —$N(CH_3)(CH_2CH_3)$, —$N(CH_2CH_3)_2$, —$CO_2H$, —C(O)—O—$CH_3$, —C(O)—O—$CH_2CH_3$, —C(O)—$NH_2$, —C(O)—NH—$CH_3$, —C(O)—$N(CH_3)_2$, —C(O)—$CH_3$, —O—C(O)—$CH_3$, —OH, or —SH.

Embodiment 125

A compound according to embodiment 124, wherein
$R^8$ is halogen, —$CH_3$, —$OCH_3$, —$CF_3$, or —$OCF_3$.

Embodiment 126

A compound according to embodiment 124, wherein
$R^8$ is —$NH_2$, —NH—$CH_3$, —$N(CH_3)_2$, —NH—$CH_2CH_3$, —$N(CH_3)(CH_2CH_3)$, or —$N(CH_2CH_3)_2$.

Embodiment 127

A compound according to embodiment 124, wherein
$R^8$ is —H.

Embodiment 128

A compound according to any one of embodiments 91 to 127, wherein
$R^8$ is —H, halogen, methyl, ethyl, isopropyl, —CN, —$CF_3$, —$CH_2CF_3$, —$OCF_3$, —$OCH_3$, —$OCH_2CH_3$, —$SCH_3$, —$SO_2$—$CH_3$, —$NH_2$, —NH—$CH_3$, —$N(CH_3)_2$, —NH—$CH_2CH_3$, —$N(CH_3)(CH_2CH_3)$, —$N(CH_2CH_3)_2$, —$CO_2H$, —C(O)—O—$CH_3$, —C(O)—O—$CH_2CH_3$, —C(O)—$NH_2$, —C(O)—NH—$CH_3$, —C(O)—$N(CH_3)_2$, —C(O)—$CH_3$, —O—C(O)—$CH_3$, —OH, or —SH.

Embodiment 129

A compound according to embodiment 128, wherein
$R^9$ is halogen, —$CH_3$, —$OCH_3$, —$CF_3$, or —$OCF_3$.

Embodiment 130

A compound according to embodiment 128, wherein
$R^9$ is —$NH_2$, —NH—$CH_3$, —$N(CH_3)_2$, —NH—$CH_2CH_3$, —$N(CH_3)(CH_2CH_3)$, or —$N(CH_2CH_3)_2$.

Embodiment 131

A compound according to embodiment 128, wherein
$R^9$ is —H.

Embodiment 132

A compound according to any one of embodiments 91 to 131, wherein
$R^7$ is not —H.

Embodiment 133

A compound according to any one of embodiments 91 to 131, wherein
$R^7$ is halogen, —$C_{1-6}$ alkyl, —$C_{1-4}$ alkylene-$C_{3-10}$ cycloalkyl, —$C_{1-4}$ alkylene-heterocyclyl, —O—$R^c$, —$NR^cR^d$, —O—$C_{1-6}$ alkylene-O—$R^c$, or O—$C_{1-6}$ alkylene-$NR^cR^d$, where the alkyl, alkylene, and cycloalkyl groups are optionally substituted one or more times with substituents independently selected from $R^y$.

Embodiment 134

A compound according to embodiment 133, wherein
$R^7$ is fluoro or chloro.

Embodiment 135

A compound according to embodiment 133, wherein $R^7$ is —$C_{1-6}$ alkyl optionally substituted one or more times with substituents independently selected from $R^y$.

Embodiment 136

A compound according to embodiment 133, wherein $R^7$ is —$C_{1-6}$ alkyl optionally substituted one or more times with halogen, —$OCH_3$, —$OCH_2CH_3$, —$OCF_3$, or —$OCH_2CF_3$.

Embodiment 137

A compound according to embodiment 133, wherein $R^7$ is —$C_{1-6}$ alkyl optionally substituted one or more times with halogen.

Embodiment 138

A compound according to embodiment 133, wherein $R^7$ is methyl, ethyl, isopropyl, n-propyl, isobutyl, n-butyl, sec-butyl, or tert-butyl.

Embodiment 139

A compound according to embodiment 133, wherein $R^7$ is methyl, ethyl, or isopropyl.

Embodiment 140

A compound according to embodiment 133, wherein $R^7$ is methyl.

Embodiment 141

A compound according to embodiment 133, wherein $R^7$ is —O—$R^c$.

Embodiment 142

A compound according to embodiment 133, wherein $R^7$ is —NH—$R^c$.

Embodiment 143

A compound according to embodiment 133, wherein $R^7$ is —N($CH_3$)—$R^c$.

Embodiment 144

A compound according to any one of embodiments 141 to 143, wherein
$R^c$ is methyl, ethyl, n-propyl, isopropyl, n-butyl, isobutyl, sec-butyl, or tert-butyl.

Embodiment 145

A compound according to any one of embodiments 141 to 143, wherein
$R^c$ is -phenyl, —$CH_2$-phenyl, or —$(CH_2)_2$-phenyl, where the phenyl groups are optionally substituted one or more times with substituents independently selected from the group consisting of halogen, methyl, ethyl, isopropyl, —$CF_3$, —$CH_2CF_3$, —$OCH_3$, —$OCF_3$, —$OCH_2CH_3$, —NH—$CH_3$, —N($CH_3$)$_2$, —NH—$CH_2CH_3$, —N($CH_3$)($CH_2CH_3$), and —N($CH_2CH_3$)$_2$.

Embodiment 146

A compound according to any one of embodiments 141 to 143, wherein
$R^c$ is —$CH_2$-heteroaryl, or —$(CH_2)_2$-heteroaryl, where the heteroaryl groups are optionally substituted one or more times with substituents independently selected from the group consisting of halogen, methyl, ethyl, isopropyl, —$CF_3$, —$CH_2CF_3$, —$OCH_3$, —$OCF_3$, —$OCH_2CH_3$, —NH—$CH_3$, —N($CH_3$)$_2$, —NH—$CH_2CH_3$, —N($CH_3$)($CH_2CH_3$), and —N($CH_2CH_3$)$_2$.

Embodiment 147

A compound according to any one of embodiments 141 to 143, wherein
$R^c$ is pyrid-2-yl, pyrrol-2-yl, oxazol-2-yl, thiazol-2-yl, imidazol-2-yl, isoxazol-3-yl, and isothiazol-3-yl, where each of the named heteroaryl groups is optionally substituted one or more times with substituents independently selected from the group consisting of halogen, methyl, ethyl, isopropyl, —$CF_3$, —$CH_2CF_3$, —$OCH_3$, —$OCF_3$, —$OCH_2CH_3$, —NH—$CH_3$, —N($CH_3$)$_2$, —NH—$CH_2CH_3$, —N($CH_3$)($CH_2CH_3$), and —N($CH_2CH_3$)$_2$.

Embodiment 148

A compound according to any one of embodiments 141 to 143, wherein
$R^c$ is —$C_{3-10}$ cycloalkyl, —$CH_2$—$C_{3-10}$ cycloalkyl, or —$(CH_2)_2$—$C_{3-10}$ cycloalkyl, where the cycloalkyl groups are optionally substituted one or more times with substituents independently selected from the group consisting of halogen, methyl, ethyl, isopropyl, —$CF_3$, —$CH_2CF_3$, —$OCH_3$, —$OCF_3$, —$OCH_2CH_3$, —NH—$CH_3$, —N($CH_3$)$_2$, —NH—$CH_2CH_3$, —N($CH_3$)($CH_2CH_3$), and —N($CH_2CH_3$)$_2$.

Embodiment 149

A compound according to any one of embodiments 141 to 143, wherein
$R^c$ is —$(CH_2)_{0-2}$-cyclopropyl, —$(CH_2)_{0-2}$-cyclobutyl, —$(CH_2)_{0-2}$-cyclopentyl, —$(CH_2)_{0-2}$-cyclohexyl, —$(CH_2)_{0-2}$-1-adamantyl, —$(CH_2)_{0-2}$-2-adamantyl, where each of the named cycloalkyl groups is optionally substituted one or more times with substituents independently selected from the group consisting of halogen, methyl, ethyl, isopropyl, —$CF_3$, —$CH_2CF_3$, —$OCH_3$, —$OCF_3$, —$OCH_2CH_3$, —NH—$CH_3$, —N($CH_3$)$_2$, —NH—$CH_2CH_3$, —N($CH_3$)($CH_2CH_3$), and —N($CH_2CH_3$)$_2$.

Embodiment 150

A compound according to any one of embodiments 141 to 143, wherein
$R^c$ is —$CH_2$-heterocyclyl, or —$(CH_2)_2$-heterocyclyl, where the heterocyclyl groups are optionally substituted one or more times with substituents independently selected from the group consisting of halogen, methyl, ethyl, isopropyl, —$CF_3$, —$CH_2CF_3$, —$OCH_3$, —$OCF_3$, —$OCH_2CH_3$, —NH—$CH_3$, —N($CH_3$)$_2$, —NH—$CH_2CH_3$, —N($CH_3$)($CH_2CH_3$), —N($CH_2CH_3$)$_2$, and —C(O)—O—C($CH_3$)$_3$.

Embodiment 151

A compound according to embodiment 150, wherein
the heterocyclyl group is selected from the group consisting of tetrahydrofuran-2-yl, tetrahydrofuran-3-yl, pyrrolidin-1-yl, pyrrolidin-2-yl, pyrrolidin-3-yl, tetrahydrothiophen-2-yl, tetrahydrothiophen-3-yl, tetrahydropyran-2-yl, tetrahydropyran-3-yl, tetrahydropyran-4-yl, piperidin-1-yl, piperidin-2-yl, piperidin-3-yl, piperidin-4-yl, piperazin-1-yl, piperazin-2-yl, morpholin-2-yl, morpholin-3-yl, morpholin-4-yl, thiomorpholin-2-yl, thiomorpholin-3-yl, and thiomorpholin-4-yl, where each of said heterocyclyl groups is optionally substituted one or more times with substituents independently selected from the group consisting of halogen, methyl, ethyl, isopropyl, —$CF_3$, —$CH_2CF_3$, —$OCH_3$, —$OCF_3$, —$OCH_2CH_3$, —NH—$CH_3$, —$N(CH_3)_2$, —NH—$CH_2CH_3$, —$N(CH_3)(CH_2CH_3)$, —$N(CH_2CH_3)_2$, and —C(O)—O—$C(CH_3)_3$.

Embodiment 152

A compound according to any one of embodiments 141 to 143, wherein
$R^c$ is -heterocyclyl, where the heterocyclyl group is optionally substituted one or more times with substituents independently selected from the group consisting of halogen, methyl, ethyl, isopropyl, —$CF_3$, —$CH_2CF_3$, —$OCH_3$, —$OCF_3$, —$OCH_2CH_3$, —NH—$CH_3$, —$N(CH_3)_2$, —NH—$CH_2CH_3$, —$N(CH_3)(CH_2CH_3)$, —$N(CH_2CH_3)_2$, and —C(O)—O—$C(CH_3)_3$.

Embodiment 153

A compound according to embodiment 152, wherein
the heterocyclyl group is selected from the group consisting of tetrahydrofuran-2-yl, tetrahydrofuran-3-yl, pyrrolidin-2-yl, pyrrolidin-3-yl, tetrahydrothiophen-2-yl, tetrahydrothiophen-3-yl, tetrahydropyran-2-yl, tetrahydropyran-3-yl, tetrahydropyran-4-yl, piperidin-2-yl, piperidin-3-yl, piperidin-4-yl, piperazin-2-yl, morpholin-2-yl, morpholin-3-yl, thiomorpholin-2-yl, and thiomorpholin-3-yl, where each of said heterocyclyl groups is optionally substituted one or more times with substituents independently selected from the group consisting of halogen, methyl, ethyl, —$CF_3$, —$CH_2CF_3$, —$OCH_3$, —$OCF_3$, —$OCH_2CH_3$, —NH—$CH_3$, —$N(CH_3)_2$, —NH—$CH_2CH_3$, —$N(CH_3)(CH_2CH_3)$, —$N(CH_2CH_3)_2$, and —C(O)—O—$C(CH_3)_3$.

Embodiment 154

A compound according to embodiment 133, wherein
$R^7$ is —O—$(CH_2)_{1-4}$—$R^y$, —O—$CH(CH_3)R^y$, —O—$C(CH_3)_2$—$R^y$, —O—$CH_2$—$CH(CH_3)$—$R^y$, —O—$CH(CH_3)$—$CH_2$—$R^y$, —O—$(CH_2)_2$—$CH(CH_3)$—$R^y$, —O—$CH_2$—$C(CH_3)_2$—$R^y$, or —O—$(CH_2)_{1-3}$—O—$(CH_2)_{1-3}$—$R^y$.

Embodiment 155

A compound according to embodiment 133, wherein
$R^7$ is —O—$(CH_2)_{1-4}$—$R^y$, —O—$CH_2$—$CH(CH_3)$—$R^y$, —O—$(CH_2)_2$—$CH(CH_3)$—$R^y$, or —O—$(CH_2)_{1-3}$—O—$(CH_2)_{1-3}$—$R^y$.

Embodiment 156

A compound according to embodiment 133, wherein
$R^7$ is —O—$CH_2$—$R^y$.

Embodiment 157

A compound according to embodiment 133, wherein
$R^7$ is —O—$(CH_2)_2$—$R^y$.

Embodiment 158

A compound according to embodiment 133, wherein
$R^7$ is —O—$(CH_2)_3$—$R^y$.

Embodiment 159

A compound according to embodiment 133, wherein
$R^7$ is —O—$(CH_2)_3$—$R^y$.

Embodiment 160

A compound according to embodiment 133, wherein
$R^7$ is —O—$(CH_2)_4$—$R^y$.

Embodiment 161

A compound according to embodiment 133, wherein
$R^7$ is —O—$CH_2$—$CH(CH_3)$—$R^y$, or —O—$(CH_2)_2$—$CH(CH_3)$—$R^y$.

Embodiment 162

A compound according to embodiment 133, wherein
$R^7$ is —O—$(CH_2)_2$—O—$(CH_2)_2$—$R^y$, —O—$(CH_2)_2$—O—$CH_2$—$R^y$, —O—$(CH_2)_2$—O—$(CH_2)_3$—$R^y$, —O—$(CH_2)_3$—O—$CH_2$—$R^y$, —O—$(CH_2)_3$—O—$(CH_2)_2$—$R^y$, —O—$CH_2$—O—$(CH_2)_2$—$R^y$, or —O—$CH_2$—O—$(CH_2)_3$—$R^y$.

Embodiment 163

A compound according to any one of embodiments 154 to 162, wherein
$R^y$ is —O—$R^e$.

Embodiment 164

A compound according to any one of embodiments 154 to 163, wherein
$R^y$ is —OH.

Embodiment 165

A compound according to any one of embodiments 154 to 163, wherein
$R^y$ is —$NR^eR^f$.

Embodiment 166

A compound according to any one of embodiments 163 to 165, wherein
$R^e$ and $R^f$ are independently selected from the group consisting of hydrogen, —$C_{1-6}$ alkyl, —$C_{3-10}$ cycloalkyl, and phenyl, where the alkyl, cycloalkyl, and phenyl groups are optionally substituted one or more times with substituents independently selected from the group consisting of halogen, methyl, —$CF_3$, —$OCH_3$, and —OCF$_3$; or, if R$^e$ and R$^f$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, azepano, 2-oxo-pyrrolidin-1-yl, 2-oxo-imidazolidin-1-yl, 2-oxo-oxazolidin-3-yl, 2-oxo-thiazolidin-3-yl, 3-oxo-isoxazolidin-2-yl, 3-oxo-isothiazolidin-3-yl, 2-oxo-piperidin-1-yl, 2-oxo-piperazin-1-yl, 3-oxo-morpholin-4-yl, 3-oxo-thiomorpholin-4-yl, 2-oxo-azepan-1-yl, 1H-pyrrol-1-yl, 3-pyrrolin-1-yl, imidazol-1-yl, 2-imidazolin-1-yl, 1H-pyrazol-1-yl, 2-pyrazolin-1-yl, 1,2,3-triazol-1-yl, 1,2,4-triazol-1-yl, and tetrazol-1-yl, where each ring is optionally substituted one or more times with substituents independently selected from the group consisting of halogen, methyl, —CF$_3$, —OCH$_3$, and —OCF$_3$.

Embodiment 167

A compound according to any one of embodiments 163 to 166, wherein
R$^f$ is hydrogen; and R$^e$ is methyl, ethyl, n-propyl, isopropyl, n-butyl, sec-butyl, isobutyl, or tert-butyl, where each named alkyl group is optionally substituted one or more times with substituents independently selected from the group consisting of halogen, —CF$_3$, —OCH$_3$, and —OCF$_3$.

Embodiment 168

A compound according to any one of embodiments 163 to 166, wherein
R$^f$ is methyl; and R$^e$ is methyl, ethyl, n-propyl, isopropyl, n-butyl, sec-butyl, isobutyl, or tert-butyl, where each named alkyl group is optionally substituted one or more times with substituents independently selected from the group consisting of halogen, —CF$_3$, —OCH$_3$, and —OCF$_3$.

Embodiment 169

A compound according to embodiment 165, wherein
NR$^e$R$^f$ is —N(CH$_3$)$_2$, —N(CH$_3$)(CH$_2$CH$_3$), —N(CH$_2$CH$_3$)$_2$, —N(CH(CH$_3$)$_2$)$_2$, —NH$_2$, —NH(CH$_3$), —NH(CH$_2$CH$_3$), —NH(CH(CH$_3$)$_2$), —NH(CH$_2$CH$_2$CH$_3$), —NH(C(CH$_3$)$_3$), —NH(CH$_2$CH(CH$_3$)$_2$), azetidino, pyrrolidino, pyrazolidino, imidazolidino, oxazolidino, isoxazolidino, thiazolidino, isothiazolidino, piperidino, piperazino, morpholino, thiomorpholino, azepano, 2-oxo-pyrrolidin-1-yl, 2-oxo-imidazolidin-1-yl, 2-oxo-oxazolidin-3-yl, 2-oxo-thiazolidin-3-yl, 3-oxo-isoxazolidin-2-yl, 3-oxo-isothiazolidin-3-yl, 2-oxo-piperidin-1-yl, 2-oxo-piperazin-1-yl, 3-oxo-morpholin-4-yl, 3-oxo-thiomorpholin-4-yl, 2-oxo-azepan-1-yl, 1H-pyrrol-1-yl, 3-pyrrolin-1-yl, imidazol-1-yl, 2-imidazolin-1-yl, 1H-pyrazol-1-yl, 2-pyrazolin-1-yl, 1,2,3-triazol-1-yl, 1,2,4-triazol-1-yl, and tetrazol-1-yl, where each ring is optionally substituted one or more times with substituents independently selected from the group consisting of halogen, methyl, —CF$_3$, —OCH$_3$, and —OCF$_3$.

Embodiment 170

A compound according to embodiment 165, wherein
NR$^e$R$^f$ is —N(CH$_3$)$_2$, —N(CH$_3$)(CH$_2$CH$_3$), —N(CH$_2$CH$_3$)$_2$, —N(CH(CH$_3$)$_2$)$_2$, —NH$_2$, —NH(CH$_3$), —NH(CH$_2$CH$_3$), —NH(CH(CH$_3$)$_2$), —NH(CH$_2$CH$_2$CH$_3$), —NH(C(CH$_3$)$_3$), or —NH(CH$_2$CH(CH$_3$)$_2$).

Embodiment 171

A compound according to embodiment 165, wherein
NR$^e$R$^f$ is azetidino, pyrrolidino, pyrazolidino, imidazolidino, oxazolidino, isoxazolidino, thiazolidino, isothiazolidino, piperidino, piperazino, morpholino, thiomorpholino, azepano, 2-oxo-pyrrolidin-1-yl, 2-oxo-imidazolidin-1-yl, 2-oxo-oxazolidin-3-yl, 2-oxo-thiazolidin-3-yl, 3-oxo-isoxazolidin-2-yl, 3-oxo-isothiazolidin-3-yl, 2-oxo-piperidin-1-yl, 2-oxo-piperazin-1-yl, 3-oxo-morpholin-4-yl, 3-oxo-thiomorpholin-4-yl, 2-oxo-azepan-1-yl, 1H-pyrrol-1-yl, 3-pyrrolin-1-yl, imidazol-1-yl, 2-imidazolin-1-yl, 1H-pyrazol-1-yl, 2-pyrazolin-1-yl, 1,2,3-triazol-1-yl, 1,2,4-triazol-1-yl, and tetrazol-1-yl, where each ring is optionally substituted one or more times with substituents independently selected from the group consisting of halogen, methyl, —CF$_3$, —OCH$_3$, and —OCF$_3$.

Embodiment 172

A compound according to any one of embodiments 91 to 131, wherein
R$^7$ is methyl.

Embodiment 173

A compound according to any one of embodiments 91 to 131, wherein
R$^7$ is chloro.

Embodiment 174

A compound according to any one of embodiments 91 to 131, wherein
R$^7$ is —NHCH$_3$ or —N(CH$_3$)$_2$.

Embodiment 175

A compound according to any one of embodiments 91 to 131, wherein
R$^7$ is morpholin-4-yl, 4-methyl-piperazin-1-yl, piperazin-1-yl, or pyrrolidin-1-yl.

Embodiment 176

A compound according to any one of embodiments 91 to 131, wherein
R$^7$ is 3-(NH$_2$)-pyrrolidin-1-yl or 3-(NH$_2$)-piperidin-1-yl.

Embodiment 177

A compound according to any one of embodiments 91 to 131, wherein
R$^7$ is —NH-(pyrrolidin-3-yl).

Embodiment 178

A compound according to any one of embodiments 91 to 131, wherein
$R^7$ is piperidin-4-yl.

Embodiment 179

A compound according to any one of embodiments 91 to 131, wherein
$R^7$ is 3-OH-piperidin-1-yl, 4-OH-piperidin-1-yl, or 3-OH-pyrrolidin-1-yl.

Embodiment 180

A compound according to any one of embodiments 91 to 131, wherein
$R^7$ is 3-methoxy-pyrrolidin-1-yl or 4-methoxy-piperidin-1-yl.

Embodiment 181

A compound according to any one of embodiments 91 to 131, wherein
$R^7$ is —NH—(CH$_2$)$_2$—CO$_2$H.

Embodiment 182

A compound according to any one of embodiments 91 to 131, wherein
$R^7$ is 4-OH-cyclohexyloxy, 3-OH-cyclohexyloxy, or 3-OH-cyclopentyloxy.

Embodiment 183

A compound according to any one of embodiments 91 to 131, wherein
$R^7$ is piperidin-3-yloxy, tetrahydropyran-4-yloxy, or 1-methyl-piperidin-4-yloxy.

Embodiment 184

A compound according to any one of embodiments 91 to 131, wherein
$R^7$ is methoxy.

Embodiment 185

A compound according to any one of embodiments 91 to 131, wherein
$R^7$ is 2-methoxyethoxy.

Embodiment 186

A compound according to any one of embodiments 91 to 131, wherein
$R^7$ is 2-ethoxyethoxy.

Embodiment 187

A compound according to any one of embodiments 91 to 131, wherein
$R^7$ is 2-isopropoxyethoxy.

Embodiment 188

A compound according to any one of embodiments 91 to 131, wherein
$R^7$ is 3-ethoxy-n-propoxy.

Embodiment 189

A compound according to any one of embodiments 91 to 131, wherein
$R^7$ is —O—(CH$_2$)$_2$—O—(CH$_2$)$_2$—O—CH$_2$CH$_3$.

Embodiment 190

A compound according to any one of embodiments 91 to 131, wherein
$R^7$ is —O—(CH$_2$)$_2$—O—(CH$_2$)$_2$—N(CH$_3$)$_2$.

Embodiment 191

A compound according to any one of embodiments 91 to 131, wherein
$R^7$ is —O—CH$_2$—CO$_2$H.

Embodiment 192

A compound according to any one of embodiments 91 to 131, wherein
$R^7$ is —O—(CH$_2$)$_2$—NH$_2$.

Embodiment 193

A compound according to any one of embodiments 91 to 131, wherein
$R^7$ is —O—(CH$_2$)$_2$—NHCH$_3$ or —O—(CH$_2$)$_2$—N(CH$_3$)$_2$.

Embodiment 194

A compound according to any one of embodiments 91 to 131, wherein
$R^7$ is —O—(CH$_2$)$_3$—N(CH$_3$)$_2$ or —O—(CH$_2$)$_3$—N(CH$_2$CH$_3$)$_2$.

Embodiment 195

A compound according to any one of embodiments 91 to 131, wherein
$R^7$ is —O—(CH$_2$)$_2$—NH—C(CH$_3$)$_3$, —O—(CH$_2$)$_2$—NH—CH(CH$_3$)$_2$, or —O—(CH$_2$)$_2$—N(CH(CH$_3$)$_2$)$_2$.

Embodiment 196

A compound according to any one of embodiments 91 to 131, wherein
$R^7$ is 2-(NH$_2$)-n-propyloxy.

Embodiment 197

A compound according to any one of embodiments 91 to 131, wherein
$R^7$ is —O—(CH$_2$)$_2$—N(CH$_3$)—(CH$_2$)$_2$—N(CH$_3$)$_2$.

Embodiment 198

A compound according to any one of embodiments 91 to 131, wherein
$R^7$ is —O—(CH$_2$)$_2$—NH-(cyclohexyl).

Embodiment 199

A compound according to any one of embodiments 91 to 131, wherein
R$^7$ is —O—(CH$_2$)$_2$—O—(CH$_2$)$_2$—N(CH$_3$)$_2$.

Embodiment 200

A compound according to any one of embodiments 91 to 131, wherein
R$^7$ is 1-methyl-pyrrolidin-2-yl-methoxy.

Embodiment 201

A compound according to any one of embodiments 91 to 131, wherein
R$^7$ is 1-methyl-pyrrolidin-3-yloxy or 1-methyl-piperidin-4-yloxy.

Embodiment 202

A compound according to any one of embodiments 91 to 131, wherein
R$^7$ is —O—(CH$_2$)$_2$-(pyrrolidin-1-yl), —O—(CH$_2$)$_2$-(2-oxo-pyrrolidin-1-yl), —O—(CH$_2$)$_2$-(2-oxo-imidazolidin-1-yl), —O—(CH$_2$)$_2$-(morpholin-4-yl), —O—(CH$_2$)$_2$-(azepan-1-yl), —O—(CH$_2$)$_2$-(4-methyl-piperazin-1-yl), or —O—(CH$_2$)$_2$-(piperidin-1-yl).

Embodiment 203

A compound according to any one of embodiments 91 to 131, wherein
R$^7$ is —O—(CH$_2$)$_2$-(1,2,4-triazol-1-yl).

Embodiment 204

A compound according to any one of embodiments 91 to 131, wherein
R$^7$ is —O—(CH$_2$)$_2$—N(CH$_3$)-(2-pyridyl).

Embodiment 205

A compound according to any one of embodiments 91 to 131, wherein
R$^7$ is

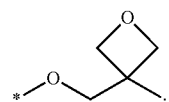

Embodiment 206

A compound according to any one of embodiments 91 to 131, wherein
R$^7$ is tetrahydrofuran-2-ylmethoxy or tetrahydrofuran-3-ylmethoxy.

Embodiment 207

A compound according to any one of embodiments 91 to 131, wherein
R$^7$ is 2-hydroxy-1-methyl-n-propoxy.

Embodiment 208

A compound according to any one of embodiments 91 to 131, wherein
R$^7$ is 1-hydroxyprop-2-yloxy.

Embodiment 209

A compound according to any one of embodiments 91 to 131, wherein
R$^7$ is

Embodiment 210

A compound according to any one of embodiments 91 to 131, wherein
R$^7$ is 2-hydroxy-n-butoxy.

Embodiment 211

A compound according to any one of embodiments 91 to 131, wherein
R$^7$ is 3-hydroxy-n-butoxy.

Embodiment 212

A compound according to any one of embodiments 91 to 131, wherein
R$^7$ is 2-hydroxy-3-methyl-n-butoxy.

Embodiment 213

A compound according to any one of embodiments 91 to 131, wherein
R$^7$ is 3-hydroxy-2,2-dimethyl-n-propoxy.

Embodiment 214

A compound according to any one of embodiments 91 to 131, wherein
R$^7$ is 3-(dimethylamino)-2-hydroxy-n-propoxy.

Embodiment 215

A compound according to any one of embodiments 91 to 131, wherein
R$^7$ is 2-fluoro-n-propoxy.

Embodiment 216

A compound according to any one of embodiments 91 to 131, wherein
R$^7$ is 2-hydroxy-2-methyl-n-propoxy.

Embodiment 217

A compound according to any one of embodiments 91 to 131, wherein
R$^7$ is 3-hydroxy-n-propoxy.

Embodiment 218

A compound according to any one of embodiments 91 to 131, wherein
R$^7$ is 2-hydroxy-n-propoxy.

Embodiment 219

A compound according to any one of embodiments 91 to 131, wherein
$R^7$ is 2-hydroxy-n-pentyloxy.

Embodiment 220

A compound according to any one of embodiments 91 to 131, wherein
$R^7$ is 2-hydroxy-n-hexyloxy.

Embodiment 221

A compound according to any one of embodiments 91 to 131, wherein
$R^7$ is 3-hydroxy-3-methyl-n-butoxy.

Embodiment 222

A compound according to any one of embodiments 91 to 131, wherein
$R^7$ is 1-(hydroxymethyl)-2-hydroxyethoxy.

Embodiment 223

A compound according to any one of embodiments 91 to 131, wherein
$R^7$ is 1-(hydroxymethyl)-2-methoxyethoxy.

Embodiment 224

A compound according to any one of embodiments 91 to 131, wherein
$R^7$ is 3-hydroxy-1-methyl-n-butoxy.

Embodiment 225

A compound according to any one of embodiments 91 to 131, wherein
$R^7$ is 2,2-difluoro-3-hydroxy-n-propoxy.

Embodiment 226

A compound according to any one of embodiments 91 to 131, wherein
$R^7$ is 3,4-dihydroxy-n-butoxy.

Embodiment 227

A compound according to any one of embodiments 91 to 131, wherein
$R^7$ is 4-hydroxy-n-butoxy.

Embodiment 228

A compound according to any one of embodiments 91 to 131, wherein
$R^7$ is

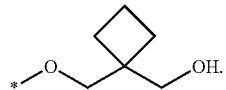

Embodiment 229

A compound according to any one of embodiments 91 to 131, wherein
$R^7$ is

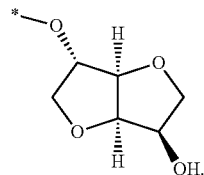 [SMILES: *O[C@H]1CO[C@H]2[C@@H]1OC[C@H]2O]

Embodiment 230

A compound according to any one of embodiments 91 to 131, wherein
$R^7$ is

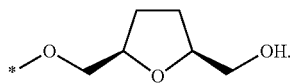 [SMILES: *OC[C@H]1CC[C@@H](CO)O1]

Embodiment 231

A compound according to any one of embodiments 91 to 131, wherein
$R^7$ is 2,3-dimethoxy-n-propoxy.

Embodiment 232

A compound according to any one of embodiments 91 to 131, wherein
$R^7$ is —S—(CH$_2$)$_2$—OH.

Embodiment 233

A compound according to any one of embodiments 91 to 131, wherein
$R^7$ is 2-fluoro-3-hydroxy-n-propoxy.

Embodiment 234

A compound according to any one of embodiments 91 to 131, wherein
$R^7$ is 3-fluoro-n-propoxy.

Embodiment 235

A compound according to any one of embodiments 91 to 131, wherein
$R^7$ is 4-hydroxy-n-pentyloxy.

Embodiment 236

A compound according to any one of embodiments 91 to 131, wherein
$R^7$ is —O—CH$_2$—CN.

Embodiment 237

A compound according to any one of embodiments 91 to 131, wherein
$R^7$ is —O—CH$_2$—C(O)—N(CH$_3$)$_2$.

Embodiment 238

A compound according to any one of embodiments 91 to 131, wherein
R⁷ is 3-fluoro-n-propoxy.

Embodiment 239

A compound according to any one of embodiments 91 to 131, wherein
R⁷ is 2-hydroxyethoxy.

Embodiment 240

A compound according to any one of embodiments 91 to 131, wherein
R⁷ is 2-hydroxy-n-propoxy.

Embodiment 241

A compound according to any one of embodiments 91 to 131, wherein
R⁷ is —O—C$_{1-6}$ alkylene-O—R$^c$, where R$^c$ is —H.

Embodiment 242

A compound according to any one of embodiments 91 to 131, wherein
R⁷ is —O—C$_{1-6}$ alkylene-O—R$^c$, where R$^c$ is —C$_{1-6}$ alkyl optionally substituted one or more times with substituents selected independently from the group consisting of halogen and —OH, and the alkylene is optionally substituted one or more times with halogen.

Embodiment 243

A compound according to any one of embodiments 91 to 131, wherein
R⁷ is —O—C$_{1-6}$ alkylene-O—R$^c$, where R$^c$ is —H, and the alkylene is optionally substituted one or more times with halogen.

Embodiment 244

A compound according to any one of embodiments 91 to 243, wherein
the compound is in its free (non-salted) form.

Embodiment 245

A compound according to any one of embodiments 91 to 243, wherein
the compound is in the form of a pharmaceutically acceptable salt.

Embodiment 246

A compound according to embodiment 245, wherein
the compound is in the form of a hydrochloride salt.

Embodiment 247

A compound according to any one of embodiments 91 to 246, wherein R⁵ is hydrogen and the benzimidazole exists in the following tautomeric form:

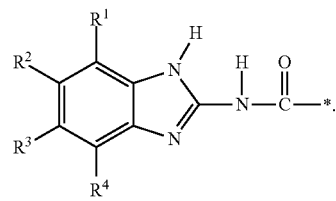

Embodiment 248

A compound according to any one of embodiments 91 to 246, wherein R⁵ is hydrogen and the benzimidazole exists in the following tautomeric form:

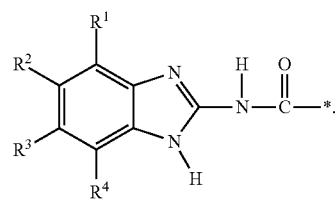

Embodiment 249

A compound according to any one of embodiments 91 to 246, wherein R⁵ is hydrogen and the benzimidazole exists in the following tautomeric form:

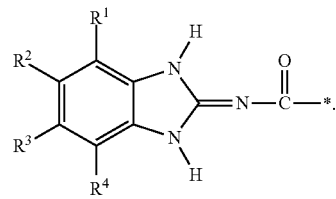

General Experimental Section

The routes below illustrate general methods of synthesizing compounds of Formula (I), pharmaceutically acceptable salts thereof, or tautomers of any of the foregoing. The skilled artisan will appreciate that the compounds of the invention could be made by methods other than those specifically described herein, by adaptation of the methods described herein and/or by adaptation of methods known in the art. In general, compounds of the invention may be prepared in a multi-step synthesis, as shown below. All quantities shown are approximate, and are given solely for illustrative purposes.

The following abbreviations may be used in describing reaction conditions, common reagents, common solvents, or methods of analysis. This list is not intended to be exhaustive. In instances where the experimental methods employ an acronym or abbreviation that is not defined below, the acronym or abbreviation has the meaning that it would have to the skilled artisan in the relevant art.

DCM=dichloromethane
DIEA=diisopropylethylamine
DMF=N,N'-dimethylformamide
DMSO=dimethylsulfoxide HBTU=2-(1H-benzotriazol-1-yl)-1,1,3,3-tetramethyluronium hexafluorophosphate
HCl=hydrochloric acid
DME=dimethylethane
LAH=lithium aluminum hydride
LCMS=LC-MS=LC/MS=liquid chromatography-mass spectrometry analysis
THF=tetrahydrofuran
TLC=thin layer chromatography
rt or RT or r.t.=room temperature
h=hour
min=minutes
M=molar concentration
N=normal concentration

Step 1-A: Synthesis of a Substituted 2-aminobenzimidazole

To a mixture of 4-bromo-2-nitroaniline (1 mmol), a boronic acid (1.5 mmol), and Na₂CO₃ (3 mmol), toluene (10 mL) and water (5 mL) would be added. (In some instances, toluene may be replaced by DME.) The resulting mixture would be purged with nitrogen for 10 minutes. Then, tetrakis(triphenylphosphine)palladium (0.05 mmol) would be added, and the reaction mixture would be heated at reflux under nitrogen until the reaction is substantially complete (e.g., 2-10 hours). The reaction mixture would then be cooled to room temperature and filtered through Celite, and then would be washed with ethyl acetate. The organic layer would be separated and dried over sodium sulfate, and then concentrated and purified by column chromatography using a silica gel stationary phase and ethyl acetate in hexanes as an eluent. The purified solution would contain a 4-substituted-2-nitroaniline compound.

The 4-substituted-2-nitroaniline compound (1 mmol) would be taken up into solution using an ethyl acetate-methanol mixture (about 1:1). To this solution, Pd—C would be added, and the resulting mixture would be stirred under a hydrogen atmosphere for about 30 minutes to 1 hour. (In some instances, SnCl₂ may be used instead of Pd—C and H₂.) Then, the solution would be filtered on Celite, washed with methanol, and then concentrated until the characteristic dark-brown color of a diamine is apparent. The diamine compound would be taken up into methanol, and CNBr (1 mmol) would be added. The resulting mixture would be stirred at room temperature for about 30 minutes. The solution would then be concentrated to dryness, and residual methanol would be removed by washing the solution three times with ether, followed by drying to obtain a substituted 2-aminobenzimidazole derivative as a hydrobromide salt. The reaction scheme below provides an illustration that accompanies this textual description.

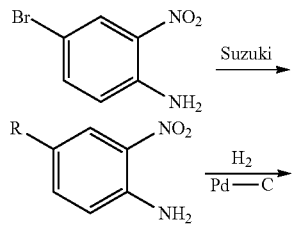

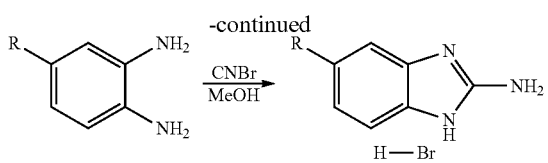

Step 1-B: Alternate Synthesis of a Substituted 2-aminobenzimidazole

To a mixture of 4-bromo-benzene-1,2-diamine (1 mmol), a boronic acid (1.5 mmol), and Na₂CO₃ (3 mmol), toluene (10 mL) and water (5 mL) would be added. (In some instances, toluene may be replaced by DME.) The resulting mixture would be purged with nitrogen for 10 minutes. Then, tetrakis(triphenylphosphine)palladium (0.05 mmol) would be added, and the mixture would be heated at reflux for 4 hours under nitrogen. The reaction mixture would then be cooled to room temperature and filtered through Celite, and then would be washed with ethyl acetate. The organic layer would be separated and dried over sodium sulfate, and then concentrated and purified by column chromatography using a silica gel stationary phase and ethyl acetate in hexanes as an eluent. The purified solution would contain a 4-substituted-1,2-diaminophenyl compound. The diamine compound would be taken up into methanol, and CNBr (1 mmol) would be added. The resulting mixture would be stirred at room temperature for about 30 minutes. The solution would then be concentrated to dryness, and residual methanol would be removed by washing the solution with ether three times, followed by drying to obtain a substituted 2-aminobenzimidazole derivative as hydrobromide salt. The reaction scheme below provides an illustration that accompanies this textual description.

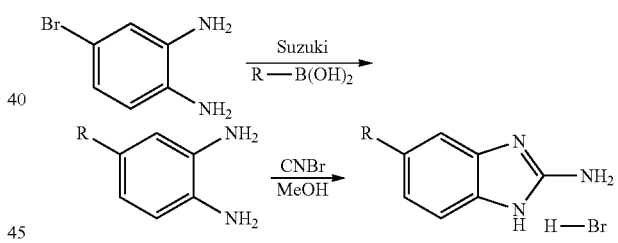

Step 1-C: Alternate Synthesis of a Substituted 2-aminobenzimidazole

A mixture of 5-fluoro-2-nitro-phenylamine (1 mmol), an alcohol (2 mmol), and potassium tert-butoxide (3 mmol) in THF (20 mL) would be heated at about 60° C. overnight. After cooling the mixture to room temperature, water would be added and then the mixture would be extracted with ethyl acetate. The organic layer would be washed with brine and dried over Na₂SO₄ and then concentrated. The crude material would be purified on a silica gel column to yield a 5-alkyloxy-2-nitro-phenylamine. The 5-alkyloxy-2-nitro-phenylamine (1.0 mmol) would be dissolved in an ethyl acetate-methanol mixture (about 1:1, 10 mL) in a round-bottom flask. To this solution Pd—C would be added, and the mixture would be stirred under a hydrogen atmosphere, while monitoring the reaction with thin-layer chromatography (TLC). After TLC shows substantial completion of the reaction, the solution would be filtered on celite and then washed with methanol and concentrated to obtain a 4-alkyloxy-benzene-1,2-diamine. The 4-alkyloxy-benzene-1,2-diamine (1 mmol) would be dissolved in ethanol and CNBr (1.5 mmol) would be added. The resulting dark brown solution would be heated at 60° C. for 30 minutes. Thereafter, the mixture would be cooled to room temperature, and the solvent would be evaporated. Then the mixture would be washed with ether two or three times to obtain a 5-alkyloxy-1H-benzoimidazol-2-ylamine as a hydrobromide salt. The reaction scheme below provides an illustration that accompanies this textual description.

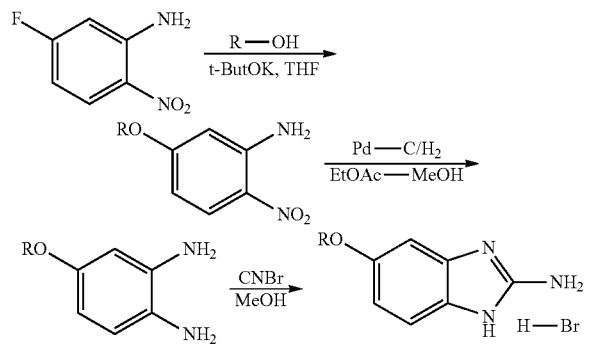

Step 2: Synthesis of a Substituted 2-aminobenzimidazole amide

A mixture of a carboxylic acid (1 mmol), HBTU (1 mmol) and DIEA (3 mmol) in DMF (3 mL) would be heated at 80° C. for 10 minutes. To this reaction mixture a substituted 2-aminobenzimidazole hydrobromide salt (1 mmol) would be added, and the mixture would continue to be heated at 80° C. for 30 minutes. After cooling the reaction mixture to room temperature, an aqueous sodium bicarbonate solution would be added, and the mixture would be stirred for 30 minutes. The mixture would then be filtered, washed with water, and purified on silica gel column to yield a substituted 2-aminobenzimidazole amide. The reaction scheme below provide an illustration that accompanies this textual description.

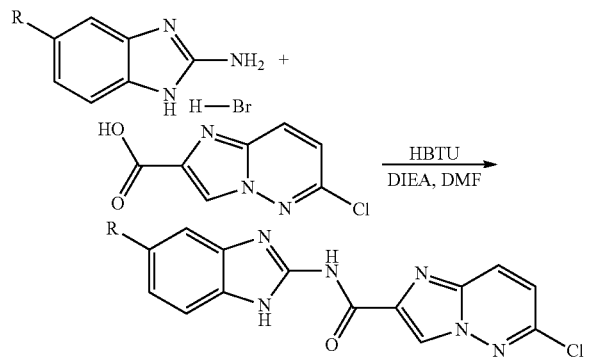

Step 3: Synthesis of a 6-alkoxyimidazo[1,2-b]pyridazine-2-carboxylic acid amide

To a solution of an alcohol (0.48 mmol) in dry DMF (1 mL) NaH (0.80 mmol, 60% dispersion in mineral oil) would be added, and the mixture would be stirred at room temperature for 20 minutes under nitrogen. To this mixture a 6-chloroimidazo[1,2-b]pyridazine derivative (0.16 mmol) would be added to the reaction mixture. The reaction would be monitored by LCMS until substantially complete. Then, 10 mL of water would be added and the reaction mixture would be stirred for 10 minutes. The reaction was then filtered through a fine fritted funnel and the crude product would be washed with water. After air drying, the product would be purified by column chromatography (prepacked silica column) using 9:1 DCM and 2N ammonia in methanol.

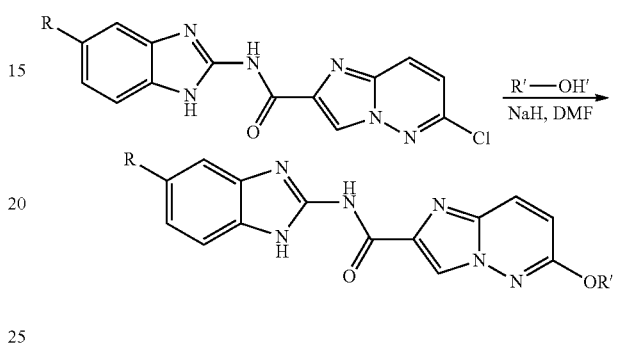

Step 4: Synthesis of a 6-amino-substituted imidazo[1,2-b]pyridazine-carboxylic acid amide To a solution of a 6-chloroimidazo[1,2-b]pyridazine derivative (0.16 mmol) in dry N-methylpyrrolidone (1 mL), an amine (0.80 mmol) would be added, and the mixture would be stirred at 80° C. The reaction would be monitored by LCMS until substantially complete. After cooling the reaction mixture, 10 mL of water would be added and the reaction mixture would be stirred for 10 minutes. The reaction mixture would then be filtered and the crude product would be washed with water. After air drying, the product would be purified by column chromatography (pre-packed silica column) using 9:1 DCM and 2N ammonia in methanol.

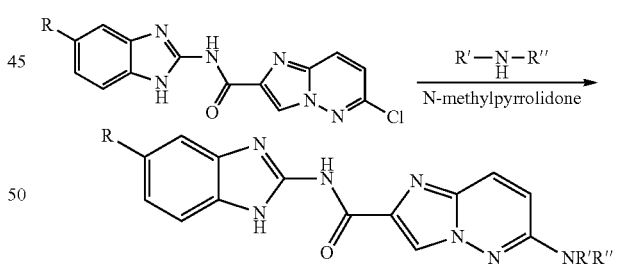

Synthesis of Specific Example Compounds

The syntheses of certain example compounds are descried below. These specific syntheses are intended to supplement the general synthetic pathway described above. Specific syntheses are not recited for every example compound. For the example compounds for which specific syntheses are not described, the compounds may be synthesized by methods analogous to the general methods described above and/or by methods analogous to those described below for the synthesis of specific example compounds.

Example 8

6-(2-Methoxy-ethoxy)-imidazo[1,2-b]pyridazine-2-carboxylic acid [5-(3-trifluoromethyl-phenyl)-1H-benzoimidazol-2-yl]-amide A mixture of 6-chloro-imidazo[1,2-b]pyridazine-2-carboxylic acid (2.5 g), HBTU (4.41 g) and DIEA (4.0 mL) in DMF (20 mL) were stirred at room temperature for 10 minutes. To this reaction mixture was added 5-(3-trifluoromethyl-phenyl)-1H-benzoimidazol-2-ylamine hydrobromide salt (3.61 g), and the mixture was heated at 80° C. for 30 minutes. After cooling the reaction mixture to room temperature, an aqueous sodium bicarbonate solution (200 mL) was added, and the mixture was stirred for 30 minutes. The mixture was then filtered, washed with water, dried, and purified on an 80 g pre-packaged silica gel column with a gradient of 0 to 10% 2M ammonia-methanol in DCM. 4.4 g of 6-chloro-imidazo[1,2-b]pyridazine-2-carboxylic acid [5-(3-trifluoromethyl-phenyl)-1H-benzoimidazol-2-yl]-amide was obtained. LCMS (m/z): 457.8. $^1$H NMR (400 MHz, DMSO-$d_6$) δ 11.85-12.45 (2H, m) 9.08 (1H, s) 8.36 (1H, d) 7.93-8.04 (2H, m) 7.83 (1H, s) 7.67-7.75 (2H, m) 7.49-7.64 (3H, m).

To a solution of 2-methoxy-ethanol (0.013 mL) in dry DMF (0.25 mL), sodium hydride (8 mg, 60% dispersion in mineral oil) was added, and the mixture was stirred at room temperature for 20 minutes under nitrogen. 6-chloro-imidazo[1,2-b]pyridazine-2-carboxylic acid [5-(3-trifluoromethyl-phenyl)-1H-benzoimidazol-2-yl]-amide (30 mg) was added to the reaction mixture, and the mixture was warmed to 70° C. The reaction was monitored by LCMS for 1 hour until substantially complete. After cooling the reaction mixture, 10 mL of water was added and the reaction mixture was stirred for 10 minutes. The reaction was then filtered through a fine fritted funnel and the crude product was washed with water. After air drying, the product was purified by column chromatography (pre-packed silica column) using a gradient of 0 to 6% 2M ammonia-methanol in DCM. 20 mg of 6-(2-methoxy-ethoxy)-imidazo[1,2-b]pyridazine-2-carboxylic acid [5-(3-trifluoromethyl-phenyl)-1H-benzoimidazol-2-yl]-amide was obtained. LCMS (m/z): 497.8. $^1$H NMR (400 MHz, DMSO-$d_6$) δ 8.83 (1H, s) 8.14 (1H, d) 7.93-8.03 (2H, m) 7.83 (1H, s) 7.67-7.74 (2H, m) 7.57-7.63 (1H, m) 7.51 (1H, dd) 7.10 (1H, d) 4.42-4.49 (2H, m) 3.70-3.76 (2H, m) 3.32-3.34 (3H, m).

Example 27

6-(2-Morpholin-4-yl-ethoxy)-imidazol[1,2-b]pyridazine-2-carboxylic acid [5-(3-trifluoromethyl-phenyl)-1H-benzoimidazol-2-yl]-amide To a stirred mixture of 6-chloro-imidazo[1,2-b]pyridazine-2-carboxylic acid [5-(3-trifluoromethyl-phenyl)-1H-benzoimidazol-2-yl]-amide (100 mg) and 2-morpholin-4-yl-ethanol (250 µL) in dry DMF (1 mL) was added NaH (100 mg, 60% dispersion in mineral oil) and the mixture was stirred at room temperature for 1 h. To this was added water (20 mL) and the reaction mixture stirred for 10 minutes. The precipitated solid was filtered and purified by column chromatography (12 g pre-packed silica gel column cartridge) using DCM and 2N ammonia in methanol to afford 6-(2-morpholin-4-yl-ethoxy)-imidazo[1,2-b]pyridazine-2-carboxylic acid [5-(3-trifluoromethyl-phenyl)-1H-benzoimidazol-2-yl]-amide (42 mg). LCMS (m/z): 552.8.

Example 120

6-((1R,3R)-3-hydroxy-1-methyl-butoxy)-imidazo[1,2-b]pyridazine-2-carboxylic acid [5-(3-trifluoromethyl-phenyl)-1H-benzoimidazol-2-yl]-amide To a solution of (2R,4R)-(−)-pentanediol (31.2 mg) in dry DMF (1 mL) NaH (12 mg, 60% dispersion in mineral oil) was added, and the mixture was stirred at room temperature for 20 minutes under nitrogen. To this mixture 6-chloro-imidazo[1,2-b]pyridazine-2-carboxylic acid [5-(3-trifluoromethyl-phenyl)-1H-benzoimidazol-2-yl]-amide (45.6 mg) was added. The reaction was monitored by LCMS until substantially complete. Then, 10 mL of water was added and the reaction mixture was stirred for 10 minutes. The reaction was then filtered through a fine fritted funnel and the crude product was washed with water. After air drying, purified by column chromatography to obtain 6-((1R,3R)-3-hydroxy-1-methyl-butoxy)-imidazo[1,2-b]pyridazine-2-carboxylic acid [5-(3-trifluoromethyl-phenyl)-1H-benzoimidazol-2-yl]-amide (25.2 mg). LCMS (m/z): 526.1. $^1$H NMR (400 MHz, CDCl$_3$) δ 8.39 (1H, s) 7.89 (1H, s) 7.45-7.85 (7H, m) 6.79 (1H, d) 5.42 (1H, ddd) 3.95 (1H, d) 2.18 (1H, brs) 1.91 (1H, ddd) 1.69-1.79 (1H, m) 1.44 (3H, d) 1.26 (3H, d)

Example 122

6-((R)-2-hydroxy-propoxy)-imidazol[1,2-b]pyridazine-2-carboxylic acid [5-(3-chloro-4-trifluoromethyl-phenyl)-1H-benzoimidazol-2-yl]-amide To a stirred solution of (R)-2-hydroxy-propionic acid methyl ester (10 g) and 3,4-dihydro-2H-pyran (15 mL) in DCM (400 mL) was added camphorsulfonic acid (50 mg) (exothermic reaction). The reaction mixture was stirred at ambient temperature for 2 hours, and washed with saturated bicarbonate solution (20 mL). The organic layer was dried, filtered and concentrated to obtain crude (R)-2-(tetrahydro-pyran-2-yloxy)-propionic acid methyl ester, which was used as is in the next step. To a stirred suspension of LAH (4 g) in anhydrous ether (400 mL) at 0-5° C. was added (R)-2-(tetrahydro-pyran-2-yloxy)-propionic acid methyl ester dropwise over 30 minute period. After completion of the addition, the cold bath was removed and the reaction mixture was stirred at room temperature for 2 hours. The resulting mixture was cooled to 0-5° C., and ethyl acetate was added dropwise to quench excess LAH, which was followed by the addition of saturated sodium sulfate solution and solid sodium sulfate. The resulting mixture was stirred at room temperature for 1 hour, the solid was filtered off, and the solid was washed with ether. The combined organic layer was dried over Na$_2$SO$_4$, filtered, concentrated and the residue was purified by column chromatography using a silica gel stationary phase (pre-treated with 0.1 triethylamine in hexanes) and hexanes in ethyl acetate to get (R)-2-(tetrahydro-pyran-2-yloxy)-propan-1-ol. $^1$H NMR (400 MHz, CDCl$_3$): δ 4.51-4.75 (1H, m) 3.76-4.02 (2H, m) 3.42-3.62 (3H, m) 1.67-1.90 (2H, m) 1.46-1.63 (4 h, m) 1.10-1.24 (3H, m).

A mixture of 4-bromo-2-nitroaniline (2.17 g), 3-chloro-4-trifluoromethyl-phenylboronic acid (3.5 g), and Na$_2$CO$_3$ (3.5 g), tetrakis(triphenylphosphine)palladium(0) (0.5 g), in DME (60 mL) and water (60 mL) was degassed under vacuum and the vacuum was broken with N$_2$ gas. The resultant reaction mixture was kept stirring at 90-100° C. for 4 h. The reaction mixture was cooled to room temperature, separated the organic layer and the aqueous layer was extracted with ethyl acetate (100 mL). The combined organic layer was dried over sodium sulfate, filtered off sodium sulfate, the filtrate was concentrated and the residue was purified by column chromatography using a silica gel stationary phase and ethyl acetate in hexanes (2:8) as an eluent to afford 3'-chloro-3-nitro-4'-trifluoromethyl-biphenyl-4-ylamine (3.2 g).

To a stirred solution of 3'-chloro-3-nitro-4'-trifluoromethyl-biphenyl-4-ylamine (3.2 g) in ethanol (100 mL) was added $SnCl_2$ (12 g) and the resultant reaction mixture was kept stirring at 100° C. for 16 hours. The volatiles were removed under reduced pressure and the residue was taken in ethyl acetate (500 mL). To this was added saturated bicarbonate solution (300 mL) and stirred for 30 min at room temperature. This was filtered through a pad of celite and the celite pad was washed with ethyl acetate (100 mL). The combined organic layer was dried, filtered and concentrated and the residue was used as is in the next step. This was dissolved in methanol (100 mL) and CNBr was added (4 g). The resulting mixture was stirred at room temperature for about 1 hour. The solution was then concentrated to dryness, and residual methanol was removed by co-evaporating with toluene about 3 times, followed by washing hydrobromide salt with anhydrous ether (100 mL) to get 5-(3-chloro-4-trifluoromethyl-phenyl)-1H-benzoimidazol-2-ylamine hydrobromide salt (2.8 g). LCMS (m/z): 312.8

A mixture of 6-chloro-imidazo[1,2-b]pyridazine-2-carboxylic acid (600 mg), HBTU (900 mg), DIEA (1 mL) and 5-(3-chloro-4-trifluoromethyl-phenyl)-1H-benzoimidazol-2-ylamine hydrobromide salt (794 mg) in DMF (5 mL) was heated at 80° C. for 1 hour with stirring. After cooling the reaction mixture to room temperature, an aqueous sodium bicarbonate solution was added, and the mixture was stirred for 30 minutes at room temperature. The solid was filtered, washed with water, and dried under vacuum to get 6-chloro-imidazo[1,2-b]pyridazine-2-carboxylic acid [5-(3-chloro-4-trifluoromethyl-phenyl)-1H-benzoimidazol-2-yl]-amide (890 mg). LCMS (m/z): 491.8.

To a stirred mixture of 6-chloro-imidazo[1,2-b]pyridazine-2-carboxylic acid [5-(3-chloro-4-trifluoromethyl-phenyl)-1H-benzoimidazol-2-yl]-amide (80 mg) and (R)-2-(tetrahydro-pyran-2-yloxy)-propan-1-ol (100 μL) in dry DMF (1 mL) was added NaH (40 mg, dispersion in mineral oil) and the mixture was stirred at room temperature for 1 h. Then, water (10 mL) was added and the reaction mixture stirred for 10 minutes. The precipitated solid was filtered and dissolved in 1:1 mixture of methanol and DCM (5 mL). To this was added 2 M solution of hydrochloric acid in methanol (1 mL) and stirred at room temperature for 2 h. After air drying, the product was purified by column chromatography (12 g pre-packed silica gel column cartridge) using DCM and 2N ammonia in methanol to afford 6-((R)-2-hydroxy-propoxy)-imidazo[1,2-b]pyridazine-2-carboxylic acid [5-(3-chloro-4-trifluoromethyl-phenyl)-1H-benzoimidazol-2-yl]-amide (37 mg). LCMS (m/z): 532. $^1$H NMR (400 MHz, DMSO-$d_6$): δ 12.5 and 11.5 (1H, brs) 8.85 (1H, s) 8.15 (1H, d) 7.92 (1H, brs) 7.87-7.93 (3H, m) 7.55-7.63 (2H, m) 7.08 (1H, d) 5.01 (1H, d) 4.17 (2H, d) 4.03-4.07 (1H, m) 1.18 (3H, d).

Example 123

6-((S)-2-Hydroxy-propoxy)-imidazo[1,2-b]pyridazine-2-carboxylic acid [5-(3-chloro-4-trifluoromethyl-phenyl)-1H-benzoimidazol-2-yl]-amide (S)-2-(Tetrahydro-pyran-2-yloxy)-propan-1-ol was prepared from (S)-2-hydroxy-propionic acid methyl ester as described above in Example 122. $^1$H NMR (400 MHz, $CDCl_3$): δ 4.53-4.75 (1H, m) 3.78-4.03 (2H, m) 3.42-3.67 (3H, m) 2.13 (1H, t) 1.69-1.92 (2H, m) 1.48-1.66 (4H, m) 1.11-1.27 (3H, m).

6-((S)-2-Hydroxy-propoxy)-imidazo[1,2-b]pyridazine-2-carboxylic acid [5-(3-chloro-4-trifluoromethyl-phenyl)-1H-benzoimidazol-2-yl]-amide (38 mg) was prepared from 6-chloro-imidazo[1,2-b]pyridazine-2-carboxylic acid [5-(3-chloro-4-trifluoromethyl-phenyl)-1H-benzoimidazol-2-yl]-amide (80 mg) and (S)-2-(tetrahydro-pyran-2-yloxy)-propan-1-ol (100 μL) as described above in Example 122. LCMS (m/z): 532. $^1$H NMR (400 MHz, DMSO-$d_6$): δ 12.5 and 11.5 (1H, brs) 8.85 (1H, s) 8.14 (1H, d) 8.02 (1H, brs) 7.85-7.93 (3H, m) 7.55-7.63 (2H, m) 7.07 (1H, d) 5.01 (1H, d) 4.17 (2H, d) 4.02-4.07 (1H, m) 1.19 (3H, d).

Example 131

6-(2-Hydroxy-ethoxy)-imidazo[1,2-b]pyridazine-2-carboxylic acid [5-(3-chloro-4-fluoro-phenyl)-1H-benzoimidazol-2-yl]-amide 6-(2-Hydroxy-ethoxy)-imidazo[1,2-b]pyridazine-2-carboxylic acid [5-(3-chloro-4-fluoro-phenyl)-1H-benzoimidazol-2-yl]-amide was prepared similar to Example 122. LCMS (m/z): 467.8. $^1$H NMR (400 MHz, DMSO-$d_6$): δ 8.87 (1H, s) 8.16 (1H, d) 7.87 (1H, m) 7.81 (1H, s) 7.67-7.71 (1H, m) 7.62 (1H, d) 7.49-7.54 (2H, m) 7.09 (1H, d) 4.36 (2H, t) 3.79 (2H, t).

Example 142

6-(4-Hydroxy-piperidin-1-yl)-imidazo[1,2-b]pyridazine-2-carboxylic acid [5-(3-chloro-5-fluoro-phenyl)-1H-benzoimidazol-2-yl]-amide A mixture of 4-bromo-benzene-1,2-diamine (43 g), 3-chloro-5-fluorophenylboronic acid (50 g) $Na_2CO_3$ (107 g) in toluene (1.5 L) and water (0.6 L) degassed with nitrogen for 30 min then tetrakis(triphenylphosphine)palladium (10 g) was added and heated at 105° C. for 2 hours under nitrogen. The reaction mass was cooled to room temperature, filtered on celite bed and washed with ethyl acetate. Organic layer was separated, concentrated under reduced pressure and purified on silica gel column (eluent: 10% to 50% ethyl acetate in hexanes). The obtained dark brown diamine was dissolved in methanol (0.6 L) and CNBr (36.5 g) was added. After stirring overnight at room temperature, the solvent was evaporated. The resulting solid was washed with ether and dried to obtain 5-(3-chloro-5-fluorophenyl)-1H-benzoimidazol-2-ylamine hydrobromide salt (42 g). LCMS (m/z): 262.6.

A mixture of 6-chloro-imidazo[1,2-b]pyridazine-2-carboxylic acid (2.5 g), HBTU (4.41 g) and DIEA (4.0 mL) in DMF (20 mL) were stirred at room temperature for 10 minutes. To this reaction mixture was added 5-(3-chloro-5-fluoro-phenyl)-1H-benzoimidazol-2-ylamine hydrobromide salt (3.46 g), and the mixture was heated at 80° C. for 30 minutes. After cooling the reaction mixture to room temperature, an aqueous sodium bicarbonate solution (200 mL) was added, and the mixture was stirred for 30 minutes. The mixture was then filtered, washed with water, dried, and purified on a 80 g pre-packaged silica gel column with a gradient of 0 to 10% 2 M ammonia-methanol in DCM. 4.4 g of 6-chloro-imidazo[1,2-b]pyridazine-2-carboxylic acid [5-(3-chloro-5-fluoro-phenyl)-1H-benzoimidazol-2-yl]-amide was obtained. LCMS (m/z): 441.9. $^1$H NMR (400 MHz, DMSO-$d_6$) δ 12.18 (2H, br. s.) 9.08 (1H, s) 8.32-8.39 (1H, m) 7.82 (1H, s) 7.46-7.64 (6H, m).

To a solution of 6-chloro-imidazo[1,2-b]pyridazine-2-carboxylic acid [5-(3-chloro-5-fluoro-phenyl)-1H-benzoimidazol-2-yl]-amide (0.07 g) in N-methylpyrrolidone (1 mL), was added piperidin-4-ol (0.08 g) and the mixture was heated to 80° C. for 12 hours. After cooling the reaction mixture, 10 mL of water was added and the reaction mixture was stirred for 10 minutes. The reaction was then filtered through a fine fritted funnel and the crude product was washed with water. After air drying, purified by column chromatography (pre-packed silica column) using a gradient of 0 to 10% 2M ammonia-methanol in DCM to obtain 6-(4-hydroxy-piperidin-1-yl)-imidazo[1,2-b]pyridazine-2-carboxylic acid [5-(3-chloro-5-fluoro-phenyl)-1H-benzoimidazol-2-yl]-amide (32 mg). LCMS (m/z): 506.7. $^1$H NMR (400 MHz, DMSO-d$_6$) δ 8.64 (1H, s) 7.93 (1H, d) 7.80-7.86 (1H, m) 7.48-7.65 (4H, m) 7.35-7.43 (2H, m) 4.79 (1H, br. s.) 3.95 (2H, ddd) 3.70-3.80 (1H, m) 3.18-3.45 (2H, m) 1.79-1.90 (2H, m) 1.39-1.53 (2H, m).

Example 143

6-(2-Hydroxy-ethoxy)-imidazol[1,2-b]pyridazine-2-carboxylic acid [5-(3-trifluoromethoxy-phenyl)-1H-benzoimidazol-2-yl]-amide A mixture of 4-bromo-2-nitroaniline (19.1 g), 3-(trifluoromethoxy)phenylboronic acid (25.0 g), and Na$_2$CO$_3$ (16.2 g), in toluene (190 mL) and water (90 mL) was purged with nitrogen for 10 minutes. Tetrakis(triphenylphosphine)palladium (2.54 g) was added, and the reaction mixture was heated at reflux for 2 hours under nitrogen. The reaction mixture was cooled to room temperature and filtered through celite, which was washed with toluene. The organic layer would be separated and dried over sodium sulfate, and then concentrated and purified by column chromatography using a 220 g silica gel cartridge and an ethyl acetate in hexanes gradient. This yielded 28.5 g of the 3-nitro-3'-trifluoromethoxy-biphenyl-4-ylamine.

3-Nitro-3'-trifluoromethoxy-biphenyl-4-ylamine (28.5 g) was dissolved in methanol (250 mL). To this solution, Pd—C (10%, Degussa Type, 15 g) was added, and the resulting mixture was stirred under a hydrogen atmosphere for 4 hours. The solution was filtered on celite, washed with methanol, and then concentrated to give 3'-trifluoromethoxy-biphenyl-3,4-diamine (17.8 g) which was used without further purification. 3'-Trifluoromethoxy-biphenyl-3,4-diamine (17.8 g) was taken up into methanol (100 mL), and cyanogen bromide (8.9 g) was added. The resulting mixture was stirred at room temperature for about 30 minutes. The solution was concentrated to dryness. The resulting crude product was triturated with diethyl ether (100 mL), filtered and dried to obtain 5-(3-trifluoromethoxy-phenyl)-1H-benzoimidazol-2-ylamine hydrobromide salt (21.3 g), which was used without further purification. LCMS (m/z): 293.9.

A mixture of 6-chloro-imidazo[1,2-b]pyridazine-2-carboxylic acid (2.5 g), HBTU (4.41 g) and DIEA (4.0 mL) in DMF (20 mL) were stirred at room temperature for 10 minutes. To this reaction mixture was added 5-(3-trifluoromethoxy-phenyl)-1H-benzoimidazol-2-ylamine hydrobromide salt (3.78 g), and the mixture was heated at 80° C. for 30 minutes. After cooling the reaction mixture to room temperature, an aqueous sodium bicarbonate solution (200 mL) was added, and the mixture was stirred for 30 minutes. The mixture was then filtered, washed with water, dried, and purified on an 80 g pre-packaged silica gel column with a gradient of 0 to 10% 2M ammonia-methanol in DCM. 4.7 g of 6-chloro-imidazo[1,2-b]pyridazine-2-carboxylic acid [5-(3-trifluoromethoxy-phenyl)-1H-benzoimidazol-2-yl]-amide was obtained. LCMS (m/z): 473.9. $^1$H NMR (400 MHz, DMSO-d$_6$) δ 12.14 (2H, br. s.) 9.08 (1H, s) 8.35 (1H, d) 7.81 (1H, s) 7.73 (1H, d) 7.47-7.65 (5H, m) 7.34 (1H, d).

6-(2-Hydroxy-ethoxy)-imidazo[1,2-b]pyridazine-2-carboxylic acid [5-(3-trifluoro-methoxy-phenyl)-1H-benzoimidazol-2-yl]-amide (41 mg) was prepared from 6-chloro-imidazo[1,2-b]pyridazine-2-carboxylic acid [5-(3-trifluoromethoxy-phenyl)-1H-benzoimidazol-2-yl]-amide (80 mg) and 2-(tetrahydro-pyran-2-yloxy)-ethanol as described in Example 122. LCMS (m/z): 499.8. $^1$H NMR (400 MHz, DMSO-d$_6$): δ 8.9 (1H, s) 8.2 (1H, d) 7.99 (1H, s) 7.72-7.81 (3H, m) 7.63-7.69 (2H, m) 7.41 (1H, d) 7.16 (1H, d) 4.37 (3H, t) 3.80 (3H, t).

Example 144

6-(2-hydroxy-ethoxy)-imidazo[1,2-b]pyridazine-2-carboxylic acid [5-(3-chloro-phenyl)-1H-benzoimidazol-2-yl]-amide A mixture of 4-bromo-benzene-1,2-diamine (8 g), 3-chlorophenylboronic acid (6.5 g) in DME (50 mL) and 2.0 N Na$_2$CO$_3$ (50 mL) was degassed with nitrogen for 15 minutes then tetrakis(triphenylphosphine)palladium (0.6 g) was added and heated at 90° C. for 4 hours under nitrogen. The reaction mass was cooled to room temperature, extracted with ethyl acetate. Combined organic extracts were dried over Na$_2$SO$_4$, filtered, concentrated under reduced pressure and purified on silica gel column. Thus obtained compound was dissolved in methanol and added CNBr (3.2 g). After stirring for 30 minutes at room temperature, evaporated the solvent, the resulting solid was washed with ether and dried to get 5-(3-chlorophenyl)-1H-benzoimidazol-2-ylamine hydrobromide salt (3.3 g). LCMS (m/z): 243.8.

A mixture of 6-chloro-imidazo[1,2-b]pyridazine-2-carboxylic acid (400 mg), HBTU (900 mg) and DIEA (1 mL) in DMF (5 mL) was heated at 80° C. for 10 minutes. To this reaction mixture 5-(3-chlorophenyl)-1H-benzoimidazol-2-ylamine hydrobromide salt (265 mg) was added, and the mixture was heated at 80° C. for 30 minutes. After cooling the reaction mixture to room temperature, an aqueous sodium bicarbonate solution was added, and the mixture was stirred for 30 minutes. The mixture was filtered, washed with water, and purified on silica gel column to obtain 6-chloro-imidazo[1,2-b]pyridazine-2-carboxylic acid [5-(3-chloro-phenyl)-1H-benzoimidazol-2-yl]-amide (635 mg). LC-MS (m/z). 423.7.

6-(2-Hydroxy-ethoxy)-imidazo[1,2-b]pyridazine-2-carboxylic acid [5-(3-chloro-phenyl)-1H-benzoimidazol-2-yl]-amide (41 mg) was prepared from 6-chloro-imidazo[1,2-b]pyridazine-2-carboxylic acid [5-(3-chloro-phenyl)-1H-benzoimidazol-2-yl]-amide (80 mg) and 2-(tetrahydro-pyran-2-yloxy)-ethanol as described in Example 122. LCMS (m/z): 449.7. $^1$H NMR (400 MHz, DMSO-d$_6$): δ 12.38 and 11.4 (1H, s) 8.84 (1H, s) 8.15 (1H, d) 7.78 1H, s) 7.71 (1 h, s) 7.56-7.66 (2H, m) 7.45-7.51 (2H, m) 7.39 (1H, d) 7.07 (1H, d) 4.98 (1H, t) 4.38 (2H, t) 3.79 (2H, q).

Example 145

6-((S)-2-hydroxy-propoxy)-imidazo[1,2-b]pyridazine-2-carboxylic acid [5-(3-trifluoromethoxy-phenyl)-1H-benzoimidazol-2-yl]-amide 6-((S)-2-Hydroxy-propoxy)-imidazo[1,2-b]pyridazine-2-carboxylic acid [5-(3-trifluoro-methoxy-phenyl)-1H-benzoimidazol-2-yl]-amide (27 mg) was prepared from 6-chloro-imidazo[1,2-b]pyridazine-2-carboxylic acid [5-(3-trifluoromethoxy-phenyl)-1H-benzoimidazol-2-yl]-amide (50 mg) and (S)-2-(tetrahydro-pyran-2-yloxy)-propan-1-ol as described in Example 122. LCMS (m/z): 513.9. $^1$H NMR (400 MHz, DMSO-$d_6$): δ 8.83 (1H, s) 8.14 (1H, d) 7.81 (1H, d) 7.73 (1H, d) 7.62 (1H, s) 7.59 (2H, d) 7.49 (1H, dd) 7.32-7.34 (1H, m) 7.07 (1H, d) 4.99 (1H, d) 4.13-4.18 (2H, m) 4.02-4.07 (1H, m) 1.19 (3H, d).

Example 146

6-((1R,2R)-2-hydroxy-1-methyl-propoxy)-imidazo [1,2-b]pyridazine-2-carboxylic acid [5-(3-chloro-5-fluoro-phenyl)-1H-benzoimidazol-2-yl]-amide To a solution of (2R,3R)-butanediol (100 mg) in dry DMF (2 mL) NaH (100 mg, 60% dispersion in mineral oil) was added, and the mixture was stirred at room temperature for 10 minutes under nitrogen. To this mixture 6-chloro-imidazo[1,2-b]pyridazine-2-carboxylic acid [5-(3-chloro-5-fluoro-phenyl)-1H-benzoimidazol-2-yl]-amide (60 mg) was added, and the mixture was stirred at room temperature for 2 hours. Then, 10 mL of water was added and the reaction mixture was stirred for 10 minutes. The reaction was then filtered through a filter paper, washed with water, dried and purified by column chromatography using 0-10% 2 M ammonia-methanol in DCM to obtain 6-((1R,2R)-2-hydroxy-1-methyl-propoxy)-imidazo[1,2-b]pyridazine-2-carboxylic acid [5-(3-chloro-5-fluoro-phenyl)-1H-benzoimidazol-2-yl]-amide (25 mg). LCMS (m/z): 495.9. $^1$H NMR (400 MHz, DMSO-$d_6$) δ 12.40 (1H, brs), 11.42 (1H, brs), 8.80-7.00 (9H, Ar—H), 5.10-4.90 (2H, m), 3.90-3.80 (1H, m), 1.30 (3H, d), 1.13 (3H, d).

Example 147

6-[(S)-1-(Tetrahydro-furan-2-yl)methoxy]-imidazol [1,2-b]pyridazine-2-carboxylic acid [5-(3-chloro-5-fluoro-phenyl)-1H-benzoimidazol-2-yl]-amide To a solution of (S)-(tetrahydrofuran-2-yl-)-methanol (30.6 mg) in dry DMF (1 mL) NaH (12 mg, 60% dispersion in mineral oil) was added, and the mixture was stirred at room temperature for 20 minutes under nitrogen. To this mixture 6-chloro-imidazo[1,2-b]pyridazine-2-carboxylic acid [5-(3-chloro-5-fluoro-phenyl)-1H-benzoimidazol-2-yl]-amide (44.0 mg) was added, and the mixture was warmed to 80° C. The reaction was monitored by LCMS until substantially complete. Then, 10 mL of water was added and the reaction mixture was stirred for 10 minutes. The reaction was then filtered through a fine fritted funnel and the crude product was washed with water. After air drying, the product 6-[(S)-1-(tetrahydro-furan-2-yl)methoxy]-imidazo[1,2-b]pyridazine-2-carboxylic acid [5-(3-chloro-5-fluoro-phenyl)-1H-benzoimidazol-2-yl]-amide (24.8 mg) was purified by column chromatography (prepacked silica column) using 9:1 DCM and 2N ammonia in methanol. LCMS (m/z): 507.9. $^1$H NMR (400 MHz, CDCl$_3$) δ 11.23 (1H, br. s.) 10.25-10.73 (1H, m) 8.40 (1H, s) 7.74 (2H, d) 7.38-7.44 (2H, m) 7.19-7.25 (2H, m) 7.04 (1H, dt) 6.83-6.89 (1H, m) 4.24-4.42 (3H, m) 3.82-4.03 (2H, m) 1.91-2.17 (2H, m) 1.67-1.82 (2H, m).

Example Compounds

Table 1 shows examples of compounds of Formula (I) or pharmaceutically acceptable salts thereof that were synthesized. Each of the identified compounds constitutes a separate embodiment of the invention, where the embodiments include the compound in its free (non-salted) form, tautomers of the compound in its free (non-salted form), and pharmaceutically acceptable salts of either of the foregoing. In other embodiments, each of the recited compounds is in its free (non-salted) form constitutes a separate embodiment of the invention, including tautomers of each of the compounds. In other embodiments, the pharmaceutically acceptable salts of each of the recited compounds constitute a separate embodiment of the invention, including pharmaceutically acceptable salts of the tautomers of each of the compounds. In other embodiments, the hydrochloride salts of each of the recited compounds constitute a separate embodiment of the invention, including hydrochloride salts of the tautomers of said compounds. Table 1 shows LC-MS data for each compound. The recorded m/z data are accurate to within about 1 amu. For some examples, proton NMR spectra were also recorded, although such data are not shown. Table 1 shows a generic structure, and identifies each compound by the identity of its substituents.

The LCMS (m/z) data are obtained using gradient elution on a parallel MUX™ system, running four Waters® 1525 binary HPLC pumps, equipped with a Mux-UV 2488 multi-channel UV-Vis detector (recording at 215 and 254 nM) and a Leap Technologies HTS PAL Auto sampler using a Sepax GP-C18, 4.6×50 mm; 5 micron particle-size column. A three minute gradient is run from 25% B (97.5% acetonitrile, 2.5% water, 0.05% TFA) and 75% A (97.5% water, 2.5% acetonitrile, 0.05% TFA) to 100% B. The system is interfaced with a Waters Micromass ZQ mass spectrometer using electrospray ionization. MassLynx software is employed.

TABLE 1

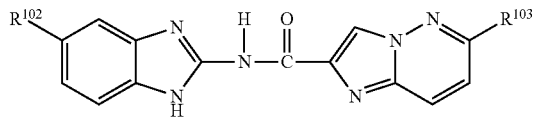

| Example | $R^{102}$ | $R^{103}$ | LCMS (m/z) |
|---|---|---|---|
| 1 | —O—CH$_2$-phenyl | Cl | 417.6 |
| 2 | —O—CH$_2$-(4-Cl-phenyl) | Cl | 451.6 |
| 3 | —O—CH$_2$-(4-CF$_3$-phenyl) | Cl | 485.7 |
| 4 | —O—CH$_2$-phenyl | methoxy | 415.6 |
| 5 | —O—CH$_2$-(4-CF$_3$-phenyl) | methoxy | 483.6 |
| 6 | —O—CH$_2$-phenyl | methyl | 399.7 |
| 7 | 3-Cl-5-F-phenyl | methoxy | 437.8 |

TABLE 1-continued

| Example | R¹⁰² | R¹⁰³ | LCMS (m/z) |
|---|---|---|---|
| 8 | 3-CF₃-phenyl | 2-(methoxy)-ethoxy | 497.8 |
| 9 | 3-(OCF₃)-phenyl | —NH—CH₃ | 468.9 |
| 10 | 3-(OCF₃)-phenyl | —N(CH₃)₂ | 482.8 |
| 11 | 3-CF₃-phenyl | —O—(CH₂)₂—O—(CH₂)₂—O—CH₂CH₃ | 555.8 |
| 12 | 3-CF₃-phenyl | —O—(CH₂)₂—N(CH₃)₂ | 510.9 |
| 13 | 3-CF₃-phenyl | —O—(CH₂)₃—OCH₂CH₃ | 525.8 |
| 14 | 3-Cl-5-F-phenyl | —O—(CH₂)₂—NH—CH₃ | 480.8 |
| 15 | 3-Cl-5-F-phenyl | —O—(CH₂)₂—N(CH₃)₂ | 494.8 |
| 16 | 3-Cl-5-F-phenyl | 4-tetrahydropyranyloxy | 507.8 |
| 17 | 3-Cl-5-F-phenyl | —O—(CH₂)₃—N(CH₃)₂ | 508.8 |
| 18 | 3-Cl-5-F-phenyl | 1-methyl-piperidin-4-yloxy | 520.7 |
| 19 | 3-Cl-5-F-phenyl | —O—(CH₂)₂-(pyrrolidin-1-yl) | 520.8 |
| 20 | 3-Cl-5-F-phenyl | —O—(CH₂)₃—N(CH₂CH₃)₂ | 536.9 |
| 21 | 3-(OCF₃)-phenyl | —O—(CH₂)₂-(pyrrolidin-1-yl) | 552.8 |
| 22 | 3-CF₃-phenyl | 2-(ethoxy)-ethoxy | 511.7 |
| 23 | 3-CF₃-phenyl | 2-(isopropoxy)-ethoxy | 525.8 |
| 24 | 3-CF₃-phenyl | —O—(CH₂)₂—NH—C(CH₃)₃ | 538.8 |
| 25 | 3-CF₃-phenyl | —O—(CH₂)₂-(2-oxo-pyrrolidin-1-yl) | 550.7 |
| 26 | 3-CF₃-phenyl | —O—(CH₂)₂-(2-oxo-imidazolidin-1-yl) | 551.7 |
| 27 | 3-CF₃-phenyl | —O—(CH₂)₂-(morpholin-4-yl) | 552.8 |
| 28 | 3-(OCF₃)-phenyl | —O—(CH₂)₂—NH—CH(CH₃)₂ | 540.7 |
| 29 | 3-(OCF₃)-phenyl | —O—(CH₂)₂-(1,2,4-triazol-1-yl) | 550.7 |
| 30 | 3-(OCF₃)-phenyl | —O—(CH₂)₂—NH—C(CH₃)₃ | 554.8 |
| 31 | 3-(OCF₃)-phenyl | —O—(CH₂)₂-(2-oxo-pyrrolidin-1-yl) | 566.7 |
| 32 | 3-(OCF₃)-phenyl | —O—(CH₂)₂-(morpholin-4-yl) | 568.8 |
| 33 | 3-(OCF₃)-phenyl | —O—(CH₂)₂—NH-(cyclohexyl) | 580.8 |
| 34 | 3-(OCF₃)-phenyl | —O—(CH₂)₂-(azepan-1-yl) | 580.8 |
| 35 | 3-(OCF₃)-phenyl | —O—(CH₂)₂-(4-methyl-piperazin-1-yl) | 581.8 |
| 36 | 3-(OCF₃)-phenyl | —O—(CH₂)₂—N(CH₃)—(CH₂)₂—N(CH₃)₂ | 583.8 |
| 37 | 3-(OCF₃)-phenyl | —O—(CH₂)₂—N(CH₃)-(2-pyridyl) | 589.7 |
| 38 | 3-CF₃-phenyl | —O—(CH₂)₂—NH—CH(CH₃)₂ | 524.7 |
| 39 | 3-CF₃-phenyl | —O—(CH₂)₂—NH-(cyclohexyl) | 564.8 |
| 40 | 3-CF₃-phenyl | —O(CH₂)₂-(azepan-1-yl) | 564.8 |
| 41 | 3-CF₃-phenyl | —O—(CH₂)₂-(4-methyl-piperazin-1-yl) | 565.7 |
| 42 | 3-CF₃-phenyl | —O—(CH₂)₂—N(CH(CH₃)₂)₂ | 566.9 |
| 43 | 3-CF₃-phenyl | —O—(CH₂)₂—N(CH₃)—(CH₂)₂—N(CH₃)₂ | 567.8 |
| 44 | 3-CF₃-phenyl | —O—(CH₂)₂—N(CH₃)-(2-pyridyl) | 573.8 |
| 45 | 3-CF₃-phenyl | —O—(CH₂)₂-(1,2,4-triazol-1-yl) | 534.7 |
| 46 | 3-CF₃-phenyl | —O—(CH₂)₂-(piperidin-1-yl) | 550.8 |
| 47 | 3-(OCF₃)-phenyl | 2-(piperidin-1-yl)-ethoxy | 566.8 |
| 48 | 3-Cl-5-F-phenyl | —O—(CH₂)₂—N(CH(CH₃)₂)₂ | 550.8 |
| 49 | 3-Cl-5-F-phenyl | —O—(CH₂)₂—N(CH₃)—(CH₂)₂—N(CH₃)₂ | 551.8 |
| 50 | 3-Cl-5-F-phenyl | —O—(CH₂)₂-(morpholin-4-yl) | 536.7 |
| 51 | 3-Cl-5-F-phenyl | —O—(CH₂)₂—NH-(cyclohexyl) | 548.7 |
| 52 | 3-Cl-5-F-phenyl | —O—(CH₂)₂—NH—C(CH₃)₃ | 522.7 |
| 53 | 3-Cl-5-F-phenyl | —O—(CH₂)₂-(azepan-1-yl) | 548.7 |
| 54 | 3-Cl-5-F-phenyl | —O—(CH₂)₂-(2-oxo-pyrrolidin-1-yl) | 534.7 |
| 55 | 3-Cl-5-F-phenyl | —O—(CH₂)₂-(4-methyl-piperazin-1-yl) | 549.7 |
| 56 | 3-(OCF₃)-phenyl | —O—(CH₂)₂—O—(CH₂)₂—N(CH₃)₂ | 570.8 |
| 57 | 3-(OCF₃)-phenyl | —O—(CH₂)₂—NH₂ | 498.8 |
| 58 | 3-CF₃-4-Cl-phenyl | Cl | 491.7 |
| 59 | 3-CF₃-phenyl | —O—(CH₂)₂—O—(CH₂)₂—N(CH₃)₂ | 554.9 |
| 60 | 3-CF₃-phenyl | —O—(CH₂)₂—NH₂ | 482.7 |
| 61 | 3-CF₃-4-Cl-phenyl | methoxy | 469.8 |
| 62 | 3-CF₃-4-Cl-phenyl | 2-(methoxy)-ethoxy | 531.6 |
| 63 | 3-CF₃-4-Cl-phenyl | —O—(CH₂)₂—N(CH₃)₂ | 544.7 |
| 64 | 3-CF₃-4-Cl-phenyl | —O—(CH₂)₂-(morpholin-4-yl) | 586.7 |
| 65 | 3-CF₃-phenyl | morpholin-4-yl | 508.8 |
| 66 | 3-CF₃-phenyl | methoxy | 453.8 |
| 67 | 3-CF₃-phenyl | 4-methyl-piperazin-1-yl | 521.9 |
| 68 | 3-Cl-5-F-phenyl | (2S)-1-methyl-pyrrolidin-2-yl-methoxy | 520.7 |
| 69 | 3-Cl-5-F-phenyl | (3S)-1-methyl-pyrrolidin-3-yloxy | 506.6 |
| 70 | 3-CF₃-phenyl | —O—(CH₂)₂—NH—CH₃ | 496.7 |
| 71 | 3-CF₃-phenyl | —O—(CH₂)₂-(pyrrolidin-1-yl) | 536.8 |
| 72 | 3-CF₃-phenyl | —O—(CH₂)₃—N(CH₃)₂ | 524.8 |
| 73 | 3-CF₃-phenyl | (2R)-2-NH₂-n-propoxy | 496.8 |
| 74 | 3-CF₃-phenyl | (2S)-2-NH₂-n-propoxy | 496.7 |
| 75 | 3-CF₃-phenyl | (3S)-piperidin-3-yloxy | 522.8 |
| 76 | 3-CF₃-phenyl | (3R)-3-NH₂-pyrrolidin-1-yl | 507.8 |
| 77 | 3-CF₃-phenyl | (3S)-3-NH₂-pyrrolidin-1-yl | 507.8 |

TABLE 1-continued

| Example | R¹⁰² | R¹⁰³ | LCMS (m/z) |
|---|---|---|---|
| 78 | 3-CF₃-phenyl | —NH-((3S)-pyrrolidin-3-yl) | 507.8 |
| 79 | 3-CF₃-phenyl | (3R)-3-NH₂-piperidin-1-yl | 521.9 |
| 80 | 3-CF₃-phenyl | piperazin-1-yl | 507.7 |
| 81 | 4-methyl-cyclohexyl | morpholin-4-yl | 460.9 |
| 82 | 4,4-dimethyl-cyclohexyl | piperidin-4-yl | 472.9 |
| 83 | 4,4-dimethyl-cyclohexyl | 4-OH-piperidin-1-yl | 488.8 |
| 84 | 4,4-dimethyl-cyclohexyl | 3-OH-piperidin-1-yl | 488.8 |
| 85 | 4,4-dimethyl-cyclohexyl | (3R)-3-OH-pyrrolidin-1-yl | 474.9 |
| 86 | 4,4-dimethyl-cyclohexyl | (3S)-3-OH-pyrrolidin-1-yl | 474.9 |
| 87 | 4,4-dimethyl-cyclohexyl | 4-methoxy-piperidin-1-yl | 502.9 |
| 88 | 4,4-dimethyl-cyclohexyl | 4-OH-cyclohexyloxy | 503.7 |
| 89 | 4,4-dimethyl-cyclohexyl | (3R)-3-methoxy-pyrrolidin-1-yl | 488.9 |
| 90 | 5-methyl-thiophen-2-yl | (3R)-3-methoxy-pyrrolidin-1-yl | 474.9 |
| 91 | 5-methyl-thiophen-2-yl | (3S)-3-methoxy-pyrrolidin-1-yl | 474.9 |
| 92 | 3-Cl-5-F-phenyl | 4-OH-cyclohexyloxy | 521.7 |
| 93 | 3-Cl-5-F-phenyl | 3-OH-cyclohexyloxy | 521.7 |
| 94 | 3-Cl-5-F-phenyl | 3-OH-cyclopentyloxy | 507.6 |
| 95 | cyclopentyl | (3R)-3-OH-pyrrolidin-1-yl | 432.8 |
| 96 | 3-Cl-phenyl | —NH—(CH₂)₂—CO₂H | 477.0 |
| 97 | 3-CF₃-phenyl | —O—CH₂—CO₂H | 497.7 |
| 98 | 3-Cl-5-F-phenyl | (3-methyl-oxetan-3-yl)methoxy | 507.9 |
| 99 | 3-CF₃-phenyl | (1R,2S)-2-hydroxy-1-methyl-n-propoxy | 511.8 |
| 100 | 3-CF₃-phenyl | (1R,2R)-2-hydroxy-1-methyl-n-propoxy | 511.8 |
| 101 | 3-CF₃-phenyl | (1S,2S)-2-hydroxy-1-methyl-n-propoxy | 511.8 |
| 102 | 3-OCF₃-phenyl | (S)-1-hydroxyprop-2-yloxy | 513.9 |
| 103 | 3-OCF₃-phenyl | (R)-1-hydroxyprop-2-yloxy | 513.6 |
| 104 | 3-Cl-5-F-phenyl | (1-(hydroxymethyl)cyclopropyl)methoxy | 507.8 |
| 105 | 3-Cl-5-F-phenyl | (2R)-2-hydroxy-n-butoxy | 496.0 |
| 106 | 3-Cl-5-F-phenyl | (2S)-2-hydroxy-n-butoxy | 495.9 |
| 107 | 3-Cl-5-F-phenyl | (2R)-2-hydroxy-3-methyl-n-butoxy | 509.8 |
| 108 | 3-Cl-5-F-phenyl | (2S)-2-hydroxy-3-methyl-n-butoxy | 509.7 |
| 109 | 3-CF₃-phenyl | 3-hydroxy-2,2-dimethyl-n-propoxy | 525.9 |
| 110 | 3-CF₃-phenyl | 3-(dimethylamino)-2-hydroxy-n-propoxy | 540.8 |
| 111 | 3-CF₃-phenyl | (2R)-2-fluoro-n-propoxy | 499.9 |
| 112 | 3-OCF₃-phenyl | 2-hydroxy-2-methyl-n-propoxy | 527.8 |
| 113 | 3-Cl-5-F-phenyl | 3-hydroxy-n-propoxy | 481.9 |
| 114 | 3-Cl-5-F-phenyl | 3-hydroxy-3-methyl-n-butoxy | 509.8 |
| 115 | 3-OCF₃-phenyl | 1-(hydroxymethyl)-2-hydroxyethoxy | 529.9 |
| 116 | 3-OCF₃-phenyl | tetrahydrofuran-3-yl-methyloxy | 539.9 |
| 117 | 3-CF₃-phenyl | (1R)-1-(CH₂OH)-2-methoxyethoxy | 527.9 |
| 118 | 3-Cl-5-F-phenyl | (3R)-3-hydroxy-n-butoxy | 495.9 |
| 119 | 3-Cl-5-F-phenyl | (3S)-3-hydroxy-n-butoxy | 495.9 |
| 120 | 3-CF₃-phenyl | (1R,3R)-3-hydroxy-1-methyl-n-butoxy | 526.1 |
| 121 | 3-CF₃-phenyl | (1S,3S)-3-hydroxy-1-methyl-n-butoxy | 526.0 |
| 122 | 3-Cl-4-CF₃-phenyl | (2R)-2-hydroxy-n-propoxy | 532.0 |
| 123 | 3-Cl-4-CF₃-phenyl | (2S)-2-hydroxy-n-propoxy | 532.0 |
| 124 | 3-Cl-5-F-phenyl | (2R)-2-hydroxy-n-pentyloxy | 509.8 |
| 125 | 3-Cl-5-F-phenyl | (2S)-2-hydroxy-n-pentyloxy | 509.6 |
| 126 | 3-CF₃-phenyl | (2R)-2-hydroxy-n-hexyloxy | 539.9 |
| 127 | 3-Cl-5-F-phenyl | (2S)-2-hydroxy-n-hexyloxy | 524.0 |
| 128 | 3-CF₃-phenyl | 2,2-difluoro-3-hydroxy-n-propoxy | 533.9 |

TABLE 1-continued

[Structure: R¹⁰²-benzimidazol-2-yl-NH-C(O)-imidazo[1,2-b]pyridazine-R¹⁰³]

| Example | R¹⁰² | R¹⁰³ | LCMS (m/z) |
|---|---|---|---|
| 129 | 3-Cl-5-F-phenyl | (3R)-3,4-dihydroxy-n-butoxy | 512.0 |
| 130 | 3-Cl-5-F-phenyl | 4-hydroxy-n-butoxy | 495.9 |
| 131 | 3-Cl-4-F-phenyl | 2-hydroxyethoxy | 467.8 |
| 132 | 3-Cl-5-F-phenyl | [cyclobutane-1,1-diyl-bis(methyleneoxy/hydroxy) group] | 522.1 |
| 133 | 3-Cl-5-F-phenyl | [hexahydrofuro[3,2-b]furan-diol ether] | 551.4 |
| 134 | 3-OCF₃-phenyl | [tetrahydrofuran-2,5-diyl-bis(methyleneoxy/hydroxy)] | 569.2 |
| 135 | 3-CF₃-phenyl | [1,3-dimethoxy-2-propyloxy substituent] | 540.7 |
| 136 | 3-OCF₃-phenyl | —S—(CH₂)₂—OH | 516.0 |
| 137 | 3-CF₃-phenyl | 2-fluoro-3-hydroxy-n-propoxy | 516.1 |
| 138 | 3-CF₃-phenyl | 3-fluoro-n-propoxy | 500.1 |
| 139 | 3-CF₃-phenyl | (4R)-4-hydroxy-n-pentyloxy | 526.1 |
| 140 | 3-CF₃-phenyl | —O—CH₂—CN | 479.1 |
| 141 | 3-CF₃-phenyl | —O—CH₂—C(O)—N(CH₃)₂ | 524.4 |
| 142 | 3-Cl-5-F-phenyl | 4-(OH)-piperidin-1-yl | 506.7 |
| 143 | 3-OCF₃-phenyl | 2-hydroxyethoxy | 473.9 |
| 144 | 3-Cl-phenyl | 2-hydroxyethoxy | 449.7 |
| 145 | 3-OCF₃-phenyl | (2S)-2-hydroxy-n-propoxy | 513.9 |
| 146 | 3-Cl-5-F-phenyl | (1R,2R)-2-hydroxy-1-methyl-n-propoxy | 495.9 |
| 147 | 3-Cl-5-F-phenyl | [(tetrahydrofuran-2-yl)methoxy] | 507.9 |

Compounds in Table 1 having a basic group or acidic group are depicted as the free base or acid. Depending on the reaction conditions and purification conditions, various compounds in Table 1 having a basic or acidic group may have been isolated in either the free base form, as a salt (such as an HCl salt), or in both forms.

As shown in Tables 2 and 3, below, compounds of the invention inhibit β-secretase enzyme activity. Compounds that inhibit β-secretase enzyme activity are potentially useful in treating diseases or conditions that may be associated with the build-up of β-amyloid plaques, including, but not limited to, Alzheimer's disease, mild cognitive impairment, dementia of Alzheimer's type, Down's syndrome, Hereditary Cerebral Hemorrhage with Amyloidosis of the Dutch-Type, cerebral amyloid angiopathy, degenerative dementia, diffuse Lewy body type of Alzheimer's disease, and central or peripheral amyloid diseases.

The compounds of Formula (I), tautomers of compounds of Formula (I), and/or pharmaceutically acceptable salts of either of the foregoing, may therefore be useful in the treatment of one or more of these diseases.

In one embodiment, the present invention provides a pharmaceutical composition comprising a compound of Formula (I), a tautomer of a compound of Formula (I), or pharmaceutically acceptable salts of either of the foregoing. In another embodiment, the present invention provides a pharmaceutical composition comprising a compound, tautomer, or pharmaceutically acceptable salt of any one of embodiments 1 to 249 (recited above). In another embodiment, the pharmaceutical composition comprises a compound, tautomer, or pharmaceutically acceptable salt of any one of embodiments 1 to 249 and a pharmaceutically acceptable carrier, excipient, diluent, or a mixture thereof.

In an embodiment, the pharmaceutical compositions containing a compound of Formula (I), a tautomer of a compound of Formula (I), or a pharmaceutically acceptable salt of either of the foregoing, may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, to form osmotic therapeutic tablets for controlled release.

In another embodiment, formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

In another embodiment, the composition may comprise an aqueous suspension. Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Also, oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

In another embodiment, the pharmaceutical compositions of the present invention may comprise a syrup or elixir. Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The pharmaceutical compositions of the present invention may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

In an embodiment, for topical use, creams, ointments, jellies, solutions of suspensions, etc., containing the compounds of the invention may be employed. For the purpose of this application, topical applications shall include mouth washes and gargles.

In an embodiment, the compounds of Formula (I), tautomers of compounds of Formula (I), or pharmaceutically acceptable salts of either of the foregoing may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Pharmaceutically-acceptable salts of compounds of Formula (I) or tautomers of compound of Formula (I), where a basic or acidic group is present in the structure, are also included within the scope of the invention. The term "pharmaceutically acceptable salts" refers to salts of the compounds of this invention which are not biologically or otherwise undesirable and are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrocloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxalate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts listed in Berge et al., *J. Pharm. Sci.*, 66:1-19 (1977).

In another embodiment, the invention provides a pharmaceutical composition comprising a compound of Formula (I), a tautomer of a compound of Formula (I), or a pharmaceutically acceptable salt of either of the foregoing, and one or more pharmaceutically acceptable carriers, excipients, or diluents. In another embodiment, the invention provides a pharmaceutical composition comprising a compound, tautomer, or pharmaceutically acceptable salt of any one of embodiments 1 to 249 and one or more pharmaceutically acceptable carriers, excipients, or diluents.

In another embodiment, the present invention provides a compound of Formula (I), a tautomer of a compound of Formula (I), or a pharmaceutically acceptable salt of either of the foregoing for use in medicine. In another embodiment, the invention provides a compound, tautomer, or pharmaceutically acceptable salt of any one of embodiments 1 to 249 for use in medicine.

The present invention further provides for the use of a compound of Formula (I), a tautomer of a compound of Formula (I), or a pharmaceutically acceptable salt of either of the foregoing, in combination with one or more medically effective active compounds for simultaneous, subsequent, or sequential administration. The invention also provides for the use of a compound, tautomer, or pharmaceutically acceptable salt of any one of embodiments 1 to 249 in combination with one or more medically effective active compounds for simultaneous, subsequent, or sequential administration.

Examples of such medically effective active ingredients include, but are not limited to, β-secretase inhibitors, γ-secretase inhibitors, HMG-CoA reductase inhibitors, non-steroidal anti-inflammatory drugs (NSAIDs) (including but not limited to ibuprofen, naproxen, and diclofenac), N-methyl-D-aspartate (NMDA) receptor agonists (including but not limited to memantine), cholinesterase inhibitors (including but not limited to galantamine, rivastigmine, donepezil, and tacrine), vitamin E, CB-1 receptor antagonists, CB-1 receptor inverse agonists, antibiotics (including but not limited to doxycycline and rifampin), agents that bind Aβ or that induce antibodies that bind Aβ, anti-Aβ antibodies, Aβ vaccines, and RAGE/RAGE ligand interaction antagonists, and other drugs that affect receptors or enzymes that either increase the efficacy, safety, convenience, or reduce unwanted side effects or toxicity of the compounds of the present invention. In one embodiment, the invention provides a pharmaceutical composition comprising a compound, tautomer, or pharmaceutically acceptable salt of any one of embodiments 1 to 249 and at least one other medically effective active ingredient selected from β-secretase inhibitors, γ-secretase inhibitors, HMG-CoA reductase inhibitors, non-steroidal anti-inflammatory drugs (NSAIDs) (including but not limited to ibuprofen, naproxen, and diclofenac), N-methyl-D-aspartate (NMDA) receptor agonists (including but not limited to memantine), cholinesterase inhibitors (including but not limited to galantamine, rivastigmine, donepezil, and tacrine), vitamin E, CB-1 receptor antagonists, CB-1 receptor inverse agonists, antibiotics (including but not limited to doxycycline and rifampin), agents that bind Aβ or that induce antibodies that bind Aβ, anti-Aβ antibodies, Aβ vaccines, and RAGE/RAGE ligand interaction antagonists. In another embodiment, the invention provides for the use of a compound, tautomer, or pharmaceutically acceptable salt of any one of embodiments 1 to 249 in combination with at least one other medically effective active ingredient selected from β-secretase inhibitors, γ-secretase inhibitors, HMG-CoA reductase inhibitors, non-steroidal anti-inflammatory drugs (NSAIDs) (including but not limited to ibuprofen, naproxen, and diclofenac), N-methyl-D-aspartate (NMDA) receptor agonists (including but not limited to memantine), cholinesterase inhibitors (including but not limited to galantamine, rivastigmine, donepezil, and tacrine), vitamin E, CB-1 receptor antagonists, CB-1 receptor inverse agonists, antibiotics (including but not limited to doxycycline and rifampin), agents that bind Aβ or that induce antibodies that bind Aβ, anti-Aβ antibodies, Aβ vaccines, and RAGE/RAGE ligand interaction antagonists, for simultaneous, subsequent, or sequential administration.

Methods of Use

A compound of Formula (I) or pharmaceutically acceptable salt thereof, or a pharmaceutical composition comprising a compound of Formula (I), a tautomer of a compound of Formula (I), or a pharmaceutically acceptable salt of either of the foregoing, may be used for the treatment of a disorder selected from Alzheimer's disease, mild cognitive impairment, dementia of Alzheimer's type, Down's syndrome, Hereditary Cerebral Hemorrhage with Amyloidosis of the Dutch-Type, cerebral amyloid angiopathy, degenerative dementia, diffuse Lewy body type of Alzheimer's disease, and central or peripheral amyloid diseases.

In one embodiment, the invention provides a method of treatment comprising administering a compound, tautomer, or pharmaceutically acceptable salt of any one of embodiments 1 to 249 to a human. In another embodiment, the invention provides a method of treatment comprising administering at least 0.1 milligrams of a compound, tautomer, or pharmaceutically acceptable salt of any one of embodiments 1 to 249 to a human.

In another embodiment, the invention provides a method of treatment comprising administering a compound, tautomer, or pharmaceutically acceptable salt of any one of embodiments 1 to 249 to a human, so as to treat at least one disorder selected from Alzheimer's disease, mild cognitive impairment, dementia of Alzheimer's type, Down's syndrome, Hereditary Cerebral Hemorrhage with Amyloidosis of the Dutch-Type, cerebral amyloid angiopathy, degenerative dementia, diffuse Lewy body type of Alzheimer's disease, and central or peripheral amyloid diseases. In another embodiment, the invention provides a method of treatment comprising administering a compound, tautomer, or pharmaceutically acceptable salt of any one of embodiments 1 to 249 to a human, so as to treat Alzheimer's disease. In another embodiment, the invention provides a method of treatment comprising administering a compound, tautomer, or pharmaceutically acceptable salt of any one of embodiments 1 to 249 to a human, so as to treat mild cognitive impairment. In another embodiment, the invention provides a method of treatment comprising administering a compound, tautomer, or pharmaceutically acceptable salt of any one of embodiments 1 to 249 to a human, so as to treat dementia of Alzheimer's type. In another embodiment, the invention provides a method of treatment comprising administering a compound, tautomer, or pharmaceutically acceptable salt of any one of embodiments 1 to 249 to a human, so as to treat cerebral amyloid angiopathy.

As used herein, "Alzheimer's Disease" is a disorder that may be diagnosed by NINCDS and DSM criteria, Mini-Mental State Examination, and Clinical Dementia Rating within particular limits.

In another embodiment, the invention provides a method of treatment comprising administering a compound, tautomer, or pharmaceutically acceptable salt of any one of embodiments 1 to 249 to a human, so as to improving cognitive performance. Cognitive performance may be assessed with the cognitive subscale of the Alzheimer's Disease Assessment Scale (ADAS-cog), as is known in the art, which scores cognitive function on a 0 to 70 scale, with higher scores indicating greater cognitive impairment. Thus, a reduction in score demonstrates cognitive improvement. In another embodiment, the invention provides a method of treatment comprising administering a compound, tautomer, or pharmaceutically acceptable salt of any one of embodiments 1 to 249 to a human, so as to reduce an ADAS-cog score in a subject with an abnormally high score. In another embodiment, the invention provides a method of treatment comprising administering a compound, tautomer, or pharmaceutically acceptable salt of any one of embodiments 1 to 249 to a human so as to maintain an ADAS-cog score in a subject. In another embodiment, the invention provides a method of treatment comprising administering a compound, tautomer, or pharmaceutically acceptable salt of any one of embodiments 1 to 249 to a human, so as to decrease the rate of increase in an ADAS-cog score in a subject. In each of these embodiments, the subject may be suffering from dementia of the Alzheimer's type. In a further embodiment, the subject may be suffering from dementia of the Alzheimer's type with early onset uncomplicated, dementia of the Alzheimer's type with early onset with delusions, dementia of the Alzheimer's type with early onset with depressed mood, dementia of the Alzheimer's type with late onset uncomplicated, dementia of the Alzheimer's type with late onset with delusions, or dementia of the Alzheimer's type with late onset with depressed mood.

In addition, the progression of Alzheimer's Disease may also be assessed through examination of four areas of patient function: General, Cognitive, Behavioral, and Activities of Daily Living. Such an assessment may be performed using a Clinician's Interview Based Impression of Change (CIBIC or CIBIC plus). In another embodiment, the present invention provides a method for improvement in a subject's function comprising administering a compound, tautomer, or pharmaceutically acceptable salt of any one of embodiments 1 to 249 to a human. In an embodiment, the subject's function is one or more of general, cognitive, behavioral, and activities of daily living.

In another embodiment, the invention provides a compound, tautomer, or pharmaceutically acceptable salt of any one of embodiments 1 to 249 for use in medicine. In another embodiment, the invention provides a compound, tautomer, or pharmaceutically acceptable salt of any one of embodiments 1 to 249 for use in the treatment of at least one disorder selected from Alzheimer's disease, mild cognitive impairment, dementia of Alzheimer's type, Down's syndrome, Hereditary Cerebral Hemorrhage with Amyloidosis of the Dutch-Type, cerebral amyloid angiopathy, degenerative dementia, diffuse Lewy body type of Alzheimer's disease, and central or peripheral amyloid diseases. In another embodiment, the invention provides a compound, tautomer, or pharmaceutically acceptable salt of any one of embodiments 1 to 249 for use in the treatment of Alzheimer's disease. In another embodiment, the invention provides a compound, tautomer, or pharmaceutically acceptable salt of any one of embodiments 1 to 249 for use in the treatment of mild cognitive impairment. In another embodiment, the invention provides a compound, tautomer, or pharmaceutically acceptable salt of any one of embodiments 1 to 249 for use in the treatment of dementia of Alzheimer's type. In another embodiment, the invention provides a compound, tautomer, or pharmaceutically acceptable salt of any one of embodiments 1 to 249 for use in the treatment of cerebral amyloid angiopathy.

In another embodiment, the invention provides a compound, tautomer, or pharmaceutically acceptable salt of any one of embodiments 1 to 249 for use in the prevention of at least one disorder selected from Alzheimer's disease, mild cognitive impairment, dementia of Alzheimer's type, Down's syndrome, Hereditary Cerebral Hemorrhage with Amyloidosis of the Dutch-Type, cerebral amyloid angiopathy, degenerative dementia, diffuse Lewy body type of Alzheimer's disease, and central or peripheral amyloid diseases. In another embodiment, the invention provides a compound, tautomer, or pharmaceutically acceptable salt of any one of embodiments 1 to 249 for use in the prevention of Alzheimer's disease. In another embodiment, the invention provides a compound, tautomer, or pharmaceutically acceptable salt of any one of embodiments 1 to 249 for use in the prevention of mild cognitive impairment. In another embodiment, the invention provides a compound, tautomer, or pharmaceutically acceptable salt of any one of embodiments 1 to 249 for use in the prevention of dementia of Alzheimer's type. In another embodiment, the invention provides a compound, tautomer, or pharmaceutically acceptable salt of any one of embodiments 1 to 249 for use in the prevention of cerebral amyloid angiopathy.

In another embodiment, the invention provides a compound, tautomer, or pharmaceutically acceptable salt of any one of embodiments 1 to 249 for use in the improvement of cognitive performance. In another embodiment, the invention provides a compound, tautomer, or pharmaceutically acceptable salt of any one of embodiments 1 to 249 for use in the reduction of an ADAS-cog score in a subject with an abnormally high score. In another embodiment, the invention provides a compound, tautomer, or pharmaceutically acceptable salt of any one of embodiments 1 to 249 for use in the maintenance of an ADAS-cog score in a subject. In another embodiment, the invention provides a compound, tautomer, or pharmaceutically acceptable salt of any one of embodiments 1 to 249 for use in decreasing the rate of increase in an ADAS-cog score in a subject. In another embodiment, the invention provides a compound, tautomer, or pharmaceutically acceptable salt of any one of embodiments 1 to 249 for use in the improvement of subject function in one or more of general, cognitive, behavioral, and activities of daily living.

In another embodiment, the invention provides for the use of a compound, tautomer, or pharmaceutically acceptable salt of any one of embodiments 1 to 249 for the preparation of a medicament. In another embodiment, the invention provides for the use of a compound, tautomer, or pharmaceutically acceptable salt of any one of embodiments 1 to 249 for the preparation of a medicament for the treatment of at least one disorder selected from Alzheimer's disease, mild cognitive impairment, dementia of Alzheimer's type, Down's syndrome, Hereditary Cerebral Hemorrhage with Amyloidosis of the Dutch-Type, cerebral amyloid angiopathy, degenerative dementia, diffuse Lewy body type of Alzheimer's disease, and central or peripheral amyloid diseases. In another embodiment, the invention provides for the use of a compound, tautomer, or pharmaceutically acceptable salt of any one of embodiments 1 to 249 for the preparation of a medicament for the treatment of Alzheimer's disease. In another embodiment, the invention provides for the use of a compound, tautomer, or pharmaceutically acceptable salt of any one of embodiments 1 to 249 for the preparation of a medicament for the treatment of mild cognitive impairment. In another embodiment, the invention provides for the use of a compound, tautomer, or pharmaceutically acceptable salt of any one of embodiments 1 to 249 for the preparation of a medicament for the treatment of dementia of Alzheimer's type. In another embodiment, the invention provides for the use of a compound, tautomer, or pharmaceutically acceptable salt of any one of embodiments 1 to 249 for the preparation of a medicament for the treatment of cerebral amyloid angiopathy.

In another embodiment, the invention provides for the use of a compound, tautomer, or pharmaceutically acceptable salt of any one of embodiments 1 to 249 for the preparation of a medicament for improving cognitive performance. In another embodiment, the invention provides for the use of a compound, tautomer, or pharmaceutically acceptable salt of any one of embodiments 1 to 249 for the preparation of a medicament for reducing an ADAS-cog score in a subject with an abnormally high score. In another embodiment, the invention provides for the use of a compound, tautomer, or pharmaceutically acceptable salt of any one of embodiments 1 to 249 for the preparation of a medicament for the maintaining an ADAS-cog score in a subject. In another embodiment, the invention provides for the use of a compound, tautomer, or pharmaceutically acceptable salt of any one of embodiments 1 to 249 for the preparation of a medicament for decreasing the rate of increase in an ADAS-cog score in a subject. In another embodiment, the invention provides for the use of a compound, tautomer, or pharmaceutically acceptable salt of any one of embodiments 1 to 249 for the preparation of a medicament for improving subject function in one or more of general, cognitive, behavioral, and activities of daily living.

In another embodiment, the present invention provides a method for inhibiting the interaction of BACE with a physiological ligand. An example of a physiological ligand of BACE includes, but is not limited to, amyloid precursor protein (APP). In one embodiment, the invention provides a method for treating Alzheimer's Disease or dementia of the Alzheimer's type comprising: administering a compound, tautomer, or pharmaceutically acceptable salt of any one of embodiments 1 to 249 to a human, so as to inhibit the interaction of BACE with a physiological ligand. In one embodiment, the physiological ligand is amyloid precursor protein (APP). In a further embodiment, the invention provides a compound, tautomer, or pharmaceutically acceptable salt of any one of embodiments 1 to 249 for use in the inhibition of the interaction of BACE with a physiological ligand. In a further embodiment, the invention provides for the use of a compound, tautomer, or pharmaceutically acceptable salt of any one of embodiments 1 to 249 for the preparation of a medicament for inhibiting the interaction of BACE with a physiological ligand.

In another embodiment, the present invention provides a method for increasing the α-secretory pathway in a human subject. In one embodiment, the invention provides a method for treating Alzheimer's Disease or dementia of the Alzheimer's type comprising: administering a compound, tautomer, or pharmaceutically acceptable salt of any one of embodiments 1 to 249 to a human, so as to increase the α-secretory pathway. In a further embodiment, the invention provides a compound, tautomer, or pharmaceutically acceptable salt of any one of embodiments 1 to 249 for use in increasing the α-secretory pathway in a human subject. In a further embodiment, the invention provides for the use of a compound, tautomer, or pharmaceutically acceptable salt of any one of embodiments 1 to 249 for the preparation of a medicament for increasing the α-secretory pathway in a human subject.

In each of the methods or uses described above, a compound, tautomer, or pharmaceutically acceptable salt of any of embodiments 1 to 249 may be administered to a subject as part of a pharmaceutically formulation, as described above.

Examples of compounds of Formula (I), tautomers of compounds of Formula (I), or pharmaceutically acceptable salts of either of the foregoing, of the present invention having potentially useful biological activity are listed by name below in Table 3. The ability of compounds Formula (I), tautomers of compounds of Formula (I), or a pharmaceutically acceptable salt of either of the foregoing, to inhibit the proteolytic activity of BACE was established with the representative compounds of Formula (I) listed in Table 3 using the enzyme and cell based assays described below.

Biological Assays

The following assay methods were used to identify and evaluate compounds of Formula (I) that are effective in reducing the proteolytic activity of BACE.

BACE Fluorescence Resonance Energy Transfer (FRET) Assay

In the following assay, the proteolytic activity of BACE is measured by observing cleavage of a fluorescent group from a peptide substrate containing a rhodamine fluorescent donor and a quenching acceptor.

The inhibitory activity of compounds of Formula (I) may be compared to a statine derived control inhibitor STA200 (MP Biomedical Cat. #STA-200). The cleavage reaction occurs when a BACE-1 substrate (Invitrogen, Cat. #P2986) was added to a reaction mixture containing BACE-1 enzyme (R & D Systems, Cat. #931AS) and allowed to proceed for about 1.5 hours. Fluorescence, used as a marker of BACE activity, is monitored using 540 nm excitation and 585 nm emission wavelengths (Envision, Perkin Elmer).

A typical assay reaction contains BACE-1 enzyme-in assay buffer (50 mM sodium acetate, pH 4-4.5, 0.01% CHAPS (3-[(3-Cholamidopropyl)dimethylammonio]-1-propanesulfonate), 0.0125% TritonX-100, 0.006% EDTA) which is pre-incubated for 30 minutes with test compound in 7.5% DMSO. The reaction is initiated with the addition of BACE-1 substrate in assay buffer and allowed to proceed for about 1.5 hours at room temperature. Assays are conducted in black 384-well microtiter plates and scanned at room temperature using 540 nm excitation and 585 nm emission wavelengths.

A test compound's activity is reported in Table 2 as the $IC_{50}$. In some instances, the percent inhibition at a given concentration is reported instead of the $IC_{50}$. An asterisk (*) indicates that the reported number is a mean.

Aβ Cell Based Assay Procedure

In the following assay, the proteolytic activity of BACE in cells exposed to varying concentrations of a compound of interest is measured by observing the amount of $A\beta_{1-40}$ secreted from HEK293 cells (Human Embryonic Kidney epithelial cell line) stably expressing wildtype human APP695 protein (HEK-APPwt cells).

HEK-APPwt cells were grown in high glucose DMEM (Dulbecco's Modified Eagles Medium SIGMA Cat. #D5796) supplemented with 25 mM HEPES (4-(2-hydroxyethyl)-1-piperazineethanesulfonic acid) (pH 7.4) (Invitrogen Cat. #15630-114), 0.1 mM NEAA (Non-essential Amino Acids) (BioWhittaker Cat. #13-114E), 10% fetal bovine serum (SIGMA Cat. #F4135) and 250 µg/mL hygromycin (Invitrogen Cat. #10687-010) in T-225 flasks at 37° C. with 5% $CO_2$ and humidity control.

Test compounds were initially prepared in DMSO and diluted with DMEM media containing 2% FBS (Fetal bovine serum). Ten standard compound solutions were prepared having a range of concentrations. The standard compound solutions were used to determine the $EC_{50}$ of the test compound. The range of concentrations chosen may depend on the compound's predicted potency.

To prepare cells for the assay, a flask containing HEK-APPwt cells were trypsinized briefly (1 mL trypsin), and once the cells detached, 4 mL of 10% FBS-DMEM was added to the flask. The detached cells were centrifuged at 900 rpm for 5 min to form a pellet.

The HEK-APPwt cell pellet was re-suspended with 10 mL DMEM media containing 2% FBS. 80 µL of the cell suspension was added to each well of a 96-well cell culture plate to give $100 \times 10^4$ cells/ml. 10 µL of a standard compound solution was added to each well of the 96-well cell culture plate followed by 10 µL of Alamar blue solution. The cells were incubated at 37° C. in a 5% $CO_2$ incubator for 6 hours.

At the end of the incubation, the plates were removed from incubator, and the supernatant was collected. $A\beta_{1-40}$ concentration in the medium was measured by using a commercial $A\beta_{1-x}$ ELISA kit (IBL, Japan Cat. #27729). Briefly, the ELISA plates were coated with an anti-human Aβ (N)(82E1) mouse IgG monoclonal antibody. A horseradish peroxidase conjugated anti-human Aβ11-28 mouse IgG monoclonal antibody was used for detection. The cell culture supernatant was diluted with EIA buffer+protease inhibitors (kit buffer containing protease inhibitors (1 mL PI/30 mL buffer)). A 100 µL aliquot of the diluted supernatant was added to each well of the ELISA plate and incubated for 6 hrs at 4° C. The ELISA plate was washed 8 times with phosphate buffered saline (PBS) containing 0.05% TWEEN 20.

A 100 µL of detection antibody was then added and incubated for 1 hour at 4° C. The plate was washed 8 times with PBS buffer containing 0.05% Tween 20 followed by addition of 100 µL of the chromogen tetramethylbenzidine (TMB). The plate was incubated in the dark at room temperature for about 30 min and a stop solution (1N $H_2SO_4$) was added.

The intensity of the color developed was measured at 450 nm. The optical density at 450 nm (OD450) is proportional to the concentration of human $A\beta_{1-40}$ secreted by the cell. As a reference, N—[N-(3,5-difluorophenacetyl-L-alanyl)]—S-phenylglycine t-butyl ester (DAPT, a γ-secretase inhibitor) was used to indicate 100% inhibition of BACE activity. Thus, the assay measures the ability of a compound of interest to reduce $A\beta_{1-40}$ secretion. Compound potency is reported in Table 3 as the $EC_{50}$ by calculating the percent inhibition at all concentration levels and the data were fit with non-linear curve fitting algorithm using GraphPad Prism. An asterisk (*) indicates that the reported number is a mean.

TABLE 2

| Example | $IC_{50}$ (µM) FRET assay |
|---|---|
| 1 | 0.099 |
| 2 | 0.286 |
| 3 | 0.132 |
| 4 | 0.105 |
| 5 | 0.095 |
| 6 | 0.244 |
| 7 | 0.225 |
| 8 | 0.280 |
| 9 | 0.300 |
| 10 | 0.297 |
| 11 | 0.320 |
| 12 | 0.376 |
| 13 | 0.368 |
| 14 | 0.152 |
| 15 | 0.272 |
| 16 | 0.289 |
| 17 | 0.171 |
| 18 | 0.219 |
| 19 | 0.166 |
| 20 | 0.205 |
| 21 | 0.318 |
| 22 | 0.249 |
| 23 | 0.272 |
| 24 | 0.291 |
| 25 | 0.316 |
| 26 | 0.222 |
| 27 | 0.262 |
| 28 | 0.253 |
| 29 | 0.314 |
| 30 | 0.270 |
| 31 | 0.313 |
| 32 | 0.234 |
| 33 | 0.278 |
| 34 | 0.270 |
| 35 | 0.315 |
| 36 | 0.332 |
| 37 | 0.322 |
| 38 | 0.270 |
| 39 | 0.197 |
| 40 | 0.307 |
| 41 | 0.232 |
| 42 | 0.365 |
| 43 | 0.335 |
| 44 | 0.241 |
| 45 | 0.198 |
| 46 | 0.248 |
| 47 | 0.240 |
| 48 | 0.315 |
| 49 | 0.210 |
| 50 | 0.267 |
| 51 | 0.173 |
| 52 | 0.223 |
| 53 | 0.216 |
| 54 | 0.211 |
| 55 | 0.212 |
| 56 | 0.176 |
| 57 | 0.104 |
| 58 | 0.368 |
| 59 | 0.194 |
| 60 | 0.140 |
| 61 | 0.335 |
| 62 | 0.335 |
| 63 | 0.361 |
| 64 | 0.220 |
| 65 | 0.238 |
| 66 | 0.255 |
| 67 | 0.261 |
| 68 | 0.344 |
| 69 | 0.300 |
| 70 | 0.381 |
| 71 | 0.327 |
| 72 | 0.216 |
| 73 | 0.346 |
| 74 | 0.219 |

TABLE 2-continued

| Example | IC$_{50}$ (μM) FRET assay |
| --- | --- |
| 75 | 0.360 |
| 76 | 0.230 |
| 77 | 0.242 |
| 78 | 0.337 |
| 79 | 0.320 |
| 80 | 0.200 |
| 81 | 0.393 |
| 82 | 1.070 |
| 83 | 0.180 |
| 84 | 0.191 |
| 85 | 0.089 |
| 86 | 0.123 |
| 87 | 0.560 |
| 88 | 0.476 |
| 89 | 0.160 |
| 90 | 1.384 |
| 91 | 2.341 |
| 92 | 75% @ 1.1 μM |
| 93 | 62% @ 1.1 μM |
| 94 | 80% @ 1.1 μM |
| 95 | 0.431 |
| 96 | 0.328 |
| 97 | 0.161 |
| 98 | 0.248* |
| 99 | 0.189 |
| 100 | 0.260 |
| 101 | 0.136 |
| 102 | 0.313 |
| 103 | 0.334 |
| 104 | 0.277 |
| 105 | 0.064 |
| 106 | 0.139 |
| 107 | 0.215 |
| 108 | 0.357 |
| 109 | 0.188 |
| 110 | 0.268 |
| 111 | 0.174 |
| 112 | 0.251* |
| 113 | 0.528 |
| 114 | 0.279* |
| 115 | 0.281 |
| 116 | 0.204 |
| 117 | 0.229 |
| 118 | 0.318 |
| 119 | 0.298 |
| 120 | 0.455* |
| 121 | 0.318 |
| 122 | 0.371* |
| 123 | 0.372* |
| 124 | 0.419 |
| 125 | 1.181 |
| 126 | 0.348 |
| 127 | 0.163 |
| 128 | 0.224 |
| 129 | 0.293 |
| 130 | 0.169 |
| 131 | 0.245* |
| 132 | 0.344* |
| 133 | 0.262 |
| 134 | 0.203 |
| 135 | 0.117 |
| 136 | 0.171 |
| 137 | 0.229 |
| 138 | 0.525 |
| 139 | 0.236 |
| 140 | 0.998 |
| 141 | 0.172 |
| 142 | 0.134 |
| 143 | 0.172* |
| 144 | 0.128* |
| 145 | 0.150 |
| 146 | 0.376 |
| 147 | 0.207 |

TABLE 3

| Example | EC$_{50}$ (μM) Cell-Based Assay |
| --- | --- |
| 7 | 0.70 |
| 25 | 1.35 |
| 26 | 1.41 |
| 27 | 0.58 |
| 29 | 2.58 |
| 31 | 2.50 |
| 32 | 0.59 |
| 35 | 3.13 |
| 40 | 2.68 |
| 41 | 2.62 |
| 43 | 2.88 |
| 45 | 1.31 |
| 46 | 3.81 |
| 47 | 1.96 |
| 49 | 1.80 |
| 50 | 0.58 |
| 53 | 2.62 |
| 54 | 0.87 |
| 64 | 0.97 |
| 69 | 2.93 |
| 83 | 1.47 |
| 84 | 1.71 |
| 85 | 2.27 |
| 86 | 2.46 |
| 92 | 0.31 |
| 93 | 0.91 |
| 94 | 0.32 |
| 98 | 0.44 |
| 99 | 0.78 |
| 100 | 0.70 |
| 101 | 1.17 |
| 102 | 1.95 |
| 104 | 0.33 |
| 105 | 1.27 |
| 106 | 0.86 |
| 107 | 0.79 |
| 108 | 0.89 |
| 109 | 0.80 |
| 112 | 0.48 |
| 113 | 1.71 |
| 114 | 0.33 |
| 115 | 3.27 |
| 116 | 0.44 |
| 117 | 1.16 |
| 118 | 1.06 |
| 119 | 0.77 |
| 120 | 0.07 |
| 121 | 1.94 |
| 122 | 0.10* |
| 123 | 0.12* |
| 124 | 0.30 |
| 126 | 0.23 |
| 127 | 0.71 |
| 128 | 0.26 |
| 130 | 0.23 |
| 131 | 0.15* |
| 132 | 0.47 |
| 133 | 0.56* |
| 134 | 0.75 |
| 135 | 0.45 |
| 136 | 0.97 |
| 139 | 0.43 |
| 140 | 2.25 |
| 141 | 1.30* |
| 142 | 0.63 |
| 143 | 1.07* |
| 144 | 0.94* |
| 145 | 1.09* |
| 146 | 0.11 |
| 147 | 0.27* |

While the invention has been described and illustrated with reference to certain embodiments thereof, those skilled in the art will appreciate that various changes, modifications and substitutions can be made therein without departing from the spirit and scope of the invention. For example, effective dosages other than the dosages as set forth herein may be applicable as a consequence of variations in the responsiveness of the subject being treated. Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention. Moreover, all compounds that are recited in the written description are contemplated as possibilities for any of the recited methods, processes, compositions, and/or compounds as appear in the written description and the appended claims.

The invention claimed is:

1. A compound of Formula (I) or a pharmaceutically acceptable salt thereof:

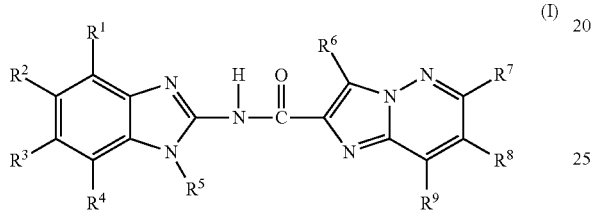

wherein $R^1$, $R^2$, $R^3$, and $R^4$ are each independently selected from the group consisting of:
a) —H,
b) -halogen,
c) —$C_{1-6}$ alkyl,
d) —$C_{3-10}$ cycloalkyl,
e) —$C_{1-4}$ alkylene-$C_{3-10}$ cycloalkyl,
f) -heterocyclyl,
g) —$C_{1-4}$ alkylene-heterocyclyl,
h) -phenyl,
i) —$C_{1-4}$ alkylene-phenyl,
j) -heteroaryl,
k) —$C_{1-4}$ alkylene-heteroaryl,
l) -cyano,
m) —$CF_3$,
n) —$OCF_3$,
o) —O—$R^a$,
p) —S(O)$_w$—$R^a$,
q) —S(O)$_2$O—$R^a$,
r) —$NR^aR^b$,
s) —C(O)—$R^a$,
t) —C(O)—O—$R^a$,
u) —OC(O)—$R^a$,
v) —C(O)$NR^aR^b$,
w) —$NR^aC(O)R^b$,
x) —OC(O)$NR^aR^b$,
y) —$NR^aC(O)OR^b$, and
z) —$NR^aC(O)NR^aR^b$,
where the alkyl, alkylene, cycloalkyl, heterocyclyl, phenyl, and heteroaryl groups are optionally substituted one or more times with substituents independently selected from $R^z$;

$R^5$ is hydrogen, —$C_{1-6}$ alkyl, or —$C_{1-4}$ alkylene-$C_{3-10}$ cycloalkyl, where the alkyl, alkylene, and cycloalkyl groups are optionally substituted one or more times with substituents independently selected from $R^z$;

$R^6$ is hydrogen, —$C_{1-6}$ alkyl, or —$C_{1-4}$ alkylene-$C_{3-10}$ cycloalkyl, where the alkyl, alkylene, and cycloalkyl groups are optionally substituted one or more times with substituents independently selected from $R^z$;

$R^7$ is:
a) —H,
b) -halogen,
c) —$C_{1-6}$ alkyl,
d) —$C_{3-10}$ cycloalkyl,
e) —$C_{1-4}$ alkylene-$C_{3-10}$ cycloalkyl,
f) -heterocyclyl,
g) —$C_{1-4}$ alkylene-heterocyclyl,
h) -phenyl,
i) —$C_{1-4}$ alkylene-phenyl,
j) -heteroaryl,
k) —$C_{1-4}$ alkylene-heteroaryl,
l) -cyano,
m) —$CF_3$,
n) —$OCF_3$,
o) —O—$R^c$,
p) —S(O)$_w$—$R^c$,
q) —S(O)$_2$O—$R^c$,
r) —$NR^cR^d$,
s) —C(O)—$R^c$,
t) —C(O)—O—$R^c$,
u) —OC(O)—$R^c$,
v) —C(O)$NR^cR^d$,
w) —$NR^cC(O)R^d$,
x) —OC(O)$NR^cR^d$,
y) —$NR^cC(O)OR^d$,
z) —$NR^cC(O)NR^cR^d$,
aa) —O—$C_{1-6}$ alkylene-O—$R^c$, or
bb) —O—$C_{1-6}$ alkylene-$NR^cR^d$,
where the alkyl, alkylene, cycloalkyl, heterocyclyl, phenyl, and heteroaryl groups are optionally substituted one or more times with substituents independently selected from $R^y$;

$R^8$ and $R^9$ are each independently selected from the group consisting of:
a) —H,
b) -halogen,
c) —$C_{1-6}$ alkyl,
d) —$C_{3-10}$ cycloalkyl,
e) —$C_{1-4}$ alkylene-$C_{3-10}$ cycloalkyl,
f) -heterocyclyl,
g) —$C_{1-4}$ alkylene-heterocyclyl,
h) -phenyl,
i) —$C_{1-4}$ alkylene-phenyl,
j) -heteroaryl,
k) —$C_{1-4}$ alkylene-heteroaryl,
l) -cyano,
m) —$CF_3$,
n) —$OCF_3$,
o) —O—$R^a$,
p) —S(O)$_w$—$R^a$,
q) —S(O)$_2$O—$R^a$,
r) —$NR^aR^b$,
s) —C(O)—$R^a$,
t) —C(O)—O—$R^a$,
u) —OC(O)—$R^a$,
v) —C(O)$NR^aR^b$,
w) —$NR^aC(O)R^b$,
x) —OC(O)$NR^aR^b$,
y) —$NR^aC(O)OR^b$, and
z) —$NR^aC(O)NR^aR^b$,
where the alkyl, alkylene, cycloalkyl, heterocyclyl, phenyl, and heteroaryl groups are optionally substituted one or more times with substituents independently selected from $R^z$;

$R^a$ and $R^b$ are independently selected from the group consisting of hydrogen, —$C_{1-6}$ alkyl, —$C_{3-10}$ cycloalkyl, heterocyclyl, phenyl, heteroaryl, —$C_{1-4}$ alkylene-$C_{3-10}$ cycloalkyl, —$C_{1-4}$ alkylene-heterocyclyl, —$C_{1-4}$ alkylene-phenyl, and —$C_{1-4}$ alkylene-heteroaryl, where the alkyl, alkylene, cycloalkyl, heterocyclyl, phenyl, and heteroaryl groups are optionally substituted one or more times with substituents independently selected from $R^z$; or, if $R^a$ and $R^b$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, azepano, 2-oxo-pyrrolidin-1-yl, 2-oxo-imidazolidin-1-yl, 2-oxo-oxazolidin-3-yl, 2-oxo-thiazolidin-3-yl, 3-oxo-isoxazolidin-2-yl, 3-oxo-isothiazolidin-3-yl, 2-oxo-piperidin-1-yl, 2-oxo-piperazin-1-yl, 3-oxo-morpholin-4-yl, 3-oxo-thiomorpholin-4-yl, 2-oxo-azepan-1-yl, 1H-pyrrol-1-yl, 3-pyrrolin-1-yl, imidazol-1-yl, 2-imidazolin-1-yl, 1H-pyrazol-1-yl, 2-pyrazolin-1-yl, 1,2,3-triazol-1-yl, 1,2,4-triazol-1-yl, and tetrazol-1-yl, where each ring is optionally substituted one or more times with substituents independently selected from $R^z$;

$R^c$ and $R^d$ are independently selected from the group consisting of hydrogen, —$C_{1-6}$ alkyl, —$C_{3-10}$ cycloalkyl, heterocyclyl, phenyl, heteroaryl, —$C_{1-4}$ alkylene-$C_{3-10}$ cycloalkyl, —$C_{1-4}$ alkylene-heterocyclyl, —$C_{1-4}$ alkylene-phenyl, and —$C_{1-4}$ alkylene-heteroaryl, where the alkyl, alkylene, cycloalkyl, heterocyclyl, phenyl, and heteroaryl groups are optionally substituted one or more times with substituents independently selected from $R^y$; or, if $R^c$ and $R^d$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, azepano, 2-oxo-pyrrolidin-1-yl, 2-oxo-imidazolidin-1-yl, 2-oxo-oxazolidin-3-yl, 2-oxo-thiazolidin-3-yl, 3-oxo-isoxazolidin-2-yl, 3-oxo-isothiazolidin-3-yl, 2-oxo-piperidin-1-yl, 2-oxo-piperazin-1-yl, 3-oxo-morpholin-4-yl, 3-oxo-thiomorpholin-4-yl, 2-oxo-azepan-1-yl, 1H-pyrrol-1-yl, 3-pyrrolin-1-yl, imidazol-1-yl, 2-imidazolin-1-yl, 1H-pyrazol-1-yl, 2-pyrazolin-1-yl, 1,2,3-triazol-1-yl, 1,2,4-triazol-1-yl, and tetrazol-1-yl, where each ring is optionally substituted one or more times with substituents independently selected from $R^y$;

$R^e$ and $R^f$ are independently selected from the group consisting of hydrogen, —$C_{1-6}$ alkyl, —$C_{3-10}$ cycloalkyl, heterocyclyl, phenyl, 1-naphthyl, 2-naphthyl, heteroaryl, —$C_{1-4}$ alkylene-$C_{3-10}$ cycloalkyl, —$C_{1-4}$ alkylene-heterocyclyl, —$C_{1-4}$ alkylene-phenyl, and —$C_{1-4}$ alkylene-heteroaryl, where the alkyl, alkylene, cycloalkyl, heterocyclyl, phenyl, naphthyl, and heteroaryl groups are optionally substituted one or more times with substituents independently selected from the group consisting of halogen, methyl, ethyl, isopropyl, —$CF_3$, —$OCH_3$, —$OCH_2CH_3$, —$OCH(CH_3)_2$, —$OCF_3$, —$OCH_2CF_3$; or, if $R^e$ and $R^f$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, azepano, 2-oxo-pyrrolidin-1-yl, 2-oxo-imidazolidin-1-yl, 2-oxo-oxazolidin-3-yl, 2-oxo-thiazolidin-3-yl, 3-oxo-isoxazolidin-2-yl, 3-oxo-isothiazolidin-3-yl, 2-oxo-piperidin-1-yl, 2-oxo-piperazin-1-yl, 3-oxo-morpholin-4-yl, 3-oxo-thiomorpholin-4-yl, 2-oxo-azepan-1-yl, 1H-pyrrol-1-yl, 3-pyrrolin-1-yl, imidazol-1-yl, 2-imidazolin-1-yl, 1H-pyrazol-1-yl, 2-pyrazolin-1-yl, 1,2,3-triazol-1-yl, 1,2,4-triazol-1-yl, and tetrazol-1-yl, where each ring is optionally substituted one or more times with substituents independently selected from the group consisting of halogen, methyl, ethyl, isopropyl, —$CF_3$, —$OCH_3$, —$OCH_2CH_3$, —$OCH(CH_3)_2$, —$OCF_3$, —$OCH_2CF_3$;

$R^y$ is
a) -halogen,
b) —$NR^eR^f$,
c) —O—$R^e$,
d) —S—$R^e$,
e) —$S(O)_2$—$R^e$,
f) -cyano,
g) —C(O)—$R^e$,
h) —C(O)—O—$R^e$,
i) —$C(O)NR^eR^f$,
j) —$C_{1-6}$ alkyl, optionally substituted one or more times with substituents selected independently from the group consisting of halogen and —OH,
k) -heterocyclyl, optionally substituted one or more times with substituents selected independently from the group consisting of halogen and —OH,
l) —$C_{3-10}$ cycloalkyl, optionally substituted one or more times with substituents selected independently from the group consisting of halogen and —OH,
m) —$CF_3$,
n) —$OCF_3$,
o) -phenyl, optionally substituted one or more times with substituents selected independently from the group consisting of halogen and —OH, or
p) -heteroaryl; optionally substituted one or more times with substituents selected independently from the group consisting of halogen and —OH;

$R^z$ is
a) -halogen,
b) —$NR^eR^f$,
c) —O—$R^e$,
d) —S—$R^e$,
e) —$S(O)_2$—$R^e$,
f) -cyano,
g) —C(O)—$R^e$,
h) —C(O)—O—$R^e$,
i) —$C(O)NR^eR^f$,
j) —$C_{1-6}$ alkyl, optionally substituted one or more times with halogen,
k) -heterocyclyl, optionally substituted one or more times with halogen,
l) —$C_{3-10}$ cycloalkyl, optionally substituted one or more times with halogen,
m) —$CF_3$,
n) —$OCF_3$,
o) -phenyl, optionally substituted one or more times with halogen, or
p) -heteroaryl; optionally substituted one or more times with halogen; and w is an integer from 0 to 2;
wherein at least one of $R^2$ and $R^3$ is not —H;
or, if $R^5$ is —H, a tautomer of any of the foregoing.

2. The compound of claim 1, wherein $R^1$, $R^3$, and $R^4$ are —H.

3. The compound of claim 2, wherein $R^5$ is —H.

4. The compound of claim 3, wherein $R^6$ is —H.

5. The compound of claim 4, wherein $R^8$ and $R^9$ are —H.

6. The compound of claim 5, wherein $R^2$ is —O—CH$_2$-phenyl, phenyl, cyclopentyl, or cyclohexyl, where the phenyl, cyclopentyl, and cyclohexyl moieties are optionally substituted one or more times with substituents selected independently from the group consisting of halogen, —CF$_3$, —O—CF$_3$, —CH$_3$, and —OCH$_3$.

7. The compound of claim 6, wherein $R^2$ is phenyl optionally substituted one or more times with substituents selected independently from the group consisting of halogen, —CF$_3$, —O—CF$_3$, —CH$_3$, and —OCH$_3$.

8. The compound of claim 7, wherein $R^7$ is —O—C$_{1-6}$ alkylene-O—R$^c$, where R$^c$ is —C$_{1-6}$ alkyl optionally substituted one or more times with substituents selected independently from the group consisting of halogen and —OH, and the alkylene is optionally substituted one or more times with halogen.

9. The compound of claim 7, wherein $R^7$ is —O—C$_{1-6}$ alkylene-O—R$^c$, where R$^c$ is —H, and the alkylene is optionally substituted one or more times with halogen.

10. The compound of claim 9, wherein $R^7$ is —O—C$_{1-6}$ alkylene-OH.

11. The compound of claim 1, wherein the compound is 6-Methoxy-imidazo[1,2-b]pyridazine-2-carboxylic acid [6-(3-chloro-5-fluoro-phenyl)-1H-benzoimidazol-2-yl]-amide or a pharmaceutically acceptable salt thereof.

12. The compound of claim 1, wherein the compound is 6-(2-Methoxy-ethoxy)-imidazo[1,2-b]pyridazine-2-carboxylic acid [5-(3-trifluoromethyl-phenyl)-1H-benzoimidazol-2-yl]-amide or a pharmaceutically acceptable salt thereof.

13. The compound of claim 1, wherein the compound is 6-(2-Dimethylamino-ethoxy)-imidazo[1,2-b]pyridazine-2-carboxylic acid [5-(3-trifluoromethyl-phenyl)-1H-benzoimidazol-2-yl]-amide or a pharmaceutically acceptable salt thereof.

14. The compound of claim 1, wherein the compound is 6-(2-Morpholin-4-yl-ethoxy)-imidazo[1,2-b]pyridazine-2-carboxylic acid [5-(3-chloro-5-fluoro-phenyl)-1H-benzoimidazol-2-yl]-amide or a pharmaceutically acceptable salt thereof.

15. The compound of claim 1, wherein the compound is 6-((1S,3S)-3-Hydroxy-cyclopentyloxy)-imidazo[1,2-b]pyridazine-2-carboxylic acid [5-(3-chloro-5-fluoro-phenyl)-1H-benzoimidazol-2-yl]-amide or a pharmaceutically acceptable salt thereof.

16. The compound of claim 1, wherein the compound is 6-((R)-2-Hydroxy-propoxy)-imidazo[1,2-b]pyridazine-2-carboxylic acid [5-(3-chloro-4-trifluoromethyl-phenyl)-1H-benzoimidazol-2-yl]-amide or a pharmaceutically acceptable salt thereof.

17. The compound of claim 1, wherein the compound is 6-((S)-2-Hydroxy-propoxy)-imidazo[1,2-b]pyridazine-2-carboxylic acid [5-(3-chloro-4-trifluoromethyl-phenyl)-1H-benzoimidazol-2-yl]-amide or a pharmaceutically acceptable salt thereof.

18. The compound of claim 1, wherein the compound is 6-(2-Hydroxy-ethoxy)-imidazo[1,2-b]pyridazine-2-carboxylic acid [5-(3-chloro-4-fluoro-phenyl)-1H-benzoimidazol-2-yl]-amide or a pharmaceutically acceptable salt thereof.

19. The compound of claim 1, wherein the compound is 6-(2-Hydroxy-ethoxy)-imidazo[1,2-b]pyridazine-2-carboxylic acid [5-(3-trifluoromethoxy-phenyl)-1H-benzoimidazol-2-yl]-amide or a pharmaceutically acceptable salt thereof.

20. The compound of claim 1, wherein the compound is 6-(2-Hydroxy-ethoxy)-imidazo[1,2-b]pyridazine-2-carboxylic acid [5-(3-chloro-phenyl)-1H-benzoimidazol-2-yl]-amide or a pharmaceutically acceptable salt thereof.

21. The compound of claim 1, wherein the compound is 6-((S)-2-Hydroxy-propoxy)-imidazo[1,2-b]pyridazine-2-carboxylic acid [5-(3-trifluoromethoxy-phenyl)-1H-benzoimidazol-2-yl]-amide or a pharmaceutically acceptable salt thereof.

22. A pharmaceutical composition comprising a compound of claim 1 and a pharmaceutically acceptable carrier, excipient, or diluent.

\* \* \* \* \*